United States Patent
Doherty et al.

(10) Patent No.: US 7,524,874 B2
(45) Date of Patent: *Apr. 28, 2009

(54) VANILLOID RECEPTOR LIGANDS AND THEIR USE IN TREATMENTS

(75) Inventors: Elizabeth M. Doherty, Newbury Park, CA (US); Jiawang Zhu, Simi Valley, CA (US); Markian Stec, Fillmore, CA (US); Mark H. Norman, Thousand Oaks, CA (US); Vassil I. Ognyanov, Thousand Oaks, CA (US); Christopher H. Fotsch, Thousand Oaks, CA (US); Ning Chen, Thousand Oaks, CA (US); Partha P. Chakrabarti, Simi Valley, CA (US); Liping H. Pettus, Thousand Oaks, CA (US); Hui-Ling Wang, Thousand Oaks, CA (US); Xianghong Wang, Moorpark, CA (US); Premilla Arasasingham, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 328 days.

This patent is subject to a terminal disclaimer.

(21) Appl. No.: 11/195,302

(22) Filed: Aug. 1, 2005

(65) Prior Publication Data
US 2005/0267163 A1 Dec. 1, 2005

Related U.S. Application Data

(62) Division of application No. 10/445,170, filed on May 20, 2003, now Pat. No. 7,053,088.

(60) Provisional application No. 60/383,331, filed on May 22, 2002.

(51) Int. Cl.
| C07D 213/30 | (2006.01) |
| C07D 213/32 | (2006.01) |
| C07D 213/36 | (2006.01) |
| C07D 401/12 | (2006.01) |
| C07D 401/14 | (2006.01) |
| C07D 403/12 | (2006.01) |
| C07D 403/14 | (2006.01) |
| A61K 31/4422 | (2006.01) |
| A61K 31/506 | (2006.01) |
| A61P 19/02 | (2006.01) |

(52) U.S. Cl. ............ 514/345; 546/256; 546/268.1; 544/8; 544/53; 544/106; 544/319; 544/320; 540/450; 540/484; 514/231.5; 514/245; 514/269; 514/275

(58) Field of Classification Search .......... 546/256, 546/268.1; 514/345
See application file for complete search history.

(56) References Cited

U.S. PATENT DOCUMENTS 2,691,655 A 10/1954 Hitchings et al.
3,707,560 A 12/1972 De Angelis et al.
4,725,600 A 2/1988 Takaya et al.
5,272,167 A 12/1993 Girijavallabhan et al.
5,459,144 A 10/1995 Girijavallabhan et al.
5,461,053 A 10/1995 Biogegrain et al.
5,750,532 A 5/1998 Girijavallabhan et al.
5,916,887 A 6/1999 Singh et al.
5,932,590 A 8/1999 Ciccarone et al.
5,936,084 A 8/1999 Jirousek et al.
5,959,123 A 9/1999 Singh et al.
5,965,569 A 10/1999 Camps Garcia et al.
5,969,140 A 10/1999 Ukita et al.
6,093,737 A 7/2000 Anthony et al.
6,255,489 B1 7/2001 Klintz et al.
6,569,847 B1 5/2003 Singh et al.
7,053,088 B2 * 5/2006 Doherty et al. ............ 514/247
7,335,672 B2 * 2/2008 Norman et al. ............ 514/345
2002/0137755 A1 9/2002 Bilodeau et al.

(Continued)

FOREIGN PATENT DOCUMENTS

EP 0 937 459 1/1999

(Continued)

OTHER PUBLICATIONS

Harada et al. WO 02/06237, CA 136: 118474, 2002.*

(Continued)

*Primary Examiner*—Venkataraman Balasubramanian
(74) *Attorney, Agent, or Firm*—Richard V. Person

(57) ABSTRACT

Compounds having the general structure

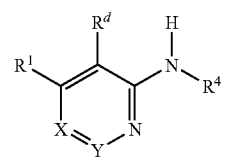

and compositions containing them, for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

19 Claims, No Drawings

U.S. PATENT DOCUMENTS

2004/0204386 A1 10/2004 Bhatt et al.

FOREIGN PATENT DOCUMENTS

| EP | 1 300 399 | 4/2003 |
|---|---|---|
| WO | WO 97/13754 | 4/1997 |
| WO | WO 97/41127 | 11/1997 |
| WO | WO 98/12176 | 3/1998 |
| WO | WO 98/12210 | 3/1998 |
| WO | WO 98/28980 | 7/1998 |
| WO | WO 99/12911 | 3/1999 |
| WO | WO 99/28314 | 6/1999 |
| WO | WO 99/41248 | 8/1999 |
| WO | WO 99/51241 | 10/1999 |
| WO | WO 00/59881 | 10/2000 |
| WO | WO 01/05768 | 1/2001 |
| WO | WO 01/07032 | 2/2001 |
| WO | WO 01/07401 | 2/2001 |
| WO | WO-01/12621 A1 * | 2/2001 |
| WO | WO 01/14331 | 3/2001 |
| WO | WO 01/42241 | 6/2001 |
| WO | WO 01/74331 | 10/2001 |
| WO | WO 01/76582 | 10/2001 |
| WO | WO 01/87845 | 11/2001 |
| WO | WO-01/93682- * | 12/2001 |
| WO | WO 02/00651 | 1/2002 |
| WO | WO 02 04427 | 1/2002 |
| WO | WO 02/12198 | 2/2002 |
| WO | WO 02/18339 | 3/2002 |
| WO | WO 02/22605 | 3/2002 |
| WO | WO 02/26712 | 4/2002 |
| WO | WO 02/36586 | 5/2002 |
| WO | WO 02/50052 | 6/2002 |
| WO | WO 02/079197 | 10/2002 |
| WO | WO 02/080853 | 10/2002 |
| WO | WO 02/088111 | 11/2002 |
| WO | WO 03/006471 | 1/2003 |
| WO | WO 03/028729 | 4/2003 |
| WO | WO 03/041649 | 5/2003 |
| WO | WO 03/093242 | 11/2003 |
| WO | WO 2004/005283 | 1/2004 |
| WO | WO 2004/046133 | 6/2004 |
| WO | WO 2004/065378 | 8/2004 |
| WO | WO 2004/089286 | 10/2004 |

OTHER PUBLICATIONS

Zimmermann et al. Archiv der Pharmazie 329(7): 371-376, 1996, CA 125: 184908, 1996.*

Shams et al. Journal fuer Praktische Chemie (Liepzig), 330(5): 817,1988, CA 111: 97050, 1989.*

El-Sakka et al. Environmental & Biomedical Problems, 48(2): 7-16, 1995, CA 123: 112011, 1995.*

Elkasby et al. Indian Journal of Chemistry, Section B: 20B(5): 428-31, 1981, CA 95: 150360, 1981.*

Robev, Heterocycles 1494): 461-464, 1980, CA 93: 46364, 1980.*

Abdalla et al. Pakistan Journal of Scientific and Industrial Research, 20(3): 139-49, 1979, CA 90: 137633, 1979.*

Fusco et al. Gazzetta Chimica Italinana 98(5): 511-534, 1968. CA 69: 96598, 1968.*

Kumar, et al., A Novel and Convenient Synthesis of 2-Amino-4-(N-alkyl-N-arylamino)-pyrimidines using Polarized Ketene S,S- and S,N-Acetals, Synthesis, 9: 748-751 (1980).

Lee, et al., N-(3-Acloxy-2-benzylpropyl)-N-[4-(methylsufonylamino)benzyl]thiourea Analogues: Novel Potent and High Affinity Antagonists and Partial Antagonists of the Vanilloid Receptor, J Med. Chem., 46: 3116-3126 (2003).

Hajduk, et al., "Novel Inhibitors of Erm Methyltransferases from NMR and Parallel Synthesis" J. Med Chem, 42, 19: 3852-3859 (1999).

Abstract of Bebbington et al., WO 02/22605 (4 pages), May 21, 2002.

Matsuda, et al., Bioorganic & Medicinal Chemistry Letters "Synthesis and Bioactivities of Novel Pyridazine Derivatives: Inhibitors of Interleukin-1 Beta (IL-1β) Production" 11(17) 2369-2372 (2001).

Valenzano, et al., Curr Med Chem (PubMed Abstract provided) "Current perspectives on the therapeutic utility of VR1 antagonists" 3185-3202 (2004).

Szallasi, et al., J of Medicinal Chemistry "Vanilloid Receptor TRPV1 Antagonists as the Next Generation of Painkillers. Are We Putting the Chart before the Horse?" 47(11) 2717-2723 (2004).

* cited by examiner

VANILLOID RECEPTOR LIGANDS AND THEIR USE IN TREATMENTS

This application is a division of application Ser. No. 10/445,170, filed May 20, 2003, now U.S. Pat. No. 7,053,088, claims benefit of US Provisional Application No. 60/383,331, filed May 22, 2002, which is hereby incorporated by reference.

BACKGROUND

The vanilloid receptor 1 (VR1) is the molecular target of capsaicin, the active ingredient in hot peppers. Julius et al. reported the molecular cloning of VR1 (Caterina et al., 1997). VR1 is a non-selective cation channel which is activated or sensitized by a series of different stimuli including capsaicin and resiniferatoxin (exogenous activators), heat & acid stimulation and products of lipid bilayer metabolism, anandamide (Premkumar et al., 2000, Szabo et al., 2000, Gauldie et al., 2001, Olah et al., 2001) and lipoxygenase metabolites (Hwang et al., 2000). VR1 is highly expressed in primary sensory neurons (Caterina et al., 1997) in rats, mice and humans (Onozawa et al., 2000, Mezey et al., 2000, Helliwell et al., 1998, Cortright et al., 2001). These sensory neurons innervate many visceral organs including the dermis, bones, bladder, gastrointestinal tract and lungs; VR1 is also expressed in other neuronal and non-neuronal tissues including but not limited to, CNS nuclei, kidney, stomach and T-cells (Nozawa et al., 2001, Yiangou et al., 2001, Birder et al., 2001). Presumably expression in these various cells and organs may contribute to their basic properties such as cellular signaling and cell division.

Prior to the molecular cloning of VR1, experimentation with capsaicin indicated the presence of a capsaicin sensitive receptor, which could increase the activity of sensory neurons in humans, rats and mice (Holzer, 1991; Dray, 1992, Szallasi and Blumberg 1996, 1999). The results of acute activation by capsaicin in humans was pain at injection site and in other species increased behavioral sensitivity to sensory stimuli (Szallasi and Blumberg, 1999). Capsaicin application to the skin in humans causes a painful reaction characterized not only by the perception of heat and pain at the site of administration but also by a wider area of hyperalgesia and allodynia, two characteristic symptoms of the human condition of neuropathic pain (Holzer, 1991). Taken together, it seems likely that increased activity of VR1 plays a significant role in the establishment and maintenance of pain conditions. Topical or intradermal injection of capsaicin has also been shown to produce localized vasodilation and edema production (Szallasi and Blumberg 1999, Singh et al., 2001). This evidence indicates that capsaicin through it's activation of VR1 can regulate afferent and efferent function of sensory nerves. Sensory nerve involvement in diseases could therefore be modified by molecules which effect the function of the vanilloid receptor to increase or decrease the activity of sensory nerves.

VR1 gene knockout mice have been shown to have reduced sensory sensitivity to thermal and acid stimuli (Caterina et al., 2000)). This supports the concept that VR1 contributes not only to generation of pain responses (i.e. via thermal, acid or capsaicin stimuli) but also to the maintenance of basal activity of sensory nerves. This evidence agrees with studies demonstrating capsaicin sensitive nerve involvement in disease. Primary sensory nerves in humans and other species can be made inactive by continued capsaicin stimulation. This paradigm causes receptor activation induced desensitization of the primary sensory nerve—such reduction in sensory nerve activity in vivo makes subjects less sensitive to subsequent painful stimuli. In this regard both capsaicin and resinferatoxin (exogenous activators of VR1), produce desensitization and they have been used for many proof of concept studies in in vivo models of disease (Holzer, 1991, Dray 1992, Szallasi and Blumberg 1999).

VR1 agonists or antagonists have use as analgesics for the treatment of pain of various genesis or aetiology, for example acute, inflammatory and neuropathic pain, dental pain and headache, particularly vascular headache such as migraine, cluster headache and mixed vascular syndromes as well as non-vascular, tension headache. They are also useful as anti-inflammatory agents for the treatment of inflammatory diseases or conditions, for example the treatment of arthritis and rheumatic diseases, osteoarthritis, inflammatory bowel disorders, inflammatory eye disorders (e.g. uvetis), inflammatory or unstable bladder disorders (e.g. cystitis and urinary incontinence), psoriasis and skin complaints with inflammatory components, as well as other chronic inflammatory conditions. They are, in particular, useful in the treatment of inflammatory pain and associated hyperalgesia and allodynia. They are also useful in the treatment of neuropathic pain and associated hyperalgesia and allodynia, e.g. trigeminal or herpetic neuralgia, diabetic neuropathy pain, causalgia, sympathetically maintained pain and deafferentation syndromes such as brachial plexus avulsion. They are also indicated for the use in the prophylactic or curative treatment of asthma, of epithelial tissue damage or dysfunction, e.g. spontaneous lesions, of herpes simplex, and in the control of disturbances of visceral motility at respiratory, genitourinary, gastrointestinal or vascular e.g. for treating wounds, burns, allergic skin reactions, pruritis and vitiligo, for the prophylactic or curative treatment of gastrointestinal disorders such as gastric ulceration, duodenal ulcers, inflammatory bowel disease and diarrhea, gastric lesions induced by necrotising agents, for example ethanol or chemotherapeutic agents, hair growth, for the treatment of vasomotor or allergic rhinitis and for the treatment of bronchial disorders or bladder disorders, such as bladder hyper-reflexia.

BIBLIOGRAPHY

Birder-L A. Kanai-A J. de-Groat-W C. Kiss-S. Nealen-M L. Burke-N E. Dineley-K E. Watkins-S. Reynolds-I J. Caterina-M J. (2001) Vanilloid receptor expression suggests a sensory role for urinary bladder epithelial cells. PNAS 98: 23: 13396-13401.

Caterina, M. J, Schumacher, M. A., Tominaga, M., Rosen, T. A., Levine, J. D., and Julius, D, (1997). The capsaicin receptor: a heat-activated ion channel in the pain pathway. Nature 389: 816-824.

Caterina-M J. Leffler-A. Malmberg-A B. Martin-W J. Trafton-J. Petersen-Zeitz K R. Koltzenburg-M. Basbaum-A I. Julius-D (2000) Impaired nociception and pain sensation in mice lacking the capsaicin receptor. Science-(WASH-DC). 288: 5464: 306-313.

Cortright-D N. Crandall-M. Sanchez-J F. Zou-T. Krause-J E. White-G (2001) The tissue distribution and functional characterization of human VR1. Biochemical and Biophysical Research Communications 281: 5: 1183-1189

Dray, A., (1992). Therapeutic potential of capsaicin-like molecules. Life Sciences 51: 1759-1765.

Gauldie-S D. McQueen-D S. Pertwee-R. Chessell-I P. (2001) Anandamide activates peripheral nociceptors in normal and arthritic rat knee joints. British Journal of Pharmacology 132: 3: 617-621.

Helliwell-R J A. McLatchie-L M. Clarke-M. Winter-J. Bevan-S. McIntyre-P (1998) Capsaicin sensitivity is associated with expression of the vanilloid (capsaicin) receptor (VR1) mRNA in adult rat sensory ganglia. Neuroscience Lett. 250: 3: 177-180.

Holzer, P. (1991) Capsaicin: Cellular targets, Mechanisms of Action and selectivity for thin sensory neurons. Pharmacological reviews 43: 2: 143-201

Hwang-S W. Cho-H. Kwak-J. Lee-S Y. Kang-C J. Jung-J. Cho-S. Min-K H. Suh-Y G. Kim-D. Oh-U. (2000) Direct activation of capsaicin receptors by products of lipoxygenases: Endogenous capsaicin-like substances. PNAS97: 11: 6155-6160.

Mezey-E. Toth-Z E. Cortright-D N. Arzubi-M K. Krause-J E. Elde-R. Guo-A. Blumberg-P M. Szallasi-A (2000) Distribution of mRNA for vanilloid receptor subtype 1 (VR1), and VR1-like immunoreactivity, in the central nervous system of the rat and human. PNAS 97: 7: 3655-3660.

Nozawa-Y. Nishihara-K. Yamamoto-A. Nakano-M. Ajioka-H. Matsuura-N. (2001) Distribution and characterization of vanilloid receptors in the rat stomach. Neuroscience Letters 309: 1: 33-36.

Olah-Z. Karai-L. Iadarola-M J. (2001) Anandamide activates vanilloid receptor 1 (VR1) at acidic pH in dorsal root ganglia neurons and cells ectopically expressing VR1. Journal of Biological Chemistry 276: 33, 31163-31170.

Onozawa-K. Nakamura-A. Tsutsumi-S. Yao-J. Ishikawa-R. Kohama-K. (2000) Tissue distribution of capsaicin receptor in the various organs of rats. Proc. Jpn. Acad. Ser. B, Phys.-Biol. Sci. 76: 5: 68-72.

Premkumar-L S. Ahemr-G P. (2000) Induction of vanilloid receptor channel activity by protein kinase C. Nature (London) 408: 6815: 985-990.

Singh-L K. Pang-X. Alexacos-N. Letourneau-R. Theoharides-T C. (1999) Acute immobilization stress triggers skin mast cell degranulation via corticotropin releasing hormone, neurotensin, and substance P: A link to neurogenic skin disorders. Brain Behav. Immun. 13: 3: 225-239.

Szallasi, A. Blumberg-P M (1996) Vanilloid receptors: New insights enhance potential as a therapeutic target. Pain 68: 195-208

Szallasi-A. Blumberg-P M. (1999) Vanilloid (capsaicin) receptors and mechanisms. Pharmacol. Rev. 51: 2: 159-211.

Szabo-T. Wang-J. Gonzalez-A. Kedei-N. Lile-J. Treanor-J. Blumberg-P M. (2000) Pharmacological characterization of the human vanilloid receptor type-1 (hVR1). Society for Neuroscience Abstracts. 26:1-2: 634.18.

Tominaga, M., Caterina, M. J., Malmberg, A. B., Rosen, T. A., Gilbert, H., Skinner, K., Raumann, B. E., Basbaum, A. I., and Julius, D., (1998). The cloned capsaicin receptor integrates multiple pain-producing stimuli. Neuron 21: 531-543.

Yiangou-Y. Facer-P. Dyer-N H C. Chan-C L H. Knowles-C. Williams-N S. Anand-P. (2001) Vanilloid receptor 1 immunoreactivity in inflamed human bowel. Lancet (North American Edition) 357: 9265: 1338-1339.

Yiangou-Y. Facer-P. Ford-A. Brady-C. Wiseman-O. Fowler-C J. Anand-P. (2001) Capsaicin receptor VR1 and ATP-gated ion channel P2X3 in human urinary bladder. BJU International 87: 9: 774-779.

Wang-H. Bian-D. Zhu-D. Zajic-G. Loeloff-R. Lile-J. Wild-K. Treanor-J. Curran-E. (2000) Inflammation-induced upregulation of VR1 in rat spinal cord and DRG correlates with enhanced nociceptive processing. Society for Neuroscience Abstracts 26:1-2: 632.15.

SUMMARY

The present invention comprises a new class of compounds useful in the treatment of diseases, such as vanilloid-receptor-mediated diseases and other maladies, such as inflammatory or neuropathic pain and diseases involving sensory nerve function such as asthma, rheumatoid arthritis, osteoarthritis, inflammatory bowel disorders, urinary incontinence, migraine and psoriasis. In particular, the compounds of the invention are useful for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. Accordingly, the invention also comprises pharmaceutical compositions comprising the compounds, methods for the treatment of vanilloid-receptor-mediated diseases, such as inflammatory or neuropathic pain, asthma, rheumatoid arthritis, osteoarthritis, inflammatory bowel disorders, urinary incontinence, migraine and psoriasis diseases, using the compounds and compositions of the invention, and intermediates and processes useful for the preparation of the compounds of the invention.

The compounds of the invention are represented by the following general structure:

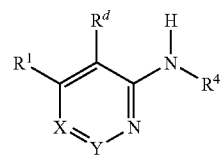

or a pharmaceutically acceptable salt thereof, wherein $R^1$, $R^4$, $R^d$, X and Y are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION

One aspect of the current invention relates to compounds having the general structure:

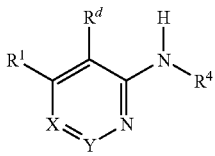

or any pharmaceutically-acceptable salt thereof, wherein:
X is =N— or =C(R$^2$)—;
Y is =N— or =C(R$^3$)—, wherein at least one of X and Y is not =N—;
n is independently, at each instance, 0, 1 or 2.
R$^1$ is

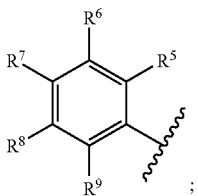

or R$^1$ is a naphthyl substituted by 0, 1, 2 or 3 substituents independently selected from R$^5$; or R$^1$ is R$^b$ substituted by 1, 2 or 3 substituents independently selected from R$^5$;

R$^2$ is, independently, in each instance, R$^{10}$, C$_{1-8}$alkyl substituted by 0, 1 or 2 substituents selected from R$^{10}$, —(CH$_2$)$_n$phenyl substituted by 0, 1, 2 or 3 substituents independently selected from R$^{10}$, or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from R$^{10}$;

R$^3$ is, independently, in each instance, H, halo, —NH$_2$, —NHC$_{1-3}$alkyl, —N(C$_{1-3}$alkyl)C$_{1-3}$alkyl, or C$_{1-3}$alkyl; wherein, when X is =C(R$^2$)— and Y is =C(R$^3$)— then at least one of R$^2$ and R$^3$ is other than H;

R$^4$ is

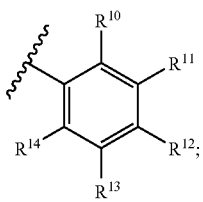

or

R$^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from R$^e$, C$_{1-4}$haloalkyl, halo, nitro, cyano, oxo, —OR$^f$, —S(=O)$_n$R$^e$, —OC$_{1-4}$haloalkyl, —OC$_{2-6}$alkylNR$^a$R$^f$, —OC$_{2-6}$alkylOR$^f$, —OC$_{1-6}$alkylC(=O)OR$^e$, —NR$^a$R$^f$, —NR$^a$C$_{1-4}$haloalkyl, —NR$^a$C$_{2-6}$alkylNR$^a$R$^f$, —NR$^a$C$_{2-6}$alkylOR$^f$, —C(=O)R$^e$, —C(=O)OR$^e$, —OC(=O)OR$^e$, —C(=O)NR$^a$R$^f$ and —NR$^a$C(=O)R$^e$; and unsaturated carbon atoms may be additionally substituted by =O; and any available nitrogen atoms in the heterocycle and bridge are substituted by H, —C$_{1-6}$alkylOR$^f$, R$^e$, —C$_{1-6}$alkylNR$^a$R$^f$, —C$_{1-3}$alkylC(=O)OR$^e$, —C$_{1-3}$alkylC(=O)NR$^a$R$^f$, —C$_{1-3}$alkylOC(=O)R$^e$, —C$_{1-3}$alkylNR$^a$C(=O)R$^e$, —C(=O)R$^c$ or —C$_{1-3}$alkylR$^c$; or R$^4$ is naphthyl substituted by 1, 2 or 3 substituents independently selected from C$_{1-4}$haloalkyl, halo, nitro, cyano, —S(=O)$_n$R$^e$, —OC$_{1-4}$haloalkyl, —OC$_{2-6}$alkylNR$^a$R$^f$, —OC$_{2-6}$alkylOR$^f$, —OC$_{1-6}$alkylC(=O)OR$^e$, —NR$^a$C$_{1-4}$haloalkyl, —NR$^a$C$_{2-6}$alkylNR$^a$R$^f$, —NR$^a$C$_{2-6}$alkylOR$^f$, —C(=O)R$^e$, —C(=O)OR$^e$, —OC(=O)R$^e$ and —C(=O)NR$^a$R$^f$; but in no instance is R$^4$ 3,5-ditrifluoromethylphenyl or 3-trifluoromethyl-4-fluorophenyl, -phenyl-(C$_{1-8}$alkyl), -phenyl-O—(C$_{1-6}$alkyl), -phenyl-NR$^a$R$^a$ or -phenyl-N(R$^a$)C(=O)(C$_{1-6}$alkyl);

R$^5$ is independently, at each instance, R$^f$, R$^g$, halo, nitro, cyano, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$ alkylOR$^f$, naphthyl, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$ alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OC(=O)NR$^a$R$^f$, a phenyl ring substituted with 0, 1, 2, or 3 substituents independently selected from R$^{10}$; or R$^5$ is a saturated or unsaturated 5- or 6-membered ring heterocycle containing 1, 2 or 3 atoms selected from O, N and S, substituted with 0, 1, 2, or 3 substituents independently selected from R$^{10}$;

R$^6$ is independently, at each instance, H, C$_{1-5}$alkyl, C$_{1-4}$haloalkyl, halo, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$haloalkyl, —NR$^a$C$_{2-6}$alkylNR$^a$R$^a$ or —NR$^a$C$_{2-6}$alkylOR$^a$, —C$_{1-8}$alkylOR$^a$, —C$_{1-6}$alkylNR$^a$R$^a$, —S(C$_{1-6}$alkyl), a phenyl ring substituted with 1, 2, or 3 substituents independently selected from R$^{10}$; or R$^6$ is a saturated or unsaturated 5- or 6-membered ring heterocycle containing 1, 2 or 3 atoms selected from O, N and S substituted with 0, 1, 2, or 3 substituents independently selected from R$^{10}$;

R$^7$ is independently, at each instance, H, acyclicC$_{1-8}$alkyl, C$_{1-4}$haloalkyl, halo, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —C$_{1-8}$alkylOR$^a$, —C$_{1-6}$alkylNR$^a$R$^a$ or —S(C$_{1-6}$alkyl); or R$^7$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl;

R$^8$ is independently, at each instance, H, C$_{1-5}$alkyl, C$_{1-4}$haloalkyl, halo, —OC$_{1-6}$alkyl, —OC$_{1-4}$haloalkyl, —OC$_{2-6}$alkylR$^a$R$^a$, —OC$_{2-6}$alkylOR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —C$_{1-8}$ alkylOR$^a$, —C$_{1-6}$alkylNR$^a$R$^a$, —S(C$_{1-6}$alkyl), a phenyl ring substituted with 1, 2, or 3 substituents independently selected from R$^{10}$, or R$^8$ is a saturated or unsaturated 5- or 6-membered ring heterocycle containing 1, 2 or 3 atoms selected from O, N and S substituted with 0, 1, 2, or 3 substituents independently selected from R$^{10}$;

R$^9$ is independently, at each instance, R$^f$, R$^g$, halo, nitro, cyano, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$ alkylOR$^f$, naphthyl, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$ alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OC(=O)NR$^a$R$^f$, a phenyl ring substituted with 0, 1, 2, or 3 substituents independently selected from R$^{10}$; or R$^9$ is a saturated or unsaturated 5- or 6-membered ring heterocycle containing 1, 2 or 3 atoms selected from O, N and S substituted with 0, 1, 2, or 3 substituents independently selected from R$^{10}$; or R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl; wherein at least one of R$^5$, R$^6$, R$^7$, R$^8$ and R$^9$ is C$_{1-8}$alkyl, C$_{1-4}$haloalkyl, halo, —OC$_{1-4}$haloalkyl, —OC$_{2-6}$ alkylNR$^a$R$^a$, —OC$_{2-6}$alkylOR$^a$, —NR$^a$C$_{1-4}$ haloalkyl, —NR$^a$C$_{2-6}$alkylNR$^a$R$^a$, —NR$^a$C$_{2-6}$alkylOR$^a$, —C$_{1-8}$alkylOR$^a$, —C$_{1-6}$alkylNR$^a$R$^a$ or —S(C$_{1-6}$alkyl);

R$^{10}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$ alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^{11}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{11}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{11}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ and R$^{11}$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$;

R$^{12}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$ alkylNR$^a$R$^a$, —OC$_{2-6}$alkylOR$^a$, SR$^a$, —S(=O)(C$_{1-8}$ alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$ alkylNR$^a$R$^a$ and —NR$^a$C$_{2-6}$alkylOR$^a$; or R$^{12}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$ alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{12}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; wherein if R$^{11}$ or R$^{13}$ is CF$_3$, then R$^{12}$ is not F; or R$^{11}$ and R$^{12}$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$; wherein when R$^3$ is NH$_2$, then —R$^{11}$—R$^{12}$— is not —C=C—C=N— or any substituted version thereof;

R$^{13}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$ alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{13}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl) —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{13}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$ alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl) —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^{14}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$ alkylNR$^a$R$^a$, —OC$_{2-6}$alkylOR$^a$, —SR$^a$, —S(=O)(C$_{1-8}$ alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{14}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{14}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$ alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$ alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; wherein at least one of R$^{10}$, R$^{11}$, R$^{12}$, R$^{13}$ and R$^{14}$ is other than H;

R$^a$ is independently, at each instance, H, phenyl, benzyl or C$_{1-6}$alkyl;

R$^b$ is a heterocycle selected from the group of thiophene, pyrrole, 1,3-oxazole, 1,3-thiazole, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, furan, imidazol-1-yl, imidazol-4-yl, 1,2,4-triazol-4-yl, 1,2,4-triazol-5-yl, isoxazol-3-yl, isoxazol-5-yl, pyrazol-3-yl, pyrazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazoline, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazole, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4] thidiazole, 2,5-dihydro-[1,2,4] thiadiazole, 4,5-dihydro-[1,2,4] thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4] thiadiazole, 2,3-dihydro-[1,2,4] thiadiazole, 4,5-dihydro-[1,2,4] thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2] thiazine, 3,6-dihydro-2H-[1,2] thiazine, 3,4-dihydro-2H-[1,2] thiazine, 5,6-dihydro-2H-[1,3]oxazine, 5,6-dihydro-4H-[1,3] oxazine, 3,6-dihydro-2H-[1,3]oxazine, 3,4-dihydro-2H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 4,5-dihydropyridine, 1,6-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 2,3-dihydropyrimidine, 2,5-dihydropyrimidine, 5,6-dihydropyrimidine, 3,6-dihydropyrimidine, 4,5-dihydropyrazine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine and 1,4,2-oxathiazine, wherein the heterocycle is optionally vicinally fused with a saturated or unsaturated 5-, 6- or 7-membered ring containing 0, 1 or 2 atoms independently selected from N, O and S;

R$^c$ is independently, in each instance, phenyl substituted by 0, 1 or 2 groups selected from halo, C$_{1-4}$alkyl, C$_{1-3}$haloalkyl, —OR$^a$ and —NR$^a$R$^a$; or R$^c$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, C$_{1-4}$alkyl, C$_{1-3}$haloalkyl, —OR$^a$ and —NR$^a$R$^a$;

R$^d$ is hydrogen or —CH$_3$;

R$^e$ is, independently, in each instance, C$_{1-9}$-alkyl substituted by 0, 1, 2, 3 or 4 substituents selected from halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and wherein the C$_{1-9}$alkyl is additionally substituted by 0 or 1 groups independently selected from R$^g$;

R$^f$ is, independently, in each instance, R$^e$ or H; and

R$^g$ is, independently, in each instance, a saturated or unsaturated 5- or 6-membered monocyclic ring containing 1, 2 or 3 atoms selected from N, O and S, so long as the combination of O and S atoms is not greater than 2, wherein the carbon atoms of the ring are substituted by 0 or 1 oxo groups.

In one embodiment, in conjunction with any one of the above and below embodiments, X is =N— or =C(R$^2$)—; Y is —N— or =C(R$^3$)—, wherein at least one of X and Y is not =N—.

In another embodiment, in conjunction with any one of the above and below embodiments, X is =C(R$^2$)—; Y is =C(R$^3$)—; and R$^3$ is halo, —NH$_2$, —NHC$_{1-3}$alkyl, —N(C$_{1-3}$ alkyl)C$_{1-3}$alkyl, or C$_{1-3}$alkyl.

In another embodiment, in conjunction with any one of the above and below embodiments, X is =C(R$^2$)—; Y is =C(R$^3$)—; and R$^3$ is H;

In another embodiment, in conjunction with any one of the above and below embodiments, X is =N—; and Y is =C(R$^3$)—.

In another embodiment, in conjunction with any one of the above and below embodiments, X is =C(R$^2$)—; and Y is =N—.

Sub-embodiment A: In another embodiment, in conjunction with any one of the above and below embodiments, R$^1$ is

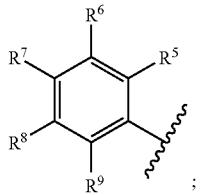

or R$^1$ is a naphthyl substituted by 0, 1, 2 or 3 substituents independently selected from R$^5$; or R$^1$ is R$^b$ substituted by 1, 2 or 3 substituents independently selected from R$^5$.

Sub-embodiment B: In another embodiment, in conjunction with any one of the above and below embodiments, R$^1$ is

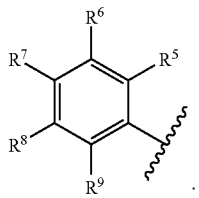

In another embodiment, in conjunction with any one of the above and below embodiments, R$^1$ is a naphthyl substituted by 0, 1, 2 or 3 substituents independently selected from R$^5$.

Sub-embodiment C: In another embodiment, in conjunction with any one of the above and below embodiments, R$^1$ is R$^b$ substituted by 1, 2 or 3 substituents independently selected from R$^5$.

In another embodiment, in conjunction with any one of the above and below embodiments, R$^2$ is, independently, in each instance, R$^{10}$, C$_{1-8}$alkyl substituted by 0, 1 or 2 substituents selected from R$^{10}$, —(CH$_2$)$_n$phenyl substituted by 0, 1, 2 or 3 substituents independently selected from R$^{10}$, or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from R$^{10}$.

In another embodiment, in conjunction with any one of the above and below embodiments, R$^2$ is, independently, in each instance, R$^{10}$, C$_{1-8}$alkyl substituted by 0, 1 or 2 substituents selected from R$^{10}$, —(CH$_2$)phenyl substituted by 0, 1, 2 or 3 substituents independently selected from R$^{10}$, or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from R$^{10}$.

In another embodiment, in conjunction with any one of the above and below embodiments, R$^2$ is C$_{1-8}$alkyl substituted by 0, 1 or 2 substituents selected from R$^{10}$.

In another embodiment, in conjunction with any one of the above and below embodiments, R$^2$ is —(CH$_2$)$_{1-2}$phenyl substituted by 0, 1, 2 or 3 substituents independently selected from R$^{10}$.

In another embodiment, in conjunction with any one of the above and below embodiments, R$^2$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from R$^{10}$.

In another embodiment, in conjunction with any one of the above and below embodiments, R$^2$ is H.

In another embodiment, in conjunction with any one of the above and below embodiments, R$^3$ is, independently, in each instance, H, halo, —NH$_2$, —NHC$_{1-3}$alkyl, —N(C$_{1-3}$alkyl)C$_{1-3}$alkyl, or C$_{1-3}$alkyl; wherein, when X is =C(R$^2$)— and Y is =C(R$^3$)— then at least one of R$^2$ and R$^3$ is other than H.

In another embodiment, in conjunction with any one of the above and below embodiments, R$^3$ is halo, —NH$_2$, —NHC$_{1-3}$alkyl, —N(C$_{1-3}$alkyl)C$_{1-3}$alkyl, or C$_{1-3}$alkyl.

In another embodiment, in conjunction with any one of the above and below embodiments, R$^3$ is H.

Sub-embodiment D: In another embodiment, in conjunction with any one of the above and below embodiments, R$^4$ is

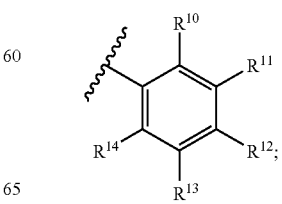

or $R^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from $R^e$, $C_{1-4}$haloalkyl, halo, nitro, cyano, oxo, —$OR^f$, —$S(=O)_nR^e$, —$OC_{1-4}$haloalkyl, —$OC_{2-6}$alkylNR$^a$R$^f$, —$OC_{2-6}$alkylOR$^f$, —$OC_{1-6}$alkylC(=O)OR$^e$, —$NR^aR^f$, —$NR^aC_{1-4}$haloalkyl, —$NR^aC_{2-6}$alkylNR$^a$R$^f$, —$NR^aC_{2-6}$alkylOR$^f$, —C(=O)$R^e$, —C(=O)OR$^e$, —OC(=O)$R^e$, —C(=O)NR$^a$R$^f$ and —NR$^a$C(=O)R$^e$; and unsaturated carbon atoms may be additionally substituted by =O; and any available nitrogen atoms in the heterocycle and bridge are substituted by H, —$C_{1-6}$alkylOR$^f$, $R^e$, —$C_{1-6}$alkylNR$^a$R$^f$, —$C_{1-3}$alkylC(=O)OR$^e$, —$C_{1-3}$alkylC(=O)NR$^a$R$^f$, —$C_{1-3}$alkylOC(=O)R$^e$, —$C_{1-3}$alkylNR$^a$C(=O)R$^e$, —C(=O)R$^c$ or —$C_{1-3}$alkylR$^c$; or $R^4$ is naphthyl substituted by 1, 2 or 3 substituents independently selected from $C_{1-4}$haloalkyl, halo, nitro, cyano, —S(=O)$_n$R$^e$, —$OC_{1-4}$haloalkyl, —$OC_{2-6}$alkylNR$^a$R$^f$, —$OC_{2-6}$alkylOR$^f$, —$OC_{1-6}$alkylC(=O)OR$^e$, —$NR^aC_{1-4}$haloalkyl, —$NR^aC_{2-6}$alkylNR$^a$R$^f$, —$NR^aC_{2-6}$alkylOR$^f$, —C(=O)R$^e$, —C(=O)OR$^e$, —OC(=O)R$^e$ and —C(=O)NR$^a$R$^f$; but in no instance is $R^4$ 3,5-ditrifluoromethylphenyl or 3-trifluoromethyl-4-fluorophenyl, -phenyl-($C_{1-8}$alkyl), -phenyl-O—($C_{1-6}$alkyl), -phenyl-NR$^a$R$^a$ or -phenyl-N(R$^a$)C(=O)($C_{1-8}$alkyl).

Sub-embodiment E: In another embodiment, in conjunction with any one of the above and below embodiments, $R^4$ is

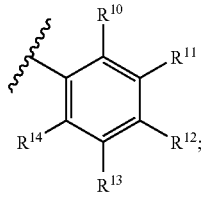

but in no instance is $R^4$ 3,5-ditrifluoromethylphenyl or 3-trifluoromethyl-4-fluorophenyl, -phenyl-($C_{1-8}$alkyl), -phenyl-O—($C_{1-6}$alkyl), -phenyl-NR$^a$R$^a$ or -phenyl-N(R$^a$)C(=O)($C_{1-8}$alkyl).

Sub-embodiment F: In another embodiment, in conjunction with any one of the above and below embodiments, $R^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from $R^e$, $C_{1-4}$haloalkyl, halo, nitro, cyano, oxo, —$OR^f$, —$S(=O)_nR^e$, —$OC_{1-4}$haloalkyl, —$OC_{2-6}$alkylNR$^a$R$^f$, —$OC_{2-6}$alkylOR$^f$, —$OC_{1-6}$alkylC(=O)OR$^e$, —$NR^aR^f$, —$NR^aC_{1-4}$haloalkyl, —$NR^aC_{2-6}$alkylNR$^a$R$^f$, —$NR^aC_{2-6}$alkylOR$^f$, —C(=O)R$^e$, —C(=O)OR$^e$, —OC(=O)R$^e$, —C(=O)NR$^a$R$^f$ and —NR$^a$C(=O)R$^e$; and unsaturated carbon atoms may be additionally substituted by =O; and any available nitrogen atoms in the heterocycle and bridge are substituted by H, —$C_{1-6}$alkylOR$^f$, $R^e$, —$C_{1-6}$alkylNR$^a$R$^f$, —$C_{1-3}$alkylC(=O)OR$^e$, —$C_{1-3}$alkylC(=O)NR$^a$R$^f$, —$C_{1-3}$alkylOC(=O)R$^e$, —$C_{1-3}$alkylNR$^a$C(=O)R$^e$, —C(=O)R$^c$ or —$C_{1-3}$alkylR$^c$.

Sub-embodiment G: In another embodiment, in conjunction with any one of the above and below embodiments, $R^4$ is a saturated or unsaturated 5- or 6-membered ring heterocycle containing 1, 2 or 3 atoms selected from O, N and S that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from $R^e$, $C_{1-4}$haloalkyl, halo, nitro, cyano, oxo, —$OR^f$, —S(=O)$_n$R$^e$, —$OC_{1-4}$haloalkyl, —$OC_{2-6}$alkylNR$^a$R$^f$, —$OC_{2-6}$alkylOR$^f$, —$OC_{1-6}$alkylC(=O)OR$^e$, —$NR^aR^f$, —$NR^aC_{1-4}$haloalkyl, —$NR^aC_{2-6}$alkylNR$^a$R$^f$, —$NR^aC_{2-6}$alkylOR$^f$, —C(=O)R$^e$, —C(=O)OR$^e$, —OC(=O)R$^e$, —C(=O)NR$^a$R$^f$ and —NR$^a$C(=O)R$^e$; and unsaturated carbon atoms may be additionally substituted by =O; and any available nitrogen atoms in the heterocycle and bridge are substituted by H, —$C_{1-6}$alkylOR$^f$, $R^e$, —$C_{1-6}$alkylNR$^a$R$^f$, —$C_{1-3}$alkylC(=O)OR$^e$, —$C_{1-3}$alkylC(=O)NR$^a$R$^f$, —$C_{1-3}$alkylOC(=O)R$^e$, —$C_{1-3}$alkylNR$^a$C(=O)R$^e$, —C(=O)R$^c$ or —$C_{1-3}$alkylR$^c$.

In another embodiment, in conjunction with any one of the above and below embodiments, $R^4$ is naphthyl substituted by 1, 2 or 3 substituents independently selected from $C_{1-4}$haloalkyl, halo, nitro, cyano, —S(O)$_n$R$^e$, —$OC_{1-4}$haloalkyl, —$OC_{2-6}$alkylNR$^a$R$^f$, —$OC_{2-6}$alkylOR$^f$, —$OC_{1-6}$alkylC(=O)OR$^e$, —$NR^aC_{1-4}$haloalkyl, —$NR^aC_{2-6}$alkylNR$^a$R$^f$, —$NR^aC_{2-6}$alkylOR$^f$, —C(=O)R$^e$, —C(=O)OR$^e$, —OC(=O)R$^e$ and —C(=O)NR$^a$R$^f$.

In another embodiment, in conjunction with any one of the above and below embodiments, $R^5$ is independently, at each instance, $R^f$, $R^g$, halo, nitro, cyano, —OR$^e$, —OR$^g$, —$OC_{2-6}$alkylNR$^a$R$^f$, —$OC_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —$C_{1-8}$alkylOR$^f$, —$C_{1-6}$alkylNR$^a$R$^f$, —S(=O)$_n$R$^e$, —S(=O)$_2$NR$^a$R$^f$, —NR$^a$S(=O)$_2$R$^e$, —OC(=O)NR$^a$R$^f$, a phenyl ring substituted with 0, 1, 2, or 3 substituents independently selected from R$^{10}$; or $R^5$ is a saturated or unsaturated 5- or 6-membered ring heterocycle containing 1, 2 or 3 atoms selected from O, N and S, substituted with 0, 1, 2, or 3 substituents independently selected from R$^{10}$.

In another embodiment, in conjunction with any one of the above and below embodiments, $R^5$ is H.

In another embodiment, in conjunction with any one of the above and below embodiments, $R^5$ is $R^f$ or $R^g$.

In another embodiment, in conjunction with any one of the above and below embodiments, $R^5$ is independently, at each instance, $R^e$, $R^g$, halo, nitro, cyano, —OR$^e$, —OR$^g$, —$OC_{2-6}$alkylNR$^a$R$^f$, —$OC_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —$C_{1-8}$alkylOR$^f$, —$C_{1-6}$alkylNR$^a$R$^f$, —S(=O)$_n$R$^e$, —S(=O)$_2$NR$^a$R$^f$, —NR$^a$S(=O)$_2$R$^e$, —OC(=O)NR$^a$R$^f$, a phenyl ring substituted with 0, 1, 2, or 3 substituents independently selected from R$^{10}$; or $R^5$ is a saturated or unsaturated 5- or 6-membered ring heterocycle containing 1, 2 or 3 atoms selected from O, N and S, substituted with 0, 1, 2, or 3 substituents independently selected from R$^{10}$.

In another embodiment, in conjunction with any one of the above and below embodiments, $R^6$ is independently, at each instance, H, $C_{1-5}$alkyl, $C_{1-4}$haloalkyl, halo, —$OC_{1-6}$alkyl, —$OC_{1-4}$haloalkyl, —$OC_{2-6}$alkylNR$^a$R$^a$, —$OC_{2-6}$alkylOR$^a$, —NR$^a$R$^a$, —NR$^a$C$_{1-4}$haloalkyl, —NR$^a$C$_{2-6}$alkylNR$^a$R$^a$ or —NR$^a$C$_{2-6}$alkylOR$^a$, —$C_{1-8}$alkylOR$^a$, —$C_{1-6}$alkylNR$^a$R$^a$, —S($C_{1-6}$alkyl), a phenyl ring substituted with 1, 2, or 3 substituents independently selected from $R^{10}$; or $R^6$ is a saturated or unsaturated 5- or 6-membered ring heterocycle containing 1, 2 or 3 atoms selected from O, N and S substituted with 0, 1, 2, or 3 substituents independently selected from $R^{10}$.

In another embodiment, in conjunction with any one of the above and below embodiments, $R^6$ is independently, at each instance, $C_{1-5}$alkyl, $C_{1-4}$haloalkyl, halo, —$OC_{1-6}$alkyl, —$OC_{1-4}$haloalkyl, —$OC_{2-6}$alkylNR$^a$R$^a$, —$OC_{2-6}$alkylOR$^a$, —NR$^a$R$^a$, —NR$^a$C$_{1-4}$haloalkyl, —NR$^a$C$_{2-6}$alkylNR$^a$R$^a$ or —NR$^a$C$_{2-6}$alkylOR$^a$, —$C_{1-8}$alkylOR$^a$, —$C_{1-6}$alkylNR$^a$R$^a$, —S($C_{1-6}$alkyl), a phenyl ring substituted with 1, 2, or 3 substituents independently selected from $R^{10}$; or $R^6$ is a saturated or unsaturated 5- or 6-membered ring heterocycle containing 1, 2 or 3 atoms selected from O, N and S substituted with 0, 1, 2, or 3 substituents independently selected from $R^{10}$.

In another embodiment, in conjunction with any one of the above and below embodiments, $R^6$ is independently, at each instance, $C_{1-5}$alkyl, $C_{1-4}$haloalkyl, halo, —$OC_{1-6}$alkyl, —$OC_{1-4}$haloalkyl, —$OC_{2-6}$alkylNR$^a$R$^a$, —$OC_{2-6}$alkylOR$^a$, NR$^a$R$^a$, —NR$^a$C$_{1-4}$haloalkyl, —NR$^a$C$_{2-6}$alkylNR$^a$R$^a$ or —NR$^a$C$_{2-6}$alkylOR$^a$, —$C_{1-8}$alkylOR$^a$, —$C_{1-6}$alkylNR$^a$R$^a$ or —S($C_{1-6}$alkyl).

In another embodiment, in conjunction with any one of the above and below embodiments, $R^6$ is a phenyl ring substituted with 1, 2, or 3 substituents independently selected from $R^{10}$.

In another embodiment, in conjunction with any one of the above and below embodiments, $R^6$ is a saturated or unsaturated 5- or 6-membered ring heterocycle containing 1, 2 or 3 atoms selected from O, N and S substituted with 0, 1, 2, or 3 substituents independently selected from $R^{10}$.

In another embodiment, in conjunction with any one of the above and below embodiments, $R^6$ is H.

In another embodiment, in conjunction with any one of the above and below embodiments, $R^7$ is independently, at each instance, H, acyclic$C_{1-8}$alkyl, $C_{1-4}$haloalkyl, halo, —$OC_{1-6}$alkyl, —$OC_{1-4}$haloalkyl, —$OC_{2-6}$alkylNR$^a$R$^a$, —$OC_{2-6}$alkylOR$^a$, —NR$^a$R$^a$, —NR$^a$C$_{1-4}$haloalkyl, —NR$^a$C$_2$alkylNR$^a$R$^a$, —NR$^a$C$_{2-6}$alkylOR$^a$, —$C_{1-8}$alkylOR$^a$, —$C_{1-6}$alkylNR$^a$R$^a$ or —S($C_{1-6}$alkyl); or $R^7$ is a saturated or unsaturated 4- or 5-membered ring heterocycle containing a single nitrogen atom, wherein the ring is substituted with 0, 1 or 2 substituents independently selected from halo, $C_{1-2}$haloalkyl and $C_{1-3}$alkyl.

Sub-embodiment H: In another embodiment, in conjunction with any one of the above and below embodiments, $R^7$ is independently, at each instance, acyclic$C_{1-8}$alkyl, $C_{1-4}$haloalkyl, halo, —$OC_{1-6}$alkyl, —$OC_{1-4}$haloalkyl, —$OC_{2-6}$alkylNR$^a$R$^a$, —$OC_{2-6}$alkylOR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —$C_{1-8}$alkylOR$^a$, —$C_{1-6}$alkylNR$^a$R$^a$ or —S($C_{1-6}$alkyl); or $R^7$ is a saturated or unsaturated 4- or 5-membered ring heterocycle containing a single nitrogen atom, wherein the ring is substituted with 0, 1 or 2 substituents independently selected from halo, $C_{1-2}$haloalkyl and $C_{1-3}$alkyl.

In another embodiment, in conjunction with any one of the above and below embodiments, $R^7$ is H.

In another embodiment, in conjunction with any one of the above and below embodiments, $R^7$ is a saturated or unsaturated 4- or 5-membered ring heterocycle containing a single nitrogen atom, wherein the ring is substituted with 0, 1 or 2 substituents independently selected from halo, $C_{1-2}$haloalkyl and $C_{1-3}$alkyl.

In another embodiment, in conjunction with any one of the above and below embodiments, $R^7$ is independently, at each instance, acyclic$C_{1-8}$alkyl, $C_{1-4}$haloalkyl, halo, —$OC_{1-6}$alkyl, —$OC_{1-4}$haloalkyl, —$OC_{2-6}$alkylNR$^a$R$^a$, —$OC_{2-6}$alkylOR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —$C_{1-8}$alkylOR$^a$, —$C_{1-6}$alkylNR$^a$R$^a$ or —S($C_{1-6}$alkyl).

In another embodiment, in conjunction with any one of the above and below embodiments, $R^7$ is independently, at each instance, acyclic$C_{1-8}$alkyl, $C_{1-4}$haloalkyl, Br, or Cl.

In another embodiment, in conjunction with any one of the above and below embodiments, $R^7$ is independently, at each instance, acyclic$C_{1-8}$alkyl or $C_{1-4}$haloalkyl.

Sub-embodiment I: In another embodiment, in conjunction with any one of the above and below embodiments, $R^7$ is independently, at each instance, $C_{3-5}$alkyl or $C_{1-2}$haloalkyl.

In another embodiment, in conjunction with any one of the above and below embodiments, $R^7$ is $C_{3-5}$alkyl.

In another embodiment, in conjunction with any one of the above and below embodiments, $R^7$ is —C(CH$_3$)$_3$.

In another embodiment, in conjunction with any one of the above and below embodiments, $R^7$ is —CF$_3$.

In another embodiment, in conjunction with any one of the above and below embodiments, $R^8$ is independently, at each instance, H, $C_{1-5}$alkyl, $C_{1-4}$haloalkyl, halo, —$OC_{1-6}$alkyl, —$OC_{1-4}$haloalkyl, —$OC_{2-6}$alkylNR$^a$R$^a$, —$OC_{2-6}$alkylOR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —$C_{1-8}$alkylOR$^a$, —$C_{1-6}$alkylNR$^a$R$^a$, —S($C_{1-6}$alkyl), a phenyl ring substituted with 1, 2, or 3 substituents independently selected from $R^{10}$, or $R^8$ is a saturated or unsaturated 5- or 6-membered ring heterocycle containing 1, 2 or 3 atoms selected from O, N and S substituted with 0, 1, 2, or 3 substituents independently selected from $R^{10}$.

In another embodiment, in conjunction with any one of the above and below embodiments, $R^8$ is H.

In another embodiment, in conjunction with any one of the above and below embodiments, $R^8$ is independently, at each instance, $C_{1-5}$alkyl, $C_{1-4}$haloalkyl, halo, —$OC_{1-6}$alkyl, —$OC_{1-4}$haloalkyl, —$OC_{2-6}$alkylNR$^a$R$^a$, —$OC_{2-6}$alkylOR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —$C_{1-8}$alkylOR$^a$, —$C_{1-6}$alkylNR$^a$R$^a$, —S($C_{1-6}$alkyl), a phenyl ring substituted with 1, 2, or 3 substituents independently selected from $R^{10}$, or $R^8$ is a saturated or unsaturated 5- or 6-membered ring heterocycle containing 1, 2 or 3 atoms selected from O, N and S substituted with 0, 1, 2, or 3 substituents independently selected from $R^{10}$.

In another embodiment, in conjunction with any one of the above and below embodiments, $R^8$ is independently, at each instance, $C_{1-5}$alkyl, $C_{1-4}$haloalkyl, halo, —$OC_{1-6}$alkyl, —$OC_{1-4}$haloalkyl, —$OC_{2-6}$alkylNR$^a$R$^a$, —$OC_{2-6}$alkylOR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —$C_{1-8}$alkylOR$^a$, —$C_{1-6}$alkylNR$^a$R$^a$ or —S($C_{1-6}$alkyl).

In another embodiment, in conjunction with any one of the above and below embodiments, $R^8$ is a phenyl ring substituted with 1, 2, or 3 substituents independently selected from $R^{10}$.

In another embodiment, in conjunction with any one of the above and below embodiments, $R^8$ is a saturated or unsaturated 5- or 6-membered ring heterocycle containing 1, 2 or 3 atoms selected from O, N and S substituted with 0, 1, 2, or 3 substituents independently selected from $R^{10}$.

Sub-embodiment J: In another embodiment, in conjunction with any one of the above and below embodiments, $R^9$ is independently, at each instance, $R^f$, $R^g$, halo, nitro, cyano, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OC(=O)NR$^a$R$^f$, a phenyl ring substituted with 0, 1, 2, or 3 substituents independently selected from R$^{10}$; or R$^9$ is a saturated or unsaturated 5- or 6-membered ring heterocycle containing 1, 2 or 3 atoms selected from O, N and S substituted with 0, 1, 2, or 3 substituents independently selected from R$^{10}$; wherein at least one of R$^5$, R$^6$, R$^7$, R$^8$ and R$^9$ is C$_{1-8}$alkyl, C$_{1-4}$haloalkyl, halo, —OC$_{1-4}$haloalkyl, —OC$_{2-6}$alkylNR$^a$R$^a$, —OC$_{2-6}$alkylOR$^a$, —NR$^a$C$_{1-4}$haloalkyl, —NR$^a$C$_{2-6}$alkylNR$^a$R$^a$, —NR$^a$C$_{2-6}$alkylOR$^a$, —C$_{1-8}$alkylOR$^a$, —C$_{1-6}$alkylNR$^a$R$^a$ or —S(C$_{1-6}$alkyl); or R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl.

Sub-embodiment K: In another embodiment, in conjunction with any one of the above and below embodiments, R$^9$ is H.

Sub-embodiment L: In another embodiment, in conjunction with any one of the above and below embodiments, R$^9$ is independently, at each instance, R$^e$, R$^g$, halo, nitro, cyano, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OC(=O)NR$^a$R$^f$, a phenyl ring substituted with 0, 1, 2, or 3 substituents independently selected from R$^{10}$; or R$^9$ is a saturated or unsaturated 5- or 6-membered ring heterocycle containing 1, 2 or 3 atoms selected from O, N and S substituted with 0, 1, 2, or 3 substituents independently selected from R$^{10}$; wherein at least one of R$^5$, R$^6$, R$^7$, R$^8$ and R$^9$ is C$_{1-8}$alkyl, C$_{1-4}$haloalkyl, halo, —OC$_{1-4}$haloalkyl, —OC$_{2-6}$alkylNR$^a$R$^a$, —OC$_{2-6}$alkylOR$^a$, —NR$^a$C$_{1-4}$haloalkyl, —NR$^a$C$_{2-6}$alkylNR$^a$R$^a$, —NR$^a$C$_{2-6}$alkylOR$^a$, —C$_{1-8}$alkylOR$^a$, —C$_{1-6}$alkylNR$^a$R$^a$ or —S(C$_{1-6}$alkyl); or R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl.

In another embodiment, in conjunction with any one of the above and below embodiments, R$^9$ is independently, at each instance, R$^e$.

In another embodiment, in conjunction with any one of the above and below embodiments, R$^9$ is independently, at each instance, R$^g$.

In another embodiment, in conjunction with any one of the above and below embodiments, R$^9$ is independently, at each instance, halo, nitro, cyano, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$ or —OC(=O)NR$^a$R$^f$.

In another embodiment, in conjunction with any one of the above and below embodiments, R$^9$ is independently, at each instance, a phenyl ring substituted with 0, 1, 2, or 3 substituents independently selected from R$^{10}$; or R$^9$ is a saturated or unsaturated 5- or 6-membered ring heterocycle containing 1, 2 or 3 atoms selected from O, N and S substituted with 0, 1, 2, or 3 substituents independently selected from R$^{10}$.

In another embodiment, in conjunction with any one of the above and below embodiments, R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl.

In another embodiment, in conjunction with any one of the above and below embodiments, R$^{10}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl) —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —C$_{2-6}$alkylOR$^a$, SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

Sub-embodiment M: In another embodiment, in conjunction with any one of the above and below embodiments, R$^{10}$ is H.

In another embodiment, in conjunction with any one of the above and below embodiments, R$^{10}$ is independently, at each instance, selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N (R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O (C$_{1-8}$alkyl), —N(R$^a$)C(=O)NR$^a$R$^a$, —N(R$^a$)C(=NR$^a$) NR$^a$R$^a$, —N(R$^a$)S(=O)$_2$(C$_{1-8}$alkyl), —N(R$^a$)S(=O)$_2$ NR$^a$R$^a$, —NR$^a$C$_{2-6}$alkylNR$^a$R$^a$ and —NR$^a$C$_{2-6}$alkylOR$^a$; or R$^{10}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O) NR$^a$R$^a$, —C(=NR$^a$)NR$^a$R$^a$, —OR$^a$, —OC(=O)(C$_{1-8}$ alkyl), —OC(=O)NR$^a$R$^a$, —OC(=O)N(R$^a$)S(=O)$_2$(C$_{1-8}$ alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$ NR$^a$R$^a$, —S(=O)$_2$N(R$^a$)C(=O)(C$_{1-8}$alkyl), —S(=O)$_2$N (R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O (C$_{1-8}$alkyl), —N(R$^a$)C(=O)NR$^a$R$^a$, N(R$^a$)C(=NR$^a$) NR$^a$R$^a$, —N(R$^a$)S(=O)$_2$(C$_{1-8}$alkyl), —N(R$^a$)S(=O)$_2$ NR$^a$R$^a$ and —NR$^a$C$_{2-6}$alkylOR$^a$; or R$^{10}$ is C$_{1-4}$alkyl substituted by 0, 1 or 2 groups selected from C$_{1-4}$haloalkyl, halo, cyano, nitro, —C(=O)(C$_{1-8}$alkyl), —C(=O)O(C$_{1-8}$ alkyl), —C(=O)NR$^a$R$^a$, —C(=NR$^a$)NR$^a$R$^a$, —OR$^a$, —OC(=O) (C$_{1-8}$alkyl), —OC(=O)NR$^a$R$^a$, —OC(=O)N(R$^a$)S(=O)$_2$ (C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$ NR$^a$R$^a$, —S(=O)$_2$N(R$^a$)C(=O)(C$_{1-8}$alkyl), —S(=O)$_2$N (R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O (C$_{1-8}$alkyl), —N(R$^a$)C(=O)NR$^a$R$^a$, N(R$^a$)C(=NR$^a$) NR$^a$R$^a$, —N(R$^a$)S(=O)$_2$(C$_{1-8}$alkyl), —N(R$^a$)S(=O)$_2$ NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^{11}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O) (C$_{1-8}$alkyl), —OC(=O)NR$^a$R$^a$, —OC(=O)N(R$^a$)S(=O)$_2$ (C$_{1-8}$alkyl), —OC$_{2-6}$alkyNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$ NR$^a$R$^a$, —S(=O)$_2$N(R$^a$)C(=O)(C$_{1-8}$alkyl), —S(=O)$_2$N (R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O (C$_{1-8}$alkyl), —N(R$^a$)C(=O)NR$^a$R$^a$, N(R$^a$)C(=NR$^a$) NR$^a$R$^a$, —N(R$^a$)S(=O)$_2$(C$_{1-8}$alkyl), —N(R$^a$)S(=O)$_2$ NR$^a$R$^a$, —NR$^a$C$_{2-6}$alkylNR$^a$R$^a$ and —NR$^a$C$_{2-6}$alkylOR$^a$; or R$^{11}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O) NR$^a$R$^a$, —C(=NR$^a$)NR$^a$R$^a$, —OR$^a$, —OC(=O)(C$_{1-8}$ alkyl), —OC(=O)NR$^a$R$^a$, —OC(=O)N(R$^a$)S(=O)$_2$(C$_{1-8}$ alkyl), —OC$_{2-6}$alkylNR$^a$R$^a$, —OC$_2$ alkyl), —SR$^a$, —S(=O)(C$_{1-8}$alkyl), —S(=O)$_2$(C$_{1-8}$alkyl), —S(=O)$_2$ NR$^a$R$^a$, —S(=O)$_2$N(R$^a$)C(=O)(C$_{1-8}$alkyl), —S(=O)$_2$N (R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O (C$_{1-8}$alkyl), —N(R$^a$)C(=O)NR$^a$R$^a$, N(R$^a$)C(=NR$^a$) NR$^a$R$^a$, —N(R$^a$)S(=O)$_2$(C$_{1-8}$alkyl), —N(R$^a$)S(=O)$_2$ NR$^a$R$^a$, —NR$^a$C$_{2-6}$alkylNR$^a$R$^a$ and —NR$^a$ C$_{2-6}$alkylOR$^a$; or R$^{11}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$) NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$ (C$_{1-8}$alkyl), —S(=O)$_2$NR$^a$R$^a$, —S(=O)$_2$N(R$^a$)C(=O) (C$_{1-8}$ alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O) (C$_{1-8}$alkyl), —N(R$^a$)C(=O)O(C$_{1-8}$alkyl), —N(R$^a$)C(=O) NR$^a$R$^a$, N(R$^a$)C(=NR$^a$)NR$^a$R$^a$, —N(R$^a$)S(=O)$_2$(C$_{1-8}$ alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ and R$^{11}$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from =O, R$^e$, halo, cyano, nitro, —C(=O)R$^e$, —C(=O)OR$^e$, —C(=O)NR$^e$R$^f$, —C(=NR$^a$) NR$^e$R$^f$, —OR$^f$, —OC(=O)R$^e$, —OC(=O)NR$^e$R$^f$, —OC (=O)N(R$^f$)S(=O)$_2$R$^e$, —OC$_{2-6}$alkylNR$^e$R$^f$, —OC$_{2-6}$alkylOR$^f$, —SR$^f$, —S(=O)R$^e$, —S(=O)$_2$R$^e$, —S(=O)$_2$NR$^e$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^e$R$^f$, —NR$^e$R$^f$, —N(R$^f$)C(=O) R$^e$, —N(R$^f$)C(=O)OR$^e$, —N(R$^f$)C(=O)NR$^e$R$^f$, —N(R$^f$)C (=NR$^a$)NR$^e$R$^f$, —N(R$^f$)S(=O)$_2$R$^e$, —N(R$^f$)S(=O)$_2$ NR$^e$R$^f$, —NR$^f$C$_{2-6}$alkylNR$^e$R$^f$ and —NR$^f$C$_{2-6}$alkylOR$^f$.

In another embodiment, in conjunction with any one of the above and below embodiments, R$^{11}$ is independently, at each instance, selected from C$_{1-8}$alkyl, cyano, nitro, —C(=O) (C$_{1-8}$ alkyl), —C(=O)O(C$_{1-8}$alkyl), —C(=O)NR$^a$R$^a$, —C(=NR$^a$)NR$^a$R$^a$, —OC(=O)(C$_{1-8}$alkyl), —OC(=O) NR$^a$R$^a$, —OC(=O)N(R$^a$)S(=O)$_2$(C$_{1-8}$alkyl), —OC$_{2-6}$ alkylNR$^a$R$^a$, —OC$_{2-6}$alkylOR$^a$, —SR$^a$, —S(=O)(C$_{1-8}$ alkyl), —S(=O)$_2$(C$_{1-8}$alkyl), —S(=O)$_2$NR$^a$R$^a$, —S(=O)$_2$ N(R$^a$)C(=O)(C$_{1-8}$alkyl), —S(=O)$_2$N(R$^a$)C(=O)O(C$_{1-8}$ alkyl), —S(=O)$_2$N(R$^a$)C(=O)NR$^a$R$^a$, —NR$^a$R$^a$, —N(R$^a$) C(=O)(C$_{1-8}$alkyl), —N(R$^a$)C(=O)O(C$_{1-8}$alkyl), —N(R$^a$)C (=O)NR$^a$R$^a$, —N(R$^a$)C(=NR$^a$)NR$^a$R$^a$, —N(R$^a$)S(=O)$_2$ (C$_{1-8}$alkyl), —N(R$^a$)S(=O)$_2$NR$^a$R$^a$, —NR$^a$C$_{2-6}$ alkylNR$^a$R$^a$ and —NR$^a$C$_{2-6}$alkylOR$^a$; or R$^{11}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$) NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$ (C$_{1-8}$alkyl), —S(=O)$_2$NR$^a$R$^a$, —S(=O)$_2$N(R$^a$)C(=O) (C$_{1-8}$ alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O) (C$_{1-8}$alkyl), —N(R$^a$)C(=O)O(C$_{1-8}$alkyl), —N(R$^a$)C(=O) NR$^a$R$^a$, —N(R$^a$)C(=NR$^a$)NR$^a$R$^a$, —N(R$^a$)S(=O)$_2$(C$_{1-8}$ alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{11}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)

$NR^aR^a$, $-C(=NR^a)NR^aR^a$, $-OR^a$, $-OC(=O)(C_{1-8}$alkyl), $-OC(=O)NR^aR^a$, $-OC(=O)N(R^a)S(=O)_2(C_{1-8}$alkyl), $-OC_{2-6}$alkylNR$^a$R$^a$, $-OC_{2-6}$alkylOR$^a$, $-SR^a$, $-S(=O)(C_{1-8}$alkyl), $-S(=O)_2(C_{1-8}$alkyl), $-S(=O)_2NR^aR^a$, $-S(=O)_2N(R^a)C(=O)(C_{1-8}$alkyl), $-S(=O)_2N(R^a)C(=O)O(C_{1-8}$alkyl), $-S(=O)_2N(R^a)C(=O)NR^aR^a$, $-NR^aR^a$, $-N(R^a)C(=O)(C_{1-8}$alkyl), $-N(R^a)C(=O)O(C_{1-8}$alkyl), $-N(R^a)C(=O)NR^aR^a$, $-N(R^a)C(=NR^a)NR^aR^a$, $-N(R^a)S(=O)_2(C_{1-8}$alkyl), $-N(R^a)S(=O)_2NR^aR^a$, $-NR^aC_{2-6}$alkylNR$^a$R$^a$ and $-NR^aC_{2-6}$alkylOR$^a$; or $R^{10}$ and $R^{11}$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from $=O$, $R^e$, halo, cyano, nitro, $-C(=O)R^e$, $-C(=O)OR^e$, $-C(=O)NR^aR^f$, $-C(=NR^a)NR^aR^f$, $-OR^f$, $-OC(=O)R^e$, $-OC(=O)NR^aR^f$, $-OC(=O)N(R^f)S(=O)_2R^e$, $-OC_{2-6}$alkylNR$^a$R$^f$, $-OC_{2-6}$alkylR$^f$, $-SR^f$, $-S(=O)R^e$, $-S(=O)_2R^e$, $-S(=O)_2NR^aR^f$, $-S(=O)_2N(R^f)C(=O)R^e$, $-S(=O)_2N(R^f)C(=O)OR^e$, $-S(=O)_2N(R^f)C(=O)NR^aR^f$, $-NR^aR^f$, $-N(R^f)C(=O)R^e$, $-N(R^f)C(=O)OR^e$, $-N(R^f)C(=O)NR^aR^f$, $-N(R^f)C(=NR^a)NR^aR^f$, $-N(R^f)S(=O)_2R^e$, $-N(R^f)S(=O)_2NR^aR^f$, $-NR^fC_{2-6}$alkylNR$^a$R$^f$ and $-NR^fC_{2-6}$alkylOR$^f$.

In another embodiment, in conjunction with any one of the above and below embodiments, $R^{11}$ is independently, at each instance, selected from $C_{1-8}$alkyl, cyano, nitro, $-C(=O)(C_{1-8}$alkyl), $-C(=O)O(C_{1-8}$alkyl), $-C(=O)NR^aR^a$, $-C(=NR^a)NR^aR^a$, $-OC(=O)(C_{1-8}$alkyl), $-OC(=O)NR^aR^a$, $-OC(=O)N(R^a)S(=O)_2(C_{1-8}$alkyl), $-OC_{2-6}$alkylNR$^a$R$^a$, $-OC_{2-6}$alkylOR$^a$, $-SR^a$, $-S(=O)(C_{1-8}$alkyl), $-S(=O)_2(C_{1-8}$alkyl), $-S(=O)_2NR^aR^a$, $-S(=O)_2N(R^a)C(=O)(C_{1-8}$alkyl), $-S(=O)_2N(R^a)C(=O)O(C_{1-8}$alkyl), $-S(=O)_2N(R^a)C(=O)NR^aR^a$, $-NR^aR^a$, $-N(R^a)C(=O)(C_{1-8}$alkyl), $-N(R^a)C(=O)O(C_{1-8}$alkyl), $-N(R^a)C(=O)NR^aR^a$, $-N(R^a)C(=NR^a)NR^aR^a$, $-N(R^a)S(=O)_2(C_{1-8}$alkyl), $-N(R^a)S(=O)_2NR^aR^a$, $-NR^aC_{2-6}$alkylNR$^a$R$^a$ and $-NR^aC_{2-6}$alkylOR$^a$.

In another embodiment, in conjunction with any one of the above and below embodiments, $R^{11}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, $-C(=O)(C_{1-8}$alkyl), $-C(=O)O(C_{1-8}$alkyl), $-C(=O)NR^aR^a$, $-C(=NR^a)NR^aR^a$, $-OR^a$, $-OC(=O)(C_{1-8}$alkyl), $-OC(=O)NR^aR^a$, $-OC(=O)N(R^a)S(=O)_2(C_{1-8}$alkyl), $-OC_{2-6}$alkylNR$^a$R$^a$, $-OC_{2-6}$alkylOR$^a$, $-SR^a$, $-S(=O)(C_{1-8}$alkyl), $-S(=O)_2(C_{1-8}$alkyl), $-S(=O)_2NR^aR^a$, $-S(=O)_2N(R^a)C(=O)(C_{1-8}$alkyl), $-S(=O)_2N(R^a)C(O)O(C_{1-8}$alkyl), $-S(=O)_2N(R^a)C(=O)NR^aR^a$, $-NR^aR^a$, $-N(R^a)C(=O)(C_{1-8}$alkyl), $-N(R^a)C(=O)O(C_{1-8}$alkyl), $-N(R^a)C(=O)NR^aR^a$, $-N(R^a)C(=NR^a)NR^aR^a$, $-N(R^a)S(=O)_2(C_{1-8}$alkyl), $-N(R^a)S(=O)_2NR^aR^a$, $-NR^aC_{2-6}$alkylNR$^a$R$^a$ and $-NR^aC_{2-6}$alkylOR$^a$.

In another embodiment, in conjunction with any one of the above and below embodiments, $R^{11}$ is $C_{1-4}$alkyl substituted by 0, 1, 2 or 3 groups selected from $C_{1-4}$haloalkyl, halo, cyano, nitro, $-C(=O)(C_{1-8}$alkyl), $-C(=O)O(C_{1-8}$alkyl), $-C(=O)NR^aR^a$, $-C(NR^a)NR^aR^a$, $-OR^a$, $-OC(=O)(C_{1-8}$alkyl), $-OC(=O)NR^aR^a$, $-OC(=O)N(R^a)S(=O)_2(C_{1-8}$alkyl), $-OC_{2-6}$alkylNR$^a$R$^a$, $-OC_{2-6}$alkylOR$^a$, $-SR^a$, $-S(=O)(C_{1-8}$alkyl), $-S(=O)_2(C_{1-8}$alkyl), $-S(=O)_2NR^aR^a$, $-S(=O)_2N(R^a)C(=O)(C_{1-8}$alkyl), $-S(=O)_2N(R^a)C(=O)O(C_{1-8}$alkyl), $-S(=O)_2N(R^a)C(=O)NR^aR^a$, $-NR^aR^a$, $-N(R^a)C(=O)(C_{1-8}$alkyl), $-N(R^a)C(=O)O(C_{1-8}$alkyl), $-N(R^a)C(=O)NR^aR^a$, $-N(R^a)C(=NR^a)NR^aR^a$, $-N(R^a)S(=O)_2(C_{1-8}$alkyl), $-N(R^a)S(=O)_2NR^aR^a$, $-NR^aC_{2-6}$alkylNR$^a$R$^a$ and $-NR^aC_{2-6}$alkylOR$^a$.

Sub-embodiment N: In another embodiment, in conjunction with any one of the above and below embodiments, $R^{10}$ and $R^{11}$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from $=O$, $R^e$, halo, cyano, nitro, $-C(=O)R^e$, $-C(=O)OR^e$, $-C(=O)NR^aR^f$, $-C(=NR^a)NR^aR^f$, $-OR^f$, $-OC(=O)R^e$, $-OC(=O)NR^aR^f$, $-OC(=O)N(R^f)S(=O)_2R^e$, $-OC_{2-6}$alkylNR$^a$R$^f$, $-OC_{2-6}$alkylOR$^f$, $-SR^f$, $-S(=O)R^e$, $-S(=O)_2R^e$, $-S(=O)_2NR^aR^f$, $-S(=O)_2N(R^f)C(=O)R^e$, $-S(=O)_2N(R^f)C(=O)OR^e$, $-S(=O)_2N(R^f)C(=O)NR^aR^f$, $-NR^aR^f$, $-N(R^f)C(=O)R^e$, $-N(R^f)C(=O)OR^e$, $-N(R^f)C(=O)NR^aR^f$, $-N(R^f)C(=NR^a)NR^aR^f$, $-N(R^f)S(=O)_2R^e$, $-N(R^f)S(=O)_2NR^aR^f$, $-NR^fC_{2-6}$alkylNR$^a$R$^f$ and $-NR^fC_{2-6}$alkylOR$^f$.

In another embodiment, in conjunction with any one of the above and below embodiments, $R^{10}$ and $R^{11}$ together are a saturated or unsaturated 3-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from $=O$, $R^e$, halo, cyano, nitro, $-C(=O)R^e$, $-C(=O)OR^e$, $-C(=O)NR^aR^f$, $-C(=NR^a)NR^aR^f$, $-OR^f$, $-OC(=O)R^e$, $-OC(=O)NR^aR^f$, $-OC(=O)N(R^e)S(=O)_2R^e$, $-OC_{2-6}$alkylNR$^a$R$^f$, $-OC_{2-6}$alkylOR$^f$, $-SR^f$, $-S(=O)R^e$, $-S(=O)_2R^e$, $-S(=O)_2NR^aR^f$, $-S(=O)_2N(R^f)C(=O)R^e$, $-S(=O)_2N(R^f)C(=O)OR^e$, $-S(=O)_2N(R^f)C(=O)NR^aR^f$, $-NR^aR^f$, $-N(R^f)C(=O)R^e$, $-N(R^f)C(=O)OR^e$, $-N(R^f)C(=O)NR^aR^f$, $-N(R^f)C(=NR^a)NR^aR^f$, $-N(R^f)S(=O)_2R^e$, $-N(R^f)S(=O)_2NR^aR^f$, $-NR^fC_{2-6}$alkylNR$^a$R$^f$ and $-NR^fC_{2-6}$alkylOR$^f$.

In another embodiment, in conjunction with any one of the above and below embodiments, $R^{10}$ and $R^{11}$ together are a saturated or unsaturated 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from $=O$, $R^e$, halo, cyano, nitro, $-C(=O)R^e$, $-C(=O)OR^e$, $-C(=O)NR^aR^f$, $-C(=NR^a)NR^aR^f$, $-OR^f$, $-OC(=O)R^e$, $-OC(=O)NR^aR^f$, $-OC(=O)N(R^e)S(=O)_2R^e$, $-OC_{2-6}$alkylNR$^a$R$^f$, $-OC_{2-6}$alkylOR$^f$, $-SR^f$, $-S(=O)R^e$, $-S(=O)_2R^e$, $-S(=O)_2NR^aR^f$, $-S(=O)_2N(R^f)C(=O)R^e$, $-S(=O)_2N(R^f)C(=O)OR^e$, $-S(=O)_2N(R^f)C(=O)NR^aR^f$, $-NR^aR^f$, $-N(R^f)C(=O)R^e$, $-N(R^f)C(=O)OR^e$, $N(R^f)C(=O)NR^aR^f$, $-N(R^f)C(=NR^a)NR^aR^f$, $-N(R^f)S(=O)_2R^e$, $-N(R^f)S(=O)_2NR^aR^f$, $-NR^fC_{2-6}$alkylNR$^a$R$^f$ and $-NR^fC_{2-6}$alkylOR$^f$.

In another embodiment, in conjunction with any one of the above and below embodiments, $R^{10}$ and $R^{11}$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 1 or 2 substituents selected from $R^e$, halo, cyano, nitro, $-C(=O)R^e$, $-C(=O)OR^e$, $-C(=O)NR^aR^f$, $-C(=NR^a)NR^aR^f$, $-OR^f$, $-OC(=O)R^e$, $-OC(=O)NR^aR^f$, $-OC(=O)N(R^f)S(=O)_2R^eR^f$, $-OC_{2-6}$alkylNR$^a$R$^f$, $-OC_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^f$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$.

Sub-embodiment O: In another embodiment, in conjunction with any one of the above and below embodiments, R$^{10}$ and R$^{11}$ together are a saturated or unsaturated 3-atom bridge containing 1 or 2 atoms selected from O, N and S with the remaining atoms being carbon, wherein the bridge is substituted by 1 or 2 substituents selected from R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$.

Sub-embodiment P: In another embodiment, in conjunction with any one of the above and below embodiments, R$^{10}$ and R$^{11}$ together are a saturated or unsaturated 3-atom bridge containing 1 or 2 atoms selected from O, N and S with the remaining atoms being carbon, wherein the bridge is substituted by a substituents selected from R$^e$, —C(=O)R$^e$, —C(=O)OR$^e$, —C(=O)NR$^a$R$^f$, —OR, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$; and the bridge is additionally substituted by 0 or 1 substituents selected from R$^e$, oxo, halo, cyano, nitro, —C(=O)R$^e$, —C(=O)OR$^e$, —C(=O)NR$^a$R$^f$, —C(=NR$^a$R$^f$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(f)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$.

In another embodiment, in conjunction with any one of the above and below embodiments, R$^{10}$ and R$^{11}$ together are a saturated or unsaturated 3-atom bridge containing 1 or 2 atoms selected from O, N and S with the remaining atoms being carbon, wherein the bridge is substituted by a substituents selected from —C(=O)R$^e$, —C(=O)OR$^e$, —C(=O)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$.

In another embodiment, in conjunction with any one of the above and below embodiments, R$^{12}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{12}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{12}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, N(R$^a$)C(=O)(C$_{1-8}$alkyl) —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; wherein if R$^{11}$ or R$^{13}$ is CF$_3$, then R$^{12}$ is not F; or R$^{11}$ and R$^{12}$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(f)S(=O)$_2$NR$^a$R$^f$, —NR$^f$C$_{2-6}$alkylNR$^a$R$^f$ and —NR$^f$C$_{2-6}$alkylOR$^e$; wherein when R$^3$ is NH$_2$, then -R$^{11}$-R$^{12}$- is not —C=C—C=N— or any substituted version thereof.

Sub-embodiment Q: In another embodiment, in conjunction with any one of the above and below embodiments, R$^{12}$ is H.

In another embodiment, in conjunction with any one of the above and below embodiments, R$^{12}$ is independently, at each instance, selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)

($C_{1-8}$alkyl), —OC(=O)NR$^a$R$^a$, —OC(=O)N(R$^a$)S(=O)$_2$ ($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{12}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$ alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{12}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; wherein if R$^{11}$ or R$^{13}$ is CF$_3$, then R$^{12}$ is not F; or R$^{11}$ and R$^{12}$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O) NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$ alkylOR$^f$; wherein when R$^3$ is NH$_2$, then -R$^{11}$-R$^{12}$- is not —C=C—C=N— or any substituted version thereof.

In another embodiment, in conjunction with any one of the above and below embodiments, R$^{12}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$ alkyl), —S(=O)$_2$N(R$^a$)C(=O)O($C_{1-8}$alkyl), —S(=O)$_2$N(R$^a$)C(=O)NR$^a$R$^a$, NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$ alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

Sub-embodiment R: In another embodiment, in conjunction with any one of the above and below embodiments, R$^{11}$ and R$^{12}$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O) R$^e$, —OC(=O)NR$^a$R$^f$, —OC(=O)NR$^a$R$^f$)S(=O)$_2$R$^e$, —OC$_{2-6}$ alkylNR$^a$R$^f$, —SR$^f$, —S(=O)R$^e$, —S(=O)$_2$R$^e$, —S(=O)$_2$ NR$^a$R$^f$, —S(=O)$_2$N(R$^f$)C(=O)R$^e$, —S(=O)$_2$N (R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O) NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$; wherein when R$^3$ is NH$_2$, then -R$^{11}$-R$^{12}$- is not —C=C—C=N— or any substituted version thereof.

Sub-embodiment S: In another embodiment, in conjunction with any one of the above and below embodiments, R$^{11}$ and R$^{12}$ together are a saturated or unsaturated 3-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from =O, R$^e$, halo, cyano, nitro, —C(=O)R$^e$, —C(=O)OR$^e$, —C(=O) NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N (R$^f$)C(=O)OR$^e$, —S(=O)$_2$N(R$^f$)C(=O)NR$^a$R$^f$, —NR$^a$R$^f$, —N(R$^f$)C(=O)R$^e$, —N(f)C(=O)OR$^e$, —N(R$^f$)C(=O) NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$.

In another embodiment, in conjunction with any one of the above and below embodiments, R$^{11}$ and R$^{12}$ together are a saturated or unsaturated 3-atom bridge containing 1 or 2 atoms selected from O, N and S with the remaining atoms being carbon, wherein the bridge is substituted by 0, 1 or 2 substituents selected from =O, R$^e$, halo, cyano, nitro, —C(=O)R$^e$, —C(=O)OR$^e$, —C(=O)NR$^a$R$^f$, —C(=NR$^a$) NR$^a$R$^f$, —OR$^f$, —OC(=O)R$^e$, —OC(=O)NR$^a$R$^f$, —OC (=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O) R$^e$, —N(R$^f$)C(=O)OR$^e$, —N(R$^f$)C(=O)NR$^a$R$^f$, —N(R$^f$)C (=NR$^a$)NR$^a$R$^f$, —N(R$^f$)S(=O)$_2$R$^e$, —N(R$^f$)S(=O)$_2$ NR$^a$R$^f$, —NR$^f$C$_{2-6}$alkylNR$^a$R$^f$ and —NR$^f$C$_{2-6}$alkylOR$^f$.

In another embodiment, in conjunction with any one of the above and below embodiments, R$^{11}$ and R$^{12}$ together are a saturated or unsaturated 3-atom bridge containing 1 or 2 atoms selected from O, N and S with the remaining atoms being carbon, wherein the bridge is substituted by 1 or 2 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$.

In another embodiment, in conjunction with any one of the above and below embodiments, R$^{11}$ and R$^{12}$ together are a saturated or unsaturated 3-atom bridge containing 1 or 2 atoms selected from O, N and S with the remaining atoms being carbon, wherein the bridge is substituted by R$^e$, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ or —NR$^f$C$_{2-6}$alkylOR$^f$.

In another embodiment, in conjunction with any one of the above and below embodiments, R$^{11}$ and R$^{12}$ together are a saturated or unsaturated 3-atom bridge containing 1 or 2 atoms selected from O, N and S with the remaining atoms being carbon, wherein the bridge is substituted by —C(=O)R$^e$, —C(=O)OR$^e$, —C(=O)NR$^a$R$^f$, —C(=NR$^a$)NR$^a$R$^f$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ or —NR$^f$C$_{2-6}$alkylOR$^f$.

In another embodiment, in conjunction with any one of the above and below embodiments, R$^{11}$ and R$^{12}$ together are a saturated or unsaturated 4-atom bridge containing 1, 2 or 3 atoms selected from O, N and S with the remaining atoms being carbon, so long as the combination of O and S atoms is not greater than 2 and first attachment atom in R$^{12}$ is not N, wherein the bridge is substituted by 0, 1 or 2 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^e$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$.

Sub-embodiment T: In another embodiment, in conjunction with any one of the above and below embodiments, R$^{11}$ and R$^{12}$ together form a -R$^{11}$-R$^{12}$- bridge selected from —O—C=C—O—, —N—C=C—C— and —N=C—C=C—, wherein the bridge is substituted by 0, 1 or 2 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^e$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$.

In another embodiment, in conjunction with any one of the above and below embodiments, R$^{11}$ and R$^{12}$ together form a -R$^{11}$-R$^{12}$- bridge selected from —O—C=C—O—, —N—C=C—C— and —N=C—C=C—, wherein the bridge is substituted by 1 or 2 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$.

In another embodiment, in conjunction with any one of the above and below embodiments, R$^{13}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, NR$^a$R$^a$, N(R$^a$)C(=O)(C 1-alkyl), —N(R$^a$)C(=O)O(C$_{1-8}$alkyl), —N(R$^a$)C(=O)NR$^a$R$^a$, N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{13}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkyNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{13}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$ alkyl), —S(=O)$_2$N(R$^a$)C(=O)O(C$_{1-8}$alkyl), —S(=O)$_2$N(R$^a$)C(=O)NR$^a$R$^a$, NR$^a$R$^a$, N(R$^a$)C(=O)(C$_{1-8}$alkyl), —N(R$^a$)C(=O)O(C$_{1-8}$alkyl), —N(R$^a$)C(=O)NR$^a$R$^a$, N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$ alkylOR$^a$.

In another embodiment, in conjunction with any one of the above and below embodiments, $R^{13}$ is H.

In another embodiment, in conjunction with any one of the above and below embodiments, $R^{13}$ is independently, at each instance, selected from $C_{1-8}$alkyl, cyano, nitro, —C(=O)($C_{1-8}$ alkyl), —C(=O)O($C_{1-8}$alkyl), —C(=O)NR$^a$R$^a$, —C(=NR$^a$)NR$^a$R$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$ alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, $R^{13}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, $R^{13}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, $R^{14}$ is independently, at each instance, selected from H, $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or $R^{14}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or $R^{14}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, $R^{14}$ is H.

In another embodiment, in conjunction with any one of the above and below embodiments, $R^{14}$ is independently, at each instance, selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or $R^{14}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$ alkyl), —OC(=O)NR$^a$R$^a$, —OC(=O)N(R$^a$)S(=O)$_2$($C_{1-8}$ alkyl), —OC$_{2-6}$alkylNR$^a$R$^a$, OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S (=O)$_2$NR$^a$R$^a$, —NR$^a$C$_{2-6}$alkylNR$^a$R$^a$ and —NR$^a$C$_{2-6}$alkylOR$^a$; or R$^{14}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$ alkylNR$^a$R$^a$, —OC$_{2-6}$alkylOR$^a$, —SR$^a$, —S(=O)(C$_{1-8}$ alkyl), —S(=O)$_2$(C$_{1-8}$alkyl), —S(=O)$_2$NR$^a$R$^a$, —S(=O)$_2$ N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$ alkylNR$^a$R$^a$ and —NR$^a$C$_{2-6}$alkylOR$^a$.

In another embodiment, in conjunction with any one of the above and below embodiments, at least one of R$^{10}$, R$^{11}$, R$^{12}$, R$^{13}$ and R$^{14}$ is other than H.

In another embodiment, in conjunction with any one of the above and below embodiments, at least two of R$^{10}$, R$^{11}$, R$^{12}$, R$^{13}$ and R$^{14}$ is other than H.

R$^a$ is independently, at each instance, H, phenyl, benzyl or C$_{1-6}$alkyl;

R$^b$ is a heterocycle selected from the group of thiophene, pyrrole, 1,3-oxazole, 1,3-thiazole, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, furan, imidazol-1-yl, imidazol-4-yl, 1,2,4-triazol-4-yl, 1,2,4-triazol-5-yl, isoxazol-3-yl, isoxazol-5-yl, pyrazol-3-yl, pyrazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazoline, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazole, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4] thidiazole, 2,5-dihydro-[1,2,4] thiadiazole, 4,5-dihydro-[1,2,4] thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4] thiadiazole, 4,5-dihydro-[1,2,4] thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2] thiazine, 3,6-dihydro-2H-[1,2] thiazine, 3,4-dihydro-2H-[1,2] thiazine, 5,6-dihydro-2H-[1,3]oxazine, 5,6-dihydro-4H-[1,3]oxazine, 3,6-dihydro-2H-[1,3]oxazine, 3,4dihydro-2H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5] thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 4,5-dihydropyridine, 1,6-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 2,3-dihydropyrimidine, 2,5-dihydropyrimidine, 5,6-dihydropyrimidine, 3,6-dihydropyrimidine, 4,5-dihydropyrazine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine and 1,4,2-oxathiazine, wherein the heterocycle is optionally vicinally fused with a saturated or unsaturated 5-, 6- or 7-membered ring containing 0, 1 or 2 atoms independently selected from N, O and S;

R$^c$ is independently, in each instance, phenyl substituted by 0, 1 or 2 groups selected from halo, C$_{1-4}$alkyl, C$_{1-3}$haloalkyl, —OR$^a$ and —NR$^a$R$^a$; or R$^c$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, $C_{1-4}$alkyl, $C_{1-3}$haloalkyl, —$OR^a$ and —$NR^aR^a$;

$R^d$ is hydrogen or —$CH_3$;

$R^e$ is, independently, in each instance, $C_{1-9}$alkyl substituted by 0, 1, 2, 3 or 4 substituents selected from halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —$NR^aC_{2-6}$alkylN$R^aR^a$ and —$NR^aC_{2-6}$alkylO$R^a$; and wherein the $C_{1-9}$alkyl is additionally substituted by 0 or 1 groups independently selected from $R^g$;

$R^f$ is, independently, in each instance, $R^e$ or H; and $R^g$ is, independently, in each instance, a saturated or unsaturated 5- or 6-membered monocyclic ring containing 1, 2 or 3 atoms selected from N, O and S, so long as the combination of O and S atoms is not greater than 2, wherein the carbon atoms of the ring are substituted by 0 or 1 oxo groups.

As stated above, the above embodiments and sub-embodiments may be used in conjuction with other embodiments and subembodiments listed. The following table is a non-exclusive, non-limiting list of some of the combinations of embodiments. Although the following embodiment sets are meant to be used with any of the above embodiments, they are also considered wherein $R^5$, $R^6$, $R^8$, $R^{13}$ and $R^{14}$ are all H.

Where X is =N— and Y is —CH—:

| Emb. # | $R^1$ | $R^4$ | $R^7$ | $R^9$ | $R^{10}$ | $R^{11}$ | $R^{12}$ |
|---|---|---|---|---|---|---|---|
| 1001 | C | E | — | — | N | N | Q |
| 1002 | C | E | — | — | O | O | Q |
| 1003 | C | E | — | — | P | P | Q |
| 1004 | C | E | — | — | M | R | R |
| 1005 | C | E | — | — | M | S | S |
| 1006 | C | E | — | — | M | T | T |
| 1007 | C | D | — | — | — | — | — |
| 1008 | C | F | — | — | — | — | — |
| 1009 | C | G | — | — | — | — | — |
| 1010 | A | E | H | J | N | N | Q |
| 1011 | A | E | H | J | O | O | Q |
| 1012 | A | E | H | J | P | P | Q |
| 1013 | A | E | H | J | M | R | R |
| 1014 | A | E | H | J | M | S | S |
| 1015 | A | E | H | J | M | T | T |
| 1016 | A | D | H | J | — | — | — |
| 1017 | A | F | H | J | — | — | — |
| 1018 | A | G | H | J | — | — | — |
| 1019 | A | E | H | K | N | N | Q |
| 1020 | A | E | H | K | O | O | Q |
| 1021 | A | E | H | K | P | P | Q |
| 1022 | A | E | H | K | M | R | R |
| 1023 | A | E | H | K | M | S | S |
| 1024 | A | E | H | K | M | T | T |
| 1025 | A | D | H | K | — | — | — |
| 1026 | A | F | H | K | — | — | — |
| 1027 | A | G | H | K | — | — | — |
| 1028 | A | E | H | L | N | N | Q |
| 1029 | A | E | H | L | O | O | Q |
| 1030 | A | E | H | L | P | P | Q |
| 1031 | A | E | H | L | M | R | R |
| 1032 | A | E | H | L | M | S | S |
| 1033 | A | E | H | L | M | T | T |
| 1034 | A | D | H | L | — | — | — |
| 1035 | A | F | H | L | — | — | — |
| 1036 | A | G | H | L | — | — | — |
| 1037 | A | E | I | J | N | N | Q |
| 1038 | A | E | I | J | O | O | Q |
| 1039 | A | E | I | J | P | P | Q |
| 1040 | A | E | I | J | M | R | R |
| 1041 | A | E | I | J | M | S | S |
| 1042 | A | E | I | J | M | T | T |
| 1043 | A | D | I | J | — | — | — |
| 1044 | A | F | I | J | — | — | — |
| 1045 | A | G | I | J | — | — | — |
| 1046 | A | E | I | K | N | N | Q |
| 1047 | A | E | I | K | O | O | Q |
| 1048 | A | E | I | K | P | P | Q |
| 1049 | A | E | I | K | M | R | R |
| 1050 | A | E | I | K | M | S | S |
| 1051 | A | E | I | K | M | T | T |
| 1052 | A | D | I | K | — | — | — |
| 1053 | A | F | I | K | — | — | — |
| 1054 | A | G | I | K | — | — | — |
| 1055 | A | E | I | L | N | N | Q |
| 1056 | A | E | I | L | O | O | Q |
| 1057 | A | E | I | L | P | P | Q |
| 1058 | A | E | I | L | M | R | R |
| 1059 | A | E | I | L | M | S | S |
| 1060 | A | E | I | L | M | T | T |
| 1061 | A | D | I | L | — | — | — |
| 1062 | A | F | I | L | — | — | — |
| 1063 | A | G | I | L | — | — | — |
| 1064 | B | E | H | J | N | N | Q |
| 1065 | B | E | H | J | O | O | Q |
| 1066 | B | E | H | J | P | P | Q |
| 1067 | B | E | H | J | M | R | R |
| 1068 | B | E | H | J | M | S | S |
| 1069 | B | E | H | J | M | T | T |
| 1070 | B | D | H | J | — | — | — |
| 1071 | B | F | H | J | — | — | — |
| 1072 | B | G | H | J | — | — | — |
| 1073 | B | E | H | K | N | N | Q |
| 1074 | B | E | H | K | O | O | Q |
| 1075 | B | E | H | K | P | P | Q |
| 1076 | B | E | H | K | M | R | R |
| 1077 | B | E | H | K | M | S | S |
| 1078 | B | E | H | K | M | T | T |
| 1079 | B | D | H | K | — | — | — |
| 1080 | B | F | H | K | — | — | — |
| 1081 | B | G | H | K | — | — | — |
| 1082 | B | E | H | L | N | N | Q |
| 1083 | B | E | H | L | O | O | Q |
| 1084 | B | E | H | L | P | P | Q |
| 1085 | B | E | H | L | M | R | R |
| 1086 | B | E | H | L | M | S | S |
| 1087 | B | E | H | L | M | T | T |
| 1088 | B | D | H | L | — | — | — |
| 1089 | B | F | H | L | — | — | — |
| 1090 | B | G | H | L | — | — | — |
| 1091 | B | E | I | J | N | N | Q |
| 1092 | B | E | I | J | O | O | Q |
| 1093 | B | E | I | J | P | P | Q |
| 1094 | B | E | I | J | M | R | R |
| 1095 | B | E | I | J | M | S | S |
| 1096 | B | E | I | J | M | T | T |
| 1097 | B | D | I | J | — | — | — |
| 1098 | B | F | I | J | — | — | — |
| 1099 | B | G | I | J | — | — | — |
| 1100 | B | E | I | K | N | N | Q |
| 1101 | B | E | I | K | O | O | Q |
| 1102 | B | E | I | K | P | P | Q |
| 1103 | B | E | I | K | M | R | R |
| 1104 | B | E | I | K | M | S | S |
| 1105 | B | E | I | K | M | T | T |
| 1106 | B | D | I | K | — | — | — |
| 1107 | B | F | I | K | — | — | — |

-continued

| Emb. # | R¹ | R⁴ | R⁷ | R⁹ | R¹⁰ | R¹¹ | R¹² |
|---|---|---|---|---|---|---|---|
| 1108 | B | G | I | K | — | — | — |
| 1109 | B | E | I | L | N | N | Q |
| 1110 | B | E | I | L | O | O | Q |
| 1111 | B | E | I | L | P | P | Q |
| 1112 | B | E | I | L | M | R | R |
| 1113 | B | E | I | L | M | S | S |
| 1114 | B | E | I | L | M | T | T |
| 1115 | B | D | I | L | — | — | — |
| 1116 | B | F | I | L | — | — | — |
| 1117 | B | G | I | L | — | — | — |

Where X is —CH— and Y is =N—:

| Emb. # | R¹ | R⁴ | R⁷ | R⁹ | R¹⁰ | R¹¹ | R¹² |
|---|---|---|---|---|---|---|---|
| 2001 | C | E | — | — | N | N | Q |
| 2002 | C | E | — | — | O | O | Q |
| 2003 | C | E | — | — | P | P | Q |
| 2004 | C | E | — | — | M | R | R |
| 2005 | C | E | — | — | M | S | S |
| 2006 | C | E | — | — | M | T | T |
| 2007 | C | D | — | — | — | — | — |
| 2008 | C | F | — | — | — | — | — |
| 2009 | C | G | — | — | — | — | — |
| 2010 | A | E | H | J | N | N | Q |
| 2011 | A | E | H | J | O | O | Q |
| 2012 | A | E | H | J | P | P | Q |
| 2013 | A | E | H | J | M | R | R |
| 2014 | A | E | H | J | M | S | S |
| 2015 | A | E | H | J | M | T | T |
| 2016 | A | D | H | J | — | — | — |
| 2017 | A | F | H | J | — | — | — |
| 2018 | A | G | H | J | — | — | — |
| 2019 | A | E | H | K | N | N | Q |
| 2020 | A | E | H | K | O | O | Q |
| 2021 | A | E | H | K | P | P | Q |
| 2022 | A | E | H | K | M | R | R |
| 2023 | A | E | H | K | M | S | S |
| 2024 | A | E | H | K | M | T | T |
| 2025 | A | D | H | K | — | — | — |
| 2026 | A | F | H | K | — | — | — |
| 2027 | A | G | H | K | — | — | — |
| 2028 | A | E | H | L | N | N | Q |
| 2029 | A | E | H | L | O | O | Q |
| 2030 | A | E | H | L | P | P | Q |
| 2031 | A | E | H | L | M | R | R |
| 2032 | A | E | H | L | M | S | S |
| 2033 | A | E | H | L | M | T | T |
| 2034 | A | D | H | L | — | — | — |
| 2035 | A | F | H | L | — | — | — |
| 2036 | A | G | H | L | — | — | — |
| 2037 | A | E | I | J | N | N | Q |
| 2038 | A | E | I | J | O | O | Q |
| 2039 | A | E | I | J | P | P | Q |
| 2040 | A | E | I | J | M | R | R |
| 2041 | A | E | I | J | M | S | S |
| 2042 | A | E | I | J | M | T | T |
| 2043 | A | D | I | J | — | — | — |
| 2044 | A | F | I | J | — | — | — |
| 2045 | A | G | I | J | — | — | — |
| 2046 | A | E | I | K | N | N | Q |
| 2047 | A | E | I | K | O | O | Q |
| 2048 | A | E | I | K | P | P | Q |
| 2049 | A | E | I | K | M | R | R |
| 2050 | A | E | I | K | M | S | S |
| 2051 | A | E | I | K | M | T | T |
| 2052 | A | D | I | K | — | — | — |
| 2053 | A | F | I | K | — | — | — |
| 2054 | A | G | I | K | — | — | — |
| 2055 | A | E | I | L | N | N | Q |
| 2056 | A | E | I | L | O | O | Q |
| 2057 | A | E | I | L | P | P | Q |

-continued

| Emb. # | R¹ | R⁴ | R⁷ | R⁹ | R¹⁰ | R¹¹ | R¹² |
|---|---|---|---|---|---|---|---|
| 2058 | A | E | I | L | M | R | R |
| 2059 | A | E | I | L | M | S | S |
| 2060 | A | E | I | L | M | T | T |
| 2061 | A | D | I | L | — | — | — |
| 2062 | A | F | I | L | — | — | — |
| 2063 | A | G | I | L | — | — | — |
| 2064 | B | E | H | J | N | N | Q |
| 2065 | B | E | H | J | O | O | Q |
| 2066 | B | E | H | J | P | P | Q |
| 2067 | B | E | H | J | M | R | R |
| 2068 | B | E | H | J | M | S | S |
| 2069 | B | E | H | J | M | T | T |
| 2070 | B | D | H | J | — | — | — |
| 2071 | B | F | H | J | — | — | — |
| 2072 | B | G | H | J | — | — | — |
| 2073 | B | E | H | K | N | N | Q |
| 2074 | B | E | H | K | O | O | Q |
| 2075 | B | E | H | K | P | P | Q |
| 2076 | B | E | H | K | M | R | R |
| 2077 | B | E | H | K | M | S | S |
| 2078 | B | E | H | K | M | T | T |
| 2079 | B | D | H | K | — | — | — |
| 2080 | B | F | H | K | — | — | — |
| 2081 | B | G | H | K | — | — | — |
| 2082 | B | E | H | L | N | N | Q |
| 2083 | B | E | H | L | O | O | Q |
| 2084 | B | E | H | L | P | P | Q |
| 2085 | B | E | H | L | M | R | R |
| 2086 | B | E | H | L | M | S | S |
| 2087 | B | E | H | L | M | T | T |
| 2088 | B | D | H | L | — | — | — |
| 2089 | B | F | H | L | — | — | — |
| 2090 | B | G | H | L | — | — | — |
| 2091 | B | E | I | J | N | N | Q |
| 2092 | B | E | I | J | O | O | Q |
| 2093 | B | E | I | J | P | P | Q |
| 2094 | B | E | I | J | M | R | R |
| 2095 | B | E | I | J | M | S | S |
| 2096 | B | E | I | J | M | T | T |
| 2097 | B | D | I | J | — | — | — |
| 2098 | B | F | I | J | — | — | — |
| 2099 | B | G | I | J | — | — | — |
| 2100 | B | E | I | K | N | N | Q |
| 2101 | B | E | I | K | O | O | Q |
| 2102 | B | E | I | K | P | P | Q |
| 2103 | B | E | I | K | M | R | R |
| 2104 | B | E | I | K | M | S | S |
| 2105 | B | E | I | K | M | T | T |
| 2106 | B | D | I | K | — | — | — |
| 2107 | B | F | I | K | — | — | — |
| 2108 | B | G | I | K | — | — | — |
| 2109 | B | E | I | L | N | N | Q |
| 2110 | B | E | I | L | O | O | Q |
| 2111 | B | E | I | L | P | P | Q |
| 2112 | B | E | I | L | M | R | R |
| 2113 | B | E | I | L | M | S | S |
| 2114 | B | E | I | L | M | T | T |
| 2115 | B | D | I | L | — | — | — |
| 2116 | B | F | I | L | — | — | — |
| 2117 | B | G | I | L | — | — | — |

Another aspect of the current invention relates to compounds having the general structure:

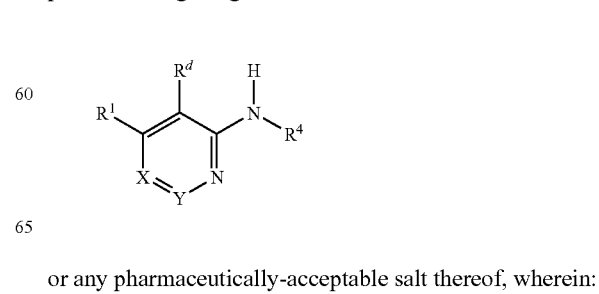

or any pharmaceutically-acceptable salt thereof, wherein:

X is =N— or =C(R²)—;
Y is =N— or =C(R³)—, wherein at least one of X and Y is not =N—;
n is independently, at each instance, 0, 1 or 2.
R¹ is

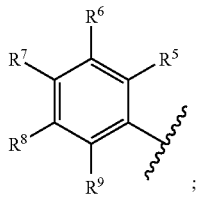

or R¹ is a naphthyl substituted by 0, 1, 2 or 3 substituents independently selected from R⁵; or R¹ is R^b substituted by 1, 2 or 3 substituents independently selected from R⁵;

R² is, independently, in each instance, R¹⁰, $C_{1-8}$alkyl substituted by 0, 1 or 2 substituents selected from R¹⁰, —(CH₂)ₙ phenyl substituted by 0, 1, 2 or 3 substitutents independently selected from R¹⁰, or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from R¹⁰;

R³ is, independently, in each instance, H, halo, —NH₂, —NHC$_{1-3}$alkyl, —N(C$_{1-3}$alkyl)C$_{1-3}$alkyl, or C$_{1-3}$alkyl;

R⁴ is

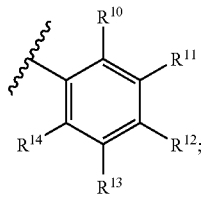

or

R⁴ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from $C_{1-9}$alkyl, $C_{1-4}$haloalkyl, halo, nitro, cyano, oxo, —OR^a, —S(=O)ₙ$C_{1-6}$alkyl, —OC$_{1-4}$haloalkyl, —OC$_{2-6}$alkylNR^aR^a, —OC$_{2-6}$alkylOR^a, —OC$_{1-6}$alkylC(=O)OR^a, —NR^aR^a, —NR^aC$_{1-4}$haloalkyl, —NR^aC$_{2-6}$alkylNR^aR^a, —NR^aC$_{2-6}$alkylOR^a, —C(=O)C$_{1-6}$alkyl, —C(=O)OC$_{1-6}$alkyl, —OC(=O)C$_{1-6}$alkyl, —C(=O)NR^aC$_{1-6}$alkyl and —NR^aC(=O)C$_{1-6}$alkyl; and unsaturated carbon atoms may be additionally substituted by =O; and any nitrogen atoms in the chain are substituted by H, —C$_{1-6}$alkylOR^aR^a, —C$_{1-6}$alkyl, —C$_{1-6}$alkylNR^aR^a, —C$_{1-3}$alkylC(=O)OR^a, —C$_{1-3}$alkylC(=O)NR^aR^a, —C$_{1-3}$alkylOC(=O)C$_{1-6}$alkyl, —C$_{1-3}$alkylNR^aC(=O)C$_{1-6}$alkyl, —C(=O)R^c or —C$_{1-3}$alkylR^c;

or R⁴ is 10-membered bicyclic ring comprising fused 6-membered rings, containing 0, 1, 2, 3 or 4 N atoms with the remainder being carbon atoms, with at least one of the 6-membered rings being aromatic, wherein the carbon atoms are substituted by H, halo, OR^a, NR^aR^a, $C_{1-6}$alkyl and $C_{1-3}$haloalkyl; and unsaturated carbon atoms may be additionally substituted by =O; but in no instance is R⁴ 3,5-ditrifluoromethylphenyl or 3-trifluoromethyl-4-fluorophenyl;

R⁵ is independently, at each instance, H, $C_{1-5}$alkyl, $C_{1-4}$haloalkyl, halo, nitro, cyano, —OC$_{1-6}$alkyl, —OC$_{1-4}$haloalkyl, —OC$_{2-6}$alkylNR^aR^a, —OC$_{2-6}$alkylOR^a, —NR^aR^a, —NR^aC$_{1-4}$haloalkyl, —NR^aC$_{2-6}$alkylNR^aR^a, —NR^aC$_{2-6}$alkylOR^a, naphthyl, —CO₂(C$_{1-6}$alkyl), —C(=O)(C$_{1-6}$alkyl), —C(=O)NR^aR^a, —NR^aC(=O)R^a, —NR^aC(=O)NR^aR^a, —NR^aCO₂(C$_{1-6}$alkyl), —C$_{1-8}$alkylOR^a, —C$_{1-6}$alkylNR^aR^a, —S(=O)ₙ(C$_{1-6}$alkyl), —S(=O)₂NR^aR^a, —NR^aS(=O)₂(C$_{1-6}$alkyl), —OC(=O)NR^aR^a, a phenyl ring substituted with 0, 1, 2, or 3 substituents independently selected from R¹⁰; or R⁵ is a saturated or unsaturated 5- or 6-membered ring heterocycle containing 1, 2 or 3 atoms selected from O, N and S, substituted with 0, 1, 2, or 3 substituents independently selected from R¹⁰;

R⁶ is independently, at each instance, H, $C_{1-5}$alkyl, $C_{1-4}$haloalkyl, halo, —OC$_{1-6}$alkyl, —OC$_{1-4}$haloalkyl, —OC$_{2-6}$alkylNR^aR^a, —OC$_{2-6}$alkylOR^a, —NR^aR^a, —NR^aC$_{1-4}$haloalkyl, —NR^aC$_{2-6}$alkylNR^aR^a or —NR^aC$_{2-6}$alkylOR^a, —C$_{1-8}$alkylOR^a, —C$_{1-6}$alkylNR^aR^a, —S(C$_{1-6}$alkyl), a phenyl ring substituted with 1, 2, or 3 substituents independently selected from R¹⁰; or R⁶ is a saturated or unsaturated 5- or 6-membered ring heterocycle containing 1, 2 or 3 atoms selected from O, N and S substituted with 0, 1, 2, or 3 substituents independently selected from R¹⁰;

R⁷ is independently, at each instance, H, $C_{1-8}$alkyl, $C_{1-4}$haloalkyl, halo, —OC$_{1-6}$alkyl, —OC$_{1-4}$haloalkyl, —OC$_{2-6}$alkylNR^aR^a, —OC$_{2-6}$alkylOR^a, —NR^aR^a, —NR^aC$_{1-4}$haloalkyl, —NR^aC$_{2-6}$alkylNR^aR^a, —NR^aC$_{2-6}$alkylOR^a, —C$_{1-8}$alkylOR^a, —C$_{1-6}$alkylNR^aR^a or —S(C$_{1-6}$alkyl); or R⁷ is a saturated or unsaturated 4- or 5-membered ring heterocycle containing a single nitrogen atom, wherein the ring is substituted with 0, 1 or 2 substituents independently selected from halo, $C_{1-2}$haloalkyl and $C_{1-3}$alkyl;

R⁸ is independently, at each instance, H, $C_{1-5}$alkyl, $C_{1-4}$haloalkyl, halo, —OC$_{1-6}$alkyl, —OC$_{1-4}$haloalkyl, —OC$_{2-6}$alkylNR^aR^a, —OC$_{2-6}$alkylOR^a, —NR^aR^a, —NR^aC$_{1-4}$haloalkyl, —NR^aC$_{2-6}$alkylNR^aR^a, —NR^aC$_{2-6}$alkylOR^a, —C$_{1-8}$alkylOR^a, —C$_{1-6}$alkylNR^aR^a, —S(C$_{1-6}$alkyl), a phenyl ring substituted with 1, 2, or 3 substituents independently selected from R¹⁰, or R⁸ is a saturated or unsaturated 5- or 6-membered ring heterocycle containing 1, 2 or 3 atoms selected from O, N and S substituted with 0, 1, 2, or 3 substituents independently selected from R¹⁰;

R⁹ is independently, at each instance, H, $C_{1-8}$alkyl, $C_{1-4}$haloalkyl, halo, nitro, cyano, —OC$_{1-6}$alkyl, —OC$_{1-4}$haloalkyl, —OC$_{2-6}$alkylNR^aR^a, —OC$_{2-6}$alkylOR^a, —NR^aR^a, —NR^aC$_{1-4}$haloalkyl, —NR^aC$_{2-6}$alkylNR^aR^a or —NR^aC$_{2-6}$alkylOR^a, —CO₂(C$_{1-6}$alkyl), —C(=O)(C$_{1-6}$alkyl), —C(=O)NR^aR^a, —NR^aC(=O)(C$_{1-6}$alkyl), —NR^aC(=O)NR^aR^a, —NR^aCO₂(C$_{1-6}$alkyl), —C$_{1-8}$alkylOR^a, —C$_{1-6}$alkylNR^aR^a, —S(=O)ₙ(C$_{1-6}$alkyl), —S(=O)₂NR^aR^a, —NR^aS(=O)₂(C$_{1-6}$alkyl), —OC(=O)NR^aR^a, a phenyl ring substituted with 0, 1, 2, or 3 substituents independently selected from R¹⁰; or R⁹ is a saturated or unsaturated 5- or 6-membered ring heterocycle containing 1, 2 or 3 atoms selected from O, N and S substituted with 0, 1, 2, or 3 substituents independently selected from R¹⁰; wherein at least one of R⁵, R⁶, R⁷, R⁸ and R⁹ is $C_{1-8}$alkyl, $C_{1-4}$haloalkyl, halo, —OC$_{1-4}$haloalkyl, —OC$_{2-6}$alkylNR^aR^a, —OC$_{2-6}$alkylOR^a, —NR$^a$C$_{1-4}$haloalkyl, —NR$^a$C$_{2-6}$alkylNR$^a$R$^a$, —NR$^a$C$_{2-6}$alkylOR$^a$, —C$_{1-8}$alkylOR$^a$, —C$_{1-6}$alkylNR$^a$R$^a$ or —S(C$_{1-6}$alkyl); or R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl;

R$^{10}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C 18alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$ alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^{11}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$ alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{11}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{11}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$ alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ and R$^{11}$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the each of the carbon atoms in the chain is substituted by H, =O, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$, and any nitrogen atoms in the chain are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;

R$^{12}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$ and —NR$^a$C$_{2-6}$alkylOR$^a$; or R$^{12}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{12}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; wherein if R$^{11}$ or R$^{13}$ is CF$_3$, then R$^{12}$ is not F; or R$^{11}$ and R$^{12}$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the each of the carbon atoms in the chain is substituted by H, =O, $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$, and any nitrogen atoms in the chain are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$;

R$^{13}$ is independently, at each instance, selected from H, $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{13}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{13}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^{14}$ is independently, at each instance, selected from H, $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{14}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{14}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —O$C_{2-6}$alkylNR$^a$R$^a$, —O$C_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$ alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$$C_{2-6}$alkylNR$^a$R$^a$ and —NR$^a$$C_{2-6}$alkylOR$^a$;

R$^a$ is independently, at each instance, H, phenyl, benzyl or $C_{1-6}$alkyl;

R$^b$ is a heterocycle selected from the group of thiophene, pyrrole, 1,3-oxazole, 1,3-thiazole, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, furan, imidazol-1-yl, imidazol-4-yl, 1,2,4-triazol-4-yl, 1,2,4-triazol-5-yl, isoxazol-3-yl, isoxazol-5-yl, pyrazol-3-yl, pyrazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,2-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazoline, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazole, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4] thidiazole, 2,5-dihydro-[1,2,4] thiadiazole, 4,5-dihydro-[1,2,4] thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4] thiadiazole, 4,5-dihydro-[1,2,4] thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2] thiazine, 3,6-dihydro-2H-[1,2] thiazine, 3,4-dihydro-2H-[1,2] thiazine, 5,6-dihydro-2H-[1,3]oxazine, 5,6-dihydro-4H-[1,3]oxazine, 3,6-dihydro-2H-[1,3]oxazine, 3,4-dihydro-2H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 4,5-dihydropyridine, 1,6-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 2,3-dihydropyrimidine, 2,5-dihydropyrimidine, 5,6-dihydropyrimidine, 3,6-dihydropyrimidine, 4,5-dihydropyrazine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine and 1,4,2-oxathiazine, wherein the heterocycle is optionally vicinally fused with a saturated or unsaturated 5-, 6- or 7-membered ring containing 0, 1 or 2 atoms independently selected from N, O and S;

R$^c$ is phenyl substituted by 0, 1 or 2 groups selected from halo, $C_{1-4}$alkyl, $C_{1-3}$haloalkyl, —OR$^a$ and —NR$^a$R$^a$; or R$^c$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, $C_{1-4}$alkyl, $C_{1-3}$haloalkyl, —OR$^a$ and —NR$^a$R$^a$; and $R^d$ is hydrogen or —CH$_3$.

In another embodiment, in conjunction with any one of the above and below embodiments, X is =N—; and either $R^6$ is independently, at each instance, H, C$_{1-5}$alkyl, C$_{2-4}$haloalkyl, halo, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$haloalkyl, —NR$^a$C$_{2-6}$alkylNR$^a$R$^a$ or —NR$^a$C$_{2-6}$alkylOR$^a$, —C$_{1-8}$alkylOR$^a$, —C$_{1-6}$alkylNR$^a$R$^a$, —S(C$_{1-6}$alkyl), a phenyl ring substituted with 1, 2, or 3 substituents independently selected from R$^{10}$; or R$^6$ is a saturated or unsaturated 5- or 6-membered ring heterocycle containing 1, 2 or 3 atoms selected from O, N and S substituted with 0, 1, 2, or 3 substituents independently selected from R$^{10}$; or R$^8$ is independently, at each instance, H, C$_{1-5}$alkyl, C$_{2-4}$haloalkyl, halo, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$haloalkyl, —NR$^a$C$_{2-6}$NR$^a$R$^a$, —NR$^a$C$_{2-6}$alkylOR$^a$, —C$_{1-8}$alkylOR$^a$, —C$_{1-6}$alkylNR$^a$R$^a$, —S(C$_{1-6}$alkyl), a phenyl ring substituted with 1, 2, or 3 substituents independently selected from R$^{10}$, or R$^6$ is a saturated or unsaturated 5- or 6-membered ring heterocycle containing 1, 2 or 3 atoms selected from O, N and S substituted with 0, 1, 2, or 3 substituents independently selected from R$^{10}$.

In another embodiment, in conjunction with any one of the above and below embodiments, R$^3$ is halo, —NH$_2$, —NHC$_{1-3}$alkyl, —N(C$_{1-3}$alkyl)C$_{1-3}$alkyl or C$_{1-3}$alkyl.

In another embodiment, in conjunction with any one of the above and below embodiments, Y is =N—.

In another embodiment, in conjunction with any one of the above and below embodiments, R$^{10}$ is independently, at each instance, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, X is =C(R$^2$)—; and Y is =C(R$^3$)—.

In another embodiment, in conjunction with any one of the above and below embodiments, R$^3$ is halo, —NH$_2$, —NHC$_{1-3}$alkyl, —N(C$_{1-3}$alkyl)C$_{1-3}$alkyl or C$_{1-3}$alkyl.

In another embodiment, in conjunction with any one of the above and below embodiments, R$^{10}$ is independently, at each instance, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)$_2$N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl)—S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^1$ is

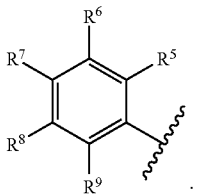

In another embodiment, in conjunction with any one of the above and below embodiments, $R^7$ is $C_{1-5}$alkyl, halo or $C_{1-4}$haloalkyl.

In another embodiment, in conjunction with any one of the above and below embodiments, $R^1$ is naphthyl substituted by 0, 1, 2 or 3 substituents independently selected from $R^5$.

In another embodiment, in conjunction with any one of the above and below embodiments, $R^1$ is $R^b$ substituted by 0, 1, 2 or 3 substituents independently selected from $R^5$.

In another embodiment, in conjunction with any one of the above and below embodiments, $R^1$ is $R^b$ substituted by 1, 2 or 3 substituents independently selected from $R^5$.

In another embodiment, in conjunction with any one of the above and below embodiments, $R^4$ is

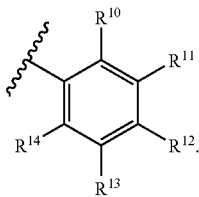

In another embodiment, in conjunction with any one of the above and below embodiments, $R^{10}$ and $R^{11}$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the each of the carbon atoms in the chain is substituted by H, =O, $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$ alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$ alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$, and any nitrogen atoms in the chain are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^a$; or $R^{11}$ and $R^{12}$ together are a saturated or unsaturated 3- or 4-atom bridge containing 0, 1, 2 or 3 atoms selected from O, N and S with the remaining atoms being carbon, so long as the combination of O and S atoms is not greater than 2, wherein the each of the carbon atoms in the chain is substituted by H, =O, $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$ alkyl), —S(=O)$_2$($C_{1-8}$alkyl), —S(=O)$_2$NR$^a$R$^a$, —S(=O)$_2$ N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$ alkylNR$^a$R$^a$ and —NR$^a$C$_{2-6}$alkylOR$^a$, and any nitrogen atoms in the chain are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$.

In another embodiment, in conjunction with any one of the above and below embodiments, $R^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from $C_{1-8}$alkyl, $C_{1-14}$haloalkyl, halo, nitro, cyano, oxo, —OR$^a$, —S(=O)$_n$C$_{1-6}$alkyl, —OC$_{1-4}$haloalkyl, —OC$_{2-6}$alkylNR$^a$R$^a$, —OC$_{2-6}$alkylOR$^a$, —OC$_{1-6}$alkylC(=O)OR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —C(=O)C$_{1-6}$ alkyl, —C(=O)OC$_{1-6}$alkyl, —OC(=O)C$_{1-6}$alkyl, —C(=O)NR$^a$C$_{1-6}$alkyl and —NR$^a$C(=O)C$_{1-6}$alkyl; and unsaturated carbon atoms may be additionally substituted by =O; and any nitrogen atoms in the chain are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$.

In another embodiment, in conjunction with any one of the above and below embodiments, $R^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 1, 2 or 3 substituents independently selected from $C_{1-8}$alkyl, $C_{1-4}$haloalkyl, halo, nitro, cyano, oxo, —OR$^a$, —S(=O)$_n$C$_{1-6}$alkyl, —OC$_{1-4}$haloalkyl, —OC$_{2-6}$alkylNR$^a$R$^a$, —OC$_{2-6}$alkylOR$^a$, —OC$_{1-6}$alkylC(=O)OR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —C(=O)C$_{1-6}$ alkyl, —C(=O)OC$_{1-6}$alkyl, —OC(=O)C$_{1-6}$alkyl, —C(=O)NR$^a$C$_{1-6}$alkyl and —NR$^a$C(=O)C$_{1-6}$alkyl; and unsaturated carbon atoms may be additionally substituted by =O; and any nitrogen atoms in the chain are substituted by H, —C$_{1-6}$alkylOR$^a$, —C$_{1-6}$alkyl, —C$_{1-6}$alkylNR$^a$R$^a$, —C$_{1-3}$alkylC(=O)OR$^a$, —C$_{1-3}$alkylC(=O)NR$^a$R$^a$, —C$_{1-3}$alkylOC(=O)C$_{1-6}$alkyl, —C$_{1-3}$alkylNR$^a$C(=O)C$_{1-6}$alkyl, —C(=O)R$^c$ or —C$_{1-3}$alkylR$^c$.

In another embodiment, in conjunction with any one of the above and below embodiments, $R^4$ is 10-membered bicyclic ring comprising fused 6-membered rings, containing 0, 1, 2, 3 or 4 N atoms with the remainder being carbon atoms, with at least one of the 6-membered rings being aromatic, wherein the carbon atoms are substituted by H, halo, OR$^a$, NR$^a$R$^a$, $C_{1-6}$alkyl and $C_{1-3}$haloalkyl; and unsaturated carbon atoms may be additionally substituted by =O.

In another embodiment, in conjunction with any one of the above and below embodiments, $R^4$ is 10-membered bicyclic ring comprising fused 6-membered rings, containing 1, 2, 3 or 4 N atoms with the remainder being carbon atoms, with at least one of the 6-membered rings being aromatic, wherein the carbon atoms are substituted by H, halo, $OR^a$, $NR^aR^a$, $C_{1-6}$alkyl and $C_{1-3}$haloalkyl; and unsaturated carbon atoms may be additionally substituted by $=O$.

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to any of the above embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

Another aspect of the invention relates to a method of making a compound according to the above embodiments, comprising the step of: reacting

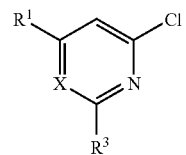

with $R^2NH_2$ to form

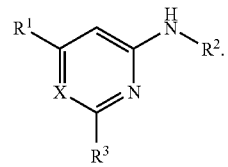

The compounds of this invention may have in general several asymmetric centers and are typically depicted in the form of racemic mixtures. This invention is intended to encompass racemic mixtures, partially racemic mixtures and separate enantiomers and diastereomers.

Unless otherwise specified, the following definitions apply to terms found in the specification and claims:

"$C_{\alpha-\beta,N}$alkyl" means an alkyl group comprising a minimum of $\alpha$ and a maximum of $\beta$ carbon atoms in a branched, cyclical or linear relationship or any combination of the three, wherein $\alpha$ and $\beta$ represent integers. The alkyl groups described in this section may also contain one or two double or triple bonds. Examples of $C_{1-6}$alkyl include, but are not limited to the following:

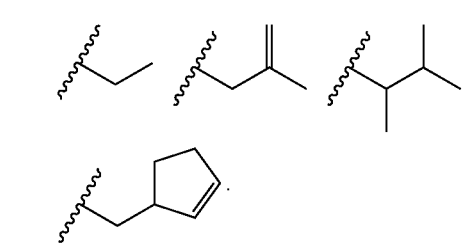

"Benzo group", alone or in combination, means the divalent radical $C_4H_4=$, one representation of which is $—CH=CH—CH=CH—$, that when vicinally attached to another ring forms a benzene-like ring—for example tetrahydronaphthylene, indole and the like.

"Halo" or "halogen" means a halogen atoms selected from F, Cl, Br and I.

"$C_{V-W}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

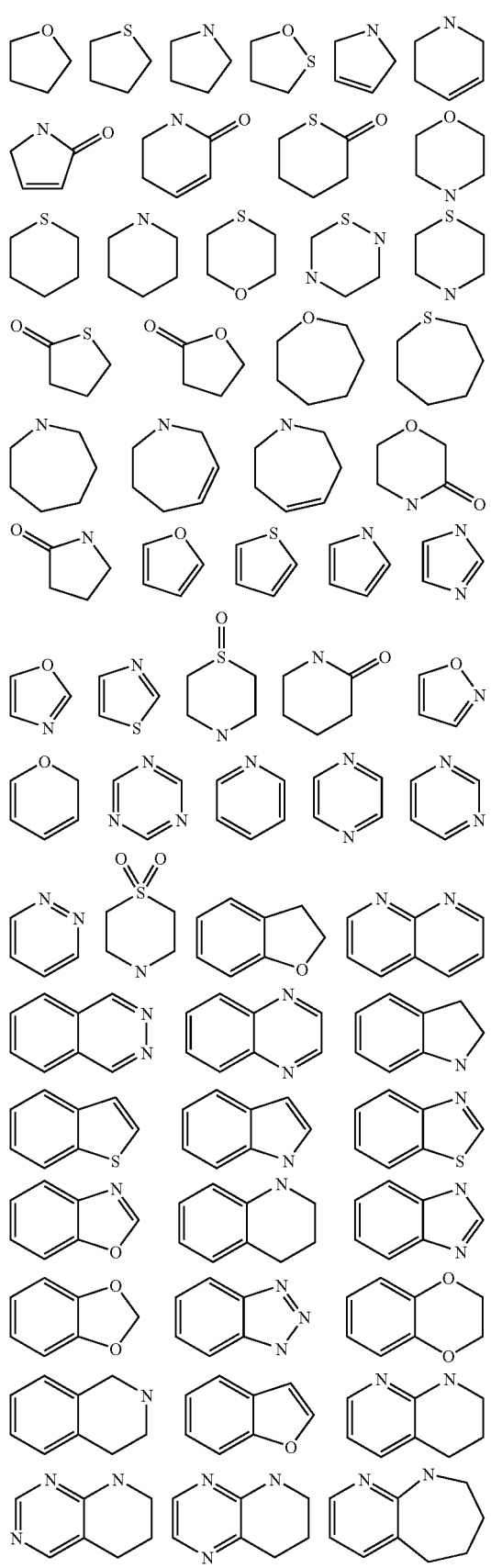
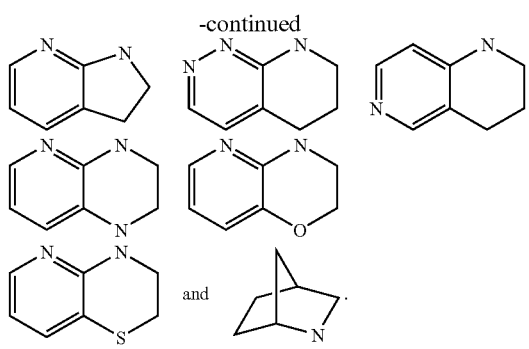

and

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, alkyl, substituted alkyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene) benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

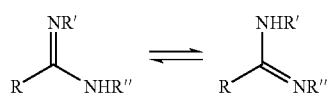

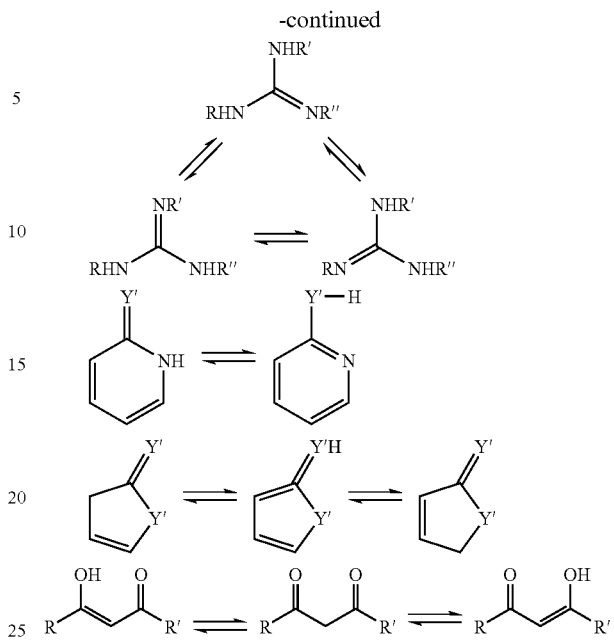

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species, embodiments and sub-embodiments using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

EXPERIMENTAL

General

Unless otherwise noted, all materials were obtained from commercial suppliers and used without further purification. All parts are by weight and temperatures are in degrees centigrade unless otherwise indicated. All compounds showed NMR spectra consistent with their assigned structures. Melting points were determined on a Buchi apparatus and are uncorrected. Mass spectral data was determined by electrospray ionization technique. All examples were purified to >95% purity as determined by high-performance liquid chromatography. Unless otherwise stated, reactions were run at room temperature. Microwave reactions were conducted using a Smith Synthesizer® (Personal Chemistry, Inc., Upssala, Sweden) apparatus.

The following abbreviations are used:
aq—aqueous
BINAP—2,2'-bis(diphenylphosphino)-1,1'-binaphthyl
brine—saturated aqueous NaCl
concd—concentrated
DMF—N,N-dimethylformamide
$Et_2O$—diethyl ether
BSA—N,O-bis(trimethylsilyl)acetamide
BSTFA—N,O-bis(trimethylsilyl)trifluoroacetamide
NMP N-methylpyrrolidinone
EtOAc—ethyl acetate
EtOH—ethyl alcohol
h—hour
min—minutes
MeOH—methyl alcohol
satd—saturated
THF—tetrahydrofuran
TLC— thin layer chromatography Scheme I
Generic Schemes for the preparation of pyrimidine core:

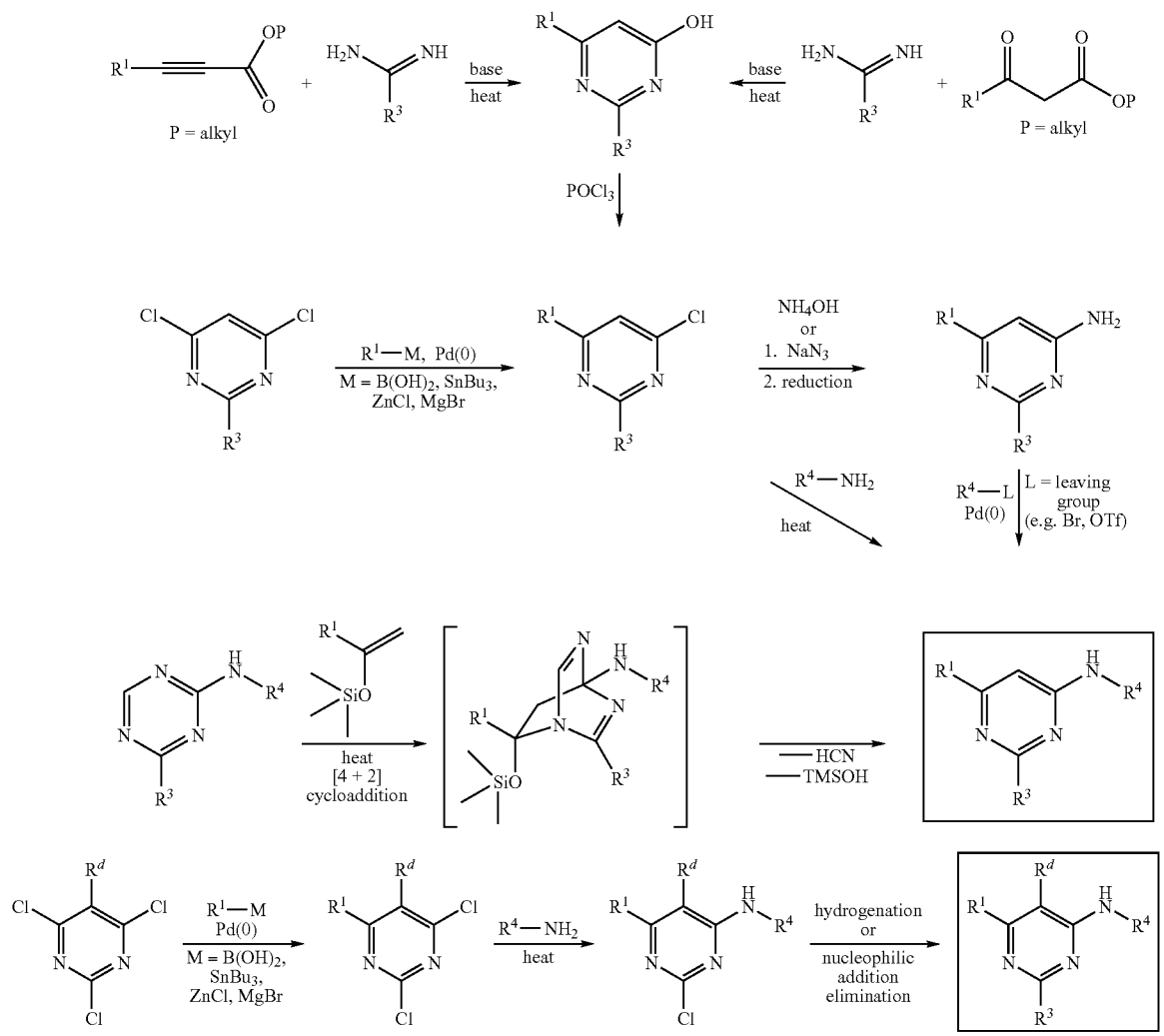

-continued

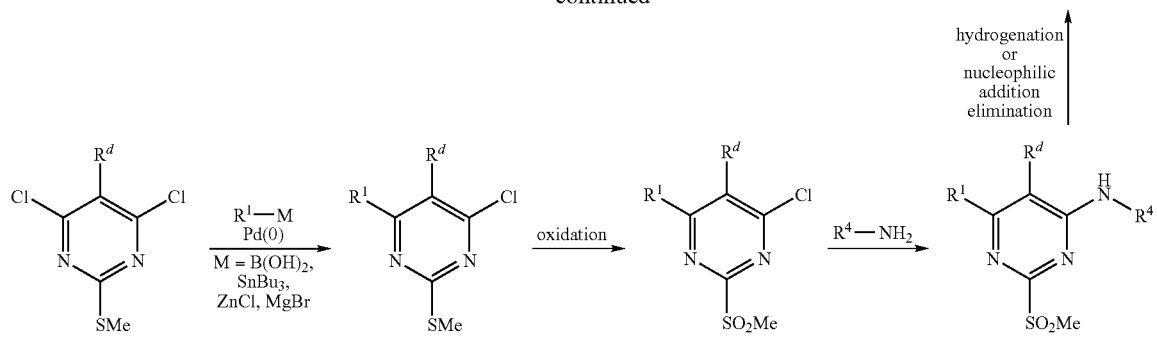

Example 1

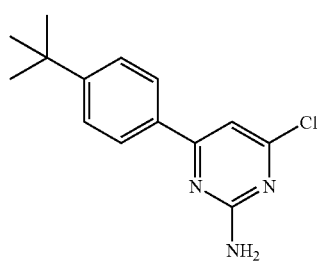

(a) 4-(4-tert-Butylphenyl)-6-chloropyrimidin-2-ylamine. To a 250-mL, round-bottomed flask containing 2-amino-4,6-dichloropyrimidine (0.88 g, 5.4 mmol, Lancaster) in $CH_3CN$ (35 mL), was added 4-tert-butylphenylboronic acid (0.80 g, 4.5 mmol, Aldrich) and $Pd(PPh_3)_4$ (0.26 g, 0.23 mmol, Aldrich). A solution of 10% $Na_2CO_3$ (20 mL) was added and the resulting mixture was stirred at 90° C. for 10 h under a $N_2$ atmosphere. The reaction mixture was allowed to cool to room temperature. The organic phase was collected and dried over $Na_2SO_4$. The solution was filtered and the concentrated in vacuo to afford the crude product, and column chromatography over silica gel with hexane: EtOAc (3:1) gave the desired product as a clear oil. MS (ESI, pos. ion) m/z: 262 (M+1).

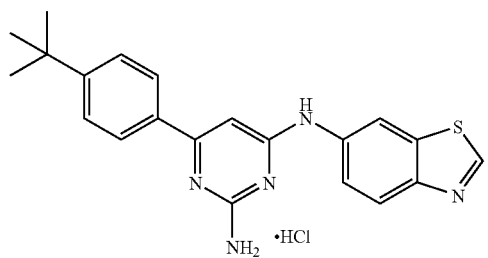

(b) $N^4$-Benzothiazol-6-yl-6-(4-tert-butylphenyl)pyrimidine-2,4-diamine Hydrochloride. To a 25-mL, round-bottomed flask containing 4-(4-tert-butylphenyl)-6-chloropyrimidin-2-ylamine (0.16 g, 0.59 mmol), was added 6-aminobenzothiazole (0.11 g, 0.71 mmol, Lancaster) and EtOH (8 mL). The solution was heated at reflux for 20 h under a $N_2$ atmosphere. The mixture was concentrated in vacuo and the residue was taken in a solvent mixture (20 mL, 1:1 of MeOH:$CH_2Cl_2$). The solution was filtered and the concentrated in vacuo to afford the product (50 mg, 23%) as a white solid. The formation of hydrochloride salt was achieved by re-dissolving the product solid (50 mg, 0.13 mmol) in a solvent mixture (8 mL, 1:1 v/v, MeOH:$CH_2Cl_2$), adding a solution of HCl (0.14 mL, 0.14 mmol, 1.0 N in $Et_2O$, Aldrich), and concentrating the solution in vacuo. The title compound was obtained as an off-white solid. MP: 220-222° C. MS (ESI, pos. ion.) m/z: 376 (M+1).

Example 2

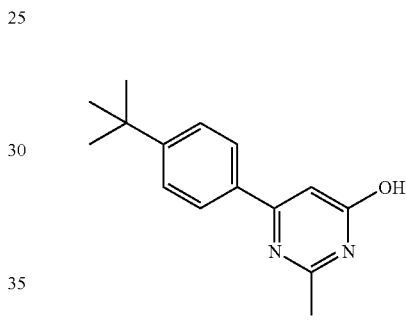

(a) 6-(4-tert-Butylphenyl)-2-methylpyrimidin-4-ol. To a 250-mL, round-bottomed flask was added ethyl 3-(4-tert-butylphenyl)prop-2-ynoate (1.5 g, 6.5 mmol), EtOH (50 mL), acetamidine hydrochloride (1.5 g, 16 mmol, Aldrich) and sodium ethoxide (1.6 g, 23 mmol, Aldrich). The resulting solution was heated at reflux under $N_2$ for 16 h. The reaction mixture was allowed to cool to 25° C., the solvent was removed in vacuo, and the residue was treated with EtOAc (100 mL) and water (25 mL). The mixture was acidified to pH~4.0 with 2 N HCl. The organic phase was separated and washed with water (20 mL), dried over $Na_2SO_4$, filtered and concentrated in vacuo. Purification by silica gel chromatography (step gradient, 1:1 hexane/EtOAc, then 20:20:1 hexane/EtOAc/MeOH) provided the title product as a white solid. MS (ESI, pos. ion) m/z: 243 (M+1).

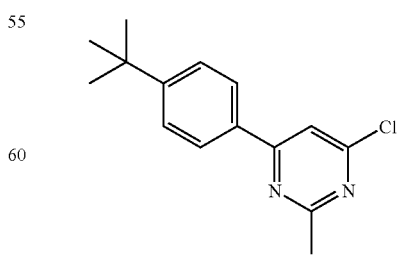

(b) 6-(4-tert-Butylphenyl)-4-chloro-2-methylpyrimidine. To a 100-mL, round-bottomed flask was added 6-(4-tertbutylphenyl)-2-methylpyrimidin-4-ol (0.15 g, 0.62 mmol) and phosphorus oxychloride (8.0 mL, 86 mmol, Aldrich). The resulting solution was heated at reflux under $N_2$ for 3 h. The solution was concentrated in vacuo to provide the title product as a yellow oil. MS (ESI, pos. ion) m/z: 261 (M+1).

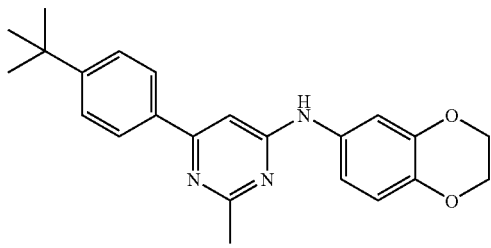

(c) [6-(4-tert-Butylphenyl)-2-methylpyrimidin-4-yl]-(2,3-dihydrobenzo[1,4]-dioxin-6-yl)amine. To a 100-mL, round-bottomed flask containing 6-(4-(tert-butylphenyl)-4-chloro-2-methylpyrimidine (0.14 g, 0.60 mmol) in 1,4-dioxane (8 mL) was added 1,4-benzodioxane-6-amine (0.11 g, 0.72 mmol, Aldrich). The reaction mixture was heated at reflux under $N_2$ for 5 h. The solvent was removed in vacuo and the crude product was purified by silica gel chromatography (3:1 hexane/EtOAc) to afford the title product as a yellow oil. MS (ESI, pos. ion) m/z: 376 (M+1).

Example 3

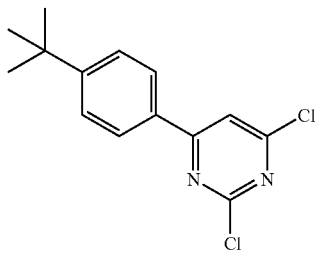

(a) 6-(4-tert-Butylphenyl)-2,4-dichloropyrimidine. (Analogous to the procedures of Finch, H. *J. Chem. Soc., Perkin Trans.* 1 1994, 9, 1193; Gong, Y. *Synlett* 2000, 6, 829). To a 250-mL, round-bottomed flask containing 2,4,6-trichloropyrimidine (26 g, 0.14 mol, Aldrich) in $CH_3CN$ (100 mL) was added 4-tert-butylphenylboronic acid (7.2 g, 40 mmol, Aldrich) and $Pd(PPh_3)_4$ (1.4 g, 1.2 mmol, Aldrich). The mixture was treated with 10% aq $Na_2CO_3$ (60 mL) then magnetically stirred under $N_2$ at 90° C. overnight. The reaction mixture was diluted with EtOAc (80 mL), $CH_3CN$ (50 mL) and water (50 mL). The mixture was allowed to cool to 25° C. and the resulting precipitate was collected by filtration. The precipitate was dissolved in $CH_2Cl_2$ (140 mL), washed with satd NaCl (60 mL), dried over $Na_2SO_4$, filtered and concentrated in vacuo. Purification by silica gel chromatography (6:1 hexane/EtOAc) provided the title product. MS (ESI, pos. ion) m/z: 281 (M+1).

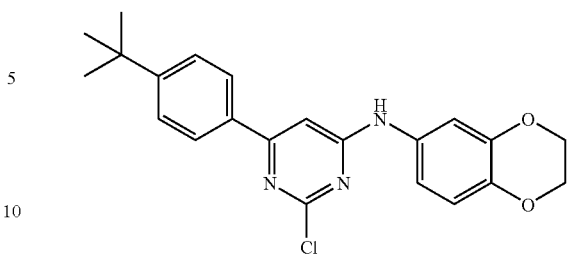

(b) [6-(4-tert-Butylphenyl)-2-chloropyrimidin-4-yl]-(2,3-dihydrobenzo[1,4]-dioxin-6-yl)amine. (Analogous to the procedure of Abdel-Fattah, A. *J. Chem. Res. Synop.* 1994, 11, 412). To a 250-mL, round-bottomed flask containing 6-(4-tert-butylphenyl)-2,4-dichloropyrimidine (3.0 g, 11 mmol) in 1:1 EtOH/1,4-dioxane (100 mL) was added 1,4-benzodioxane-6-amine (1.3 g, 8.6 mmol, Aldrich). The reaction mixture was stirred at 25° C. overnight and the solvent was removed in vacuo. Purification by silica gel chromatography (6:1 hexane/EtOAc) provided the title product as an off-white solid. MS (ESI, pos. ion) m/z: 396 (M+1).

Example 4

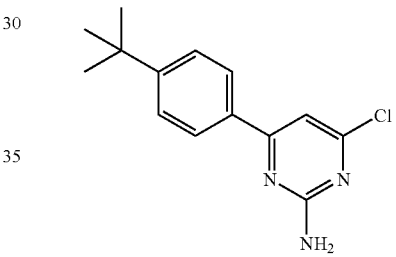

(a) 6-(4-tert-Butylphenyl)-4-chloropyrimidine-2-ylamine. To a 100-mL, round-bottomed flask containing 4,6-dichloro-2-aminopyrimidine (0.87 g, 5.4 mmol, Aldrich) in 35 mL $CH_3CN$ were added 4-tert-butylphenylboronic acid (0.80 g, 4.5 mmol, Aldrich) and $Pd(PPh_3)_4$ (0.26 g, 0.23 mmol, Aldrich). 10% aq $Na_2CO_3$ (20 mL) was added and the mixture was stirred under $N_2$ at 90° C. overnight. The organic phase was collected and dried over $Na_2SO_4$. Purification by silica gel chromatography with hexane/EtOAc (3:1) gave the desired product as a clear oil. MS (ESI, pos. ion) m/z: 262 (M+1).

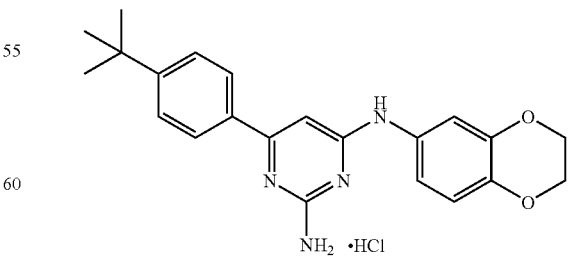

(b) [2-Amino-6-(4-tert-butylphenyl)pyrimidin-4-yl]-(2,3-dihydrobenzo[1,4]-dioxin-6-yl)amine hydrochloride. To a 250-mL, round-bottomed flask containing 6-(4-tert-butylphenyl)-4-chloropyrimidin-2-ylamine (0.16 g, 0.59 mmol) in EtOH (8 mL), was added 1,4-benzodioxane-6-amine (0.11 g, 0.71 mmol, Aldrich). The solution was refluxed for 8 h and the solvent was removed in vacuo. Purification of the residue by silica gel chromatography (10:10:1 hexane/EtOAc/MeOH) afforded the title compound as a free base (0.13 g, 57%). The hydrochloride salt was prepared by dissolving the free base (0.13 g, 0.35 mmol) in MeOH (8 mL). To the solution was added HCl (0.35 mL, 0.35 mmol, 1.0 M HCl in Et$_2$O, Aldrich), the mixture was stirred at 25° C. for 10 min, and the solvent was removed in vacuo to provide the title product. MP: 221-224° C. MS (ESI, pos. ion) m/z: 377 (M+1).

Example 5

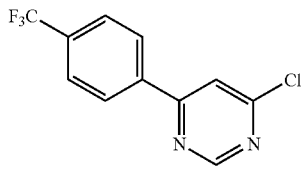

(a) 4-Chloro-6-(4-trifluoromethylphenyl)pyrimidine.

To a 500-mL, round-bottomed flask was added 4,6-dichloropyrimidine (14 g, 95 mmol, Aldrich), 4-(trifluoromethyl)phenylboronic acid (6.0 g, 32 mmol, Aldrich), acetonitrile (95 mL) and 1 M aq sodium carbonate (95 mL). The mixture was deoxygenated by sparging with N$_2$ for 15 min. The catalyst, Pd(PPh$_3$)$_4$ (1.9 g, 1.6 mmol, Strem), was added and the yellow mixture was heated at 80° C. for 15 h. After cooling to 25° C., the solution was concentrated to remove the acetonitrile. The solution was diluted with aq NaHCO$_3$ and extracted with CH$_2$Cl$_2$. The combined extracts were dried over Na$_2$SO$_4$, filtered and concentrated in vacuo. Purification by silica gel chromatography with gradient from 1.5% to 10% solution of ethyl acetate in hexane afforded the title compound as a white solid. MS (ESI, pos. ion) m/z: 259 (M+1).

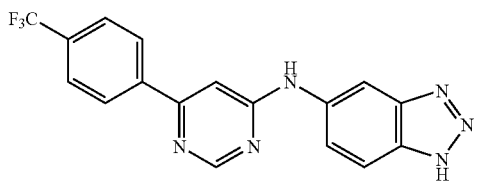

(b) (1H-Benzotriazol-5-yl)-[6-(4-trifluoromethylphenyl)pyrimidin-4-yl]amine.

A mixture of 4-chloro-6-(4-trifluoromethylphenyl)pyrimidine (0.10 g, 0.39 mmol), 5-aminobenzotriazole (0.052 g, 0.39 mmol, Lancaster) and ethanol (1 mL) was heated in a microwave at 180° C. for 20 min. The mixture was diluted with satd NaHCO$_3$ and extracted with EtOAc. The combined extracts were dried over Na$_2$SO$_4$, filtered and concentrated in vacuo. Purification by silica gel chromatography with gradient from 30% to 70% solution of ethyl acetate in hexane afforded the product as a yellow solid. MS (ESI, pos. ion) m/z: 357 (M+1).

Example 6

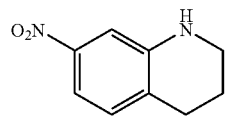

(a) 7-Nitro-1,2,3,4-tetrahydroquinoline. 1,2,3,4-Tetrahydroquinoline (19 mL, 0.15 mol, Aldrich) was added dropwise into concd H$_2$SO$_4$ (54 mL) with stirring over 30 min at 0° C. To the solution was then added dropwise with stirring a mixture of concd H$_2$SO$_4$ (30 mL) and 90% HNO$_3$ (6.4 mL, 0.17 mol) for about 2.5 h while the internal reaction temperature was maintained at 5-10° C. by cooling with an ice bath. The reaction mixture was stirred for 2.5 h and allowed to warm slowly to 25° C. The mixture was then added to crushed ice (~1 L) and treated with solid KOH, with stirring, until pH 8 was reached. The resulting suspension was filtered and the filtrate was washed with EtOAc (1.5 L). The aqueous phase was extracted with EtOAc (2×500 mL), the EtOAc phases were combined, washed with 1 N NaOH (1 L) and satd NaCl (500 mL), dried over MgSO$_4$, filtered and concentrated in vacuo. Purification by silica gel chromatography (8:1 hexane/EtOAc) afforded the title compound as bright-orange crystals. MS (ESI, pos. ion) m/z 179 (M+1).

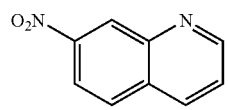

(b) 7-Nitroquinoline. A solution of 7-nitro-1,2,3,4-tetrahydroquinoline (4.0 g, 22 mmol) in dichloromethane (500 mL) was stirred at 25° C. and treated with 2,3-dichloro-5,6-dicyano-1,4-benzoquinone (10 g, 44 mmol, Aldrich) in portions. The reaction mixture was stirred at 25° C. for 1 h, then filtered and the filtercake was washed with dichloromethane. The filtrate was concentrated to give a brown solid (4.4 g). The crude product was dissolved in hot EtOAc (200 mL), treated with decolorizing carbon (1 g), filtered though Celite®, and concentrated. Recrystallization from EtOAc provided the title product as an orange-tan solid. Purification of the concentrated mother liquors by silica gel chromatography (25% EtOAc/hexane) provided an additional amount of the title product as an off-white solid.

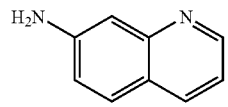

(c) 7-Quinolylamine. A solution of 7-nitroquinoline (3.2 g, 18 mmol) in MeOH (200 mL) was purged with N$_2$ and treated with 10% palladium on carbon (1.0 g, Aldrich). The suspension was purged with H$_2$ and magnetically stirred under 1 atmosphere H$_2$ for 16 h. The mixture was purged with N$_2$, filtered though Celite® and concentrated in vacuo. Purification by silica gel chromatography with gradient from 5% to 10% solution of MeOH in dichloromethane provided the title product as a brown solid. MS (ESI, pos. ion) m/z 145 (M+1).

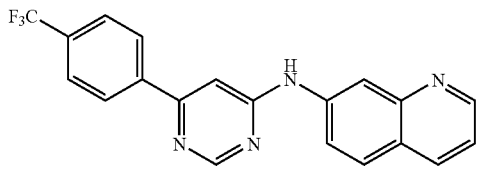

(d) Quinolyl-7-yl-[6-(4-trifluoromethylphenyl)pyrimidin-4-yl]amine. To a glass vial with a magnetic stir bar was added 4-chloro-6-(4-trifluoromethyl-phenyl)pyrimidine, Example 5(a), (0.30 g, 1.2 mmol,) and 7-quinolylamine (0.17 g, 1.2 mmol). The solids were stirred and heated in a microwave at 200° C. for 10 min. The resulting solid was partitioned between satd NaHCO$_3$ (100 mL) and EtOAc (200 mL). The organic phase was washed with satd NaCl (50 mL), dried over Na$_2$SO$_4$, filtered and concentrated in vacuo. The crude product was purified by silica gel chromatography (60% ethyl acetate/hexane), purified again by silica gel chromatography (50% EtOAc/dichloromethane) and concentrated to a solid, which was triturated with 1:1 CH$_2$Cl$_2$/hexane (50 mL). The solid was dried in vacuo at 60° C. overnight to afford the title product as a pale-tan solid. MP: 260° C. MS (ESI, pos. ion) m/z: 367 (M+1).

Example 7

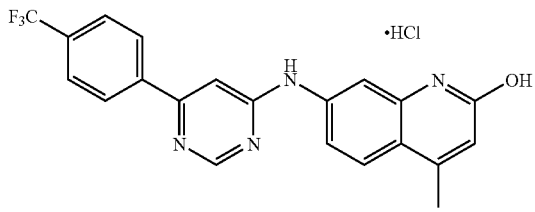

4-Methyl-7-{[6-(4-trifluoromethylphenyl)pyrimidin-4-yl]amino} quinolin-2-ol, Hydrochloride. Analogous to the procedure used to prepare Example 5(b), 4-chloro-6-(4-trifluoromethylphenyl)pyrimidine, Example 5(a), (150 mg, 0.58 mmol) and carbostyril 124 (50 mg, 0.29 mmol, Aldrich) afforded, after recrystallization from MeOH, the title product as bright-yellow crystals. MP: 373° C. (with decomposition). MS (ESI, pos. ion) m/z: 397 (M+1).

Example 8

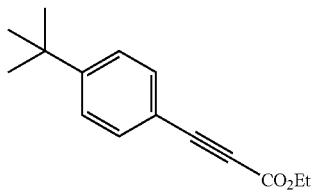

(a) Ethyl 3-(4-tert-butylphenyl)prop-2-ynoate. To a 500-mL, round-bottomed flask containing a solution of 4-tert-butylphenylacetylene (10 g, 64 mmol, GFS Chemicals) in THF (150 mL) was added n-butyllithium (40 mL, 64 mmol, 1.6 M in hexane, Aldrich) with stirring at −78° C. After the addition was complete, the reaction mixture was stirred at −78° C. for 40 min. The solution was then allowed to warm to 0° C. and stirred for 30 min. The solution was cooled to −78° C. and treated with ethyl chloroformate (6.1 mL, 64 mmol, Aldrich). After stirring for 2 h, the solution was allowed to warm to 25° C. and stirred overnight. The reaction was quenched with 5% aq NaHCO$_3$ (80 mL) and satd NaCl (80 mL) and extracted with EtOAc (2×130 mL). The combined extracts were washed with water (2×15 mL), dried over Na$_2$SO$_4$, filtered and concentrated in vacuo. Purification by silica gel chromatography (20:1 hexane/EtOAc) provided the title product. MS (ESI, pos. ion) m/z: 231 (M+1).

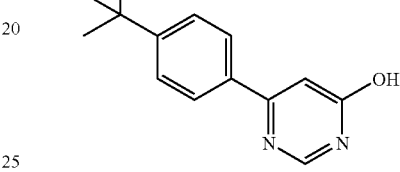

(b) 6-[4-tert-Butylphenyl)pyrimidin-4-ol. (Analogous to the procedure of Haddach, M. *J. Fluorine Chem.* 1991, 51, 197). To a 250-mL, round-bottomed flask was added ethyl 3-(4-tert-butylphenyl)prop-2-ynoate (1.9 g, 8.4 mmol), EtOH (100 mL), formamidine hydrochloride (10 g, 0.13 mol, Aldrich) and diisopropylethylamine (22 mL, 0.13 mol, Aldrich). The solution was heated at reflux under N$_2$ for 6 h. The reaction mixture was allowed to cool to 25° C., the solvent was removed in vacuo, and the residue was heated at 170° C. under N$_2$ for 2 h. The residue was allowed to cool to 25° C. and dissolved in EtOH (15 mL). The solution was treated with sodium ethoxide (15 mL, 21 wt %, 46 mmol, Aldrich), then heated at reflux under N$_2$ for 4 h. The reaction mixture was diluted with EtOAc (100 mL) and acidified to pH 4.0 with 2 N HCl. The organic phase was separated and washed with water (50 mL), dried over Na$_2$SO$_4$, filtered and concentrated in vacuo. Purification by silica gel chromatography (step gradient, 1:1 hexane/EtOAc then 20:20:1 hexane/EtOAc/MeOH) provided the title product as an off-white solid. MS (ESI, pos. ion) m/z: 229 (M+1).

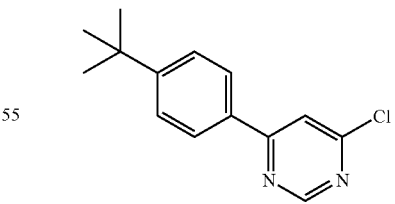

(c) 6-(4-tert-Butylphenyl)-4-chloropyrimidine. To a 100-mL, round-bottomed flask was added 6-(4-tert-butylphenyl)pyrimidin-4-ol (0.73 g, 3.2 mmol) and phosphorus oxychloride (25 mL, 0.27 mol, Aldrich). The resulting solution was heated at reflux under N$_2$ for 3 h. The solution was concentrated in vacuo to provide the title product as a yellow oil. MS (ESI, pos. ion) m/z: 247 (M+1).

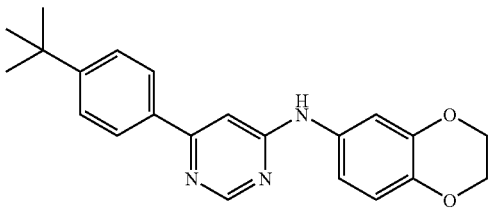

(d) [6-(4-tert-Butylphenyl)pyrimidin-4-yl]-(2,3-dihydrobenzo[1,4]dioxin-6-yl)amine. To a 100-mL, round-bottomed flask containing 6-(4-tert-butylphenyl)-4-chloropyrimidine (0.25 g, 1.0 mmol) in 1,4-dioxane (5 mL), was added 1,4-benzodioxane-6-amine (0.15 g, 1.0 mmol, Aldrich). The solution was heated at reflux under $N_2$ for 3 h. The solvent was removed in vacuo and the residue was purified by silica gel chromatography (2:1 hexane/EtOAc) to provide the title product as an off-white solid. MS (ESI, pos. ion) m/z: 362 (M+1). MP: 199-202° C.

Example 9

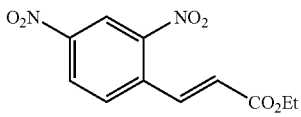

(a) Ethyl 3-(2,4-dinitrophenyl)prop-2-enoate. A mixture of 2,4-dinitrobenz-aldehyde (10 g, 51 mmol, Avocado) and methyl (triphenylphosphoranylidene)-acetate (17 g, 51 mmol, Aldrich) in benzene (200 mL) was heated at reflux with stirring under $N_2$ for 3 h. The reaction mixture was allowed to cool to 25° C. and diluted with $Et_2O$ (500 mL). The mixture was washed with water (3×200 mL) and satd NaCl (100 mL), dried over $MgSO_4$, filtered and concentrated in vacuo. Purification by silica gel chromatography (4:1 hexane/EtOAc) provided the title product as a bright-yellow solid.

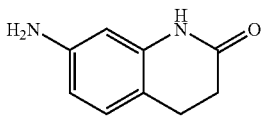

(b) 7-Amino-3,4-dihydro-1H-quinolin-2-one. To a solution of ethyl 3-(2,4-dinitrophenyl)prop-2-enoate (10 g, 38 mmol) in EtOH (150 mL) and glacial acetic acid (10 mL) was added 10% palladium on carbon (5.0 g, Aldrich), and the mixture was hydrogenated on a Parr shaker apparatus at 25° C., under 60 psi $H_2$, for 6 h. The reaction mixture was purged with $N_2$, filtered though Celite® and the filtercake was washed with EtOH (400 mL). The filtrate was concentrated in vacuo to provide the title product as a yellow solid. MS (ESI, pos. ion) m/z: 163 (M+1).

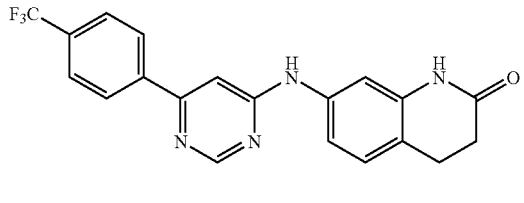

(c) 3,4-Dihydro-7-[6-(4-trifluoromethylphenyl)pyrimidin-4-ylamino]-1H-quinolin-2-one. A mixture of 4-chloro-6-(4-trifluoromethylphenyl)pyrimidine, Example 5(a), (3.2 g, 12 mmol) and 7-amino-1,3,4-trihydroquinolin-2-one (1.0 g, 6.2 mmol) in EtOH (20 mL) was stirred at reflux for 4.5 h. The resulting suspension was allowed to cool to 25° C., then diluted with EtOAc (100 mL). The solid was collected by filtration, washed with EtOAc (30 mL) and hexane (30 mL), and dried in vacuo to afford 2.9 g (97%) 7-[6-(4-(trifluoromethylphenyl)-pyrimidin-4-ylamino]-3,4-dihydro-1H-quinolin-2-one hydrochloride as a bright-yellow solid. A portion of the solid (460 mg, 1.1 mmol) was partitioned between EtOAc (200 mL) and 1 N NaOH (100 mL). The organic phase was separated and washed with water (50 mL) and satd NaCl (50 mL), then dried in vacuo onto silica gel. Purification by silica gel chromatography (5% MeOH/dichloro-methane) provided 380 mg (90%) of the title product as an amorphous off-white solid. MS (ESI, pos. ion) m/z: 385 (M+1).

Example 10

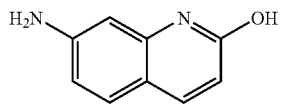

(a) 7-Aminoquinolin-2-ol. 7-Amino-3,4-dihydro-1H-quinolin-2-one, Example 9(b), (1.0 g, 6.2 mmol) was suspended in anhydrous 1,4-dioxane (20 mL), under $N_2$, in a flame-dried, round-bottomed flask equipped with a reflux condenser. The suspension was magnetically stirred at 25° C. and treated with 2,3-dichloro-5,6-dicyano-1,4-benzoquinone (1.7 g, 7.5 mmol, Aldrich) followed by N,O-bis(trimethylsilyl)acetamide (7.6 mL, 3.1 mmol, Aldrich). The reaction mixture was stirred in a 105° C. oil bath for 45 min, then filtered while hot through a fine sintered-glass funnel. The filtrate was concentrated in vacuo, then filtered though a short plug of silica gel (5% MeOH in dichloromethane) and concentrated again to provide 3.1 g of a brown solid. The solid was dissolved in 1 N HCl and washed with EtOAc. The pH of the aqueous phase was adjusted to ~5 by the addition of 5 N NaOH and glacial acetic acid. The solution was saturated with NaCl and extracted with n-butanol until the aqueous phase appeared to be free of product by TLC. The combined n-butanol extracts were concentrated in vacuo. Purification of the residue by silica gel chromatography (5% MeOH in dichloromethane) provided 180 mg (18%) of the title product as a pale orange solid. MS (ESI, pos. ion) m/z: 161 (M+1).

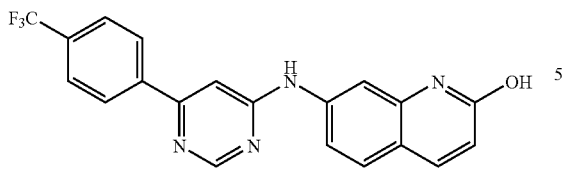

(b) 7-[6-(4-Trifluoromethylphenyl)pyrimidin-4-ylamino]quinolin-2-ol. A mixture of 4-chloro-6-(4-trifluoromethylphenyl)pyrimidine, Example 5(a), (0.48 g, 1.9 mmol), 7-aminoquinolin-2-ol (0.15 g, 0.94 mmol) and EtOH (1.5 mL) was stirred and heated in a microwave at 160° C. for 10 min. The resulting bright-yellow solid was collected by filtration and washed with EtOAc (30 mL) and hexane (30 mL). The solid was suspended in 1 N NaOH (100 mL), shaken vigorously, then the suspension was acidified to pH ~5 with glacial AcOH at 0° C. The resulting suspension was filtered and the solid purified by silica gel chromatography (step gradient: 5-10% MeOH in dichloromethane), recrystallized from MeOH and dichloromethane, and dried in vacuo at 80° C. to provide 255 mg (71%) of the title product as pale yellow crystals. MS (ESI, pos. ion) m/z: 383 (M+1). MP: 337° C. (with decomposition).

Example 11

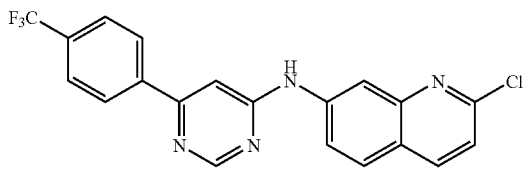

(2-Chloroquinolin-7-yl)-[6-(4-trifluoromethylphenyl)pyrimidin-4-yl]amine. 7-[6-(4-(Trifluoromethylphenyl)pyrimidin-4-ylamino]-3,4-dihydro-1H-quinolin-2-one hydrochloride, Example 9(c), (500 mg, 1.2 mmol) was suspended in anhydrous 1,4-dioxane (10 mL), under $N_2$, in a flame-dried, round-bottomed flask equipped with a reflux condenser. The suspension was magnetically stirred at 25° C. and treated with 2,3-dichloro-5,6-dicyano-1,4-benzoquinone (350 mg, 1.5 mmol, Aldrich) followed by bis(trimethylsilyl)trifluoroacetamide (1.4 mL, 5.3 mmol, Aldrich). The reaction mixture was stirred in a 105° C. oil bath for 15 min, then allowed to cool to 25° C. and partitioned between EtOAc (150 mL) and 1% aq $NaHSO_3$ (100 mL). The resulting emulsion was allowed to settle, and the organic phase was separated and concentrated in vacuo to a brown solid (1.1 g). The solid was treated with phosphorous oxychloride (10 mL, Aldrich) and stirred in a 100° C. oil bath for 1 h. After cooling to room temp, the reaction was quenched by slow addition to MeOH (200 mL), then concentrated in vacuo. The residue was treated with a mixture of 30% NHOH and ice (200 mL), then extracted with EtOAc (2×100 mL). The combined organic extract was washed with satd NaCl (50 mL), dried over $Na_2SO_4$, filtered and concentrated in vacuo. Purification by silica gel chromatography (30% EtOAc in hexane) provided a mixture of the title product and (2-methoxyquinolin-7-yl)-[6-(4-trifluoromethylphenyl)pyrimidin-4-yl]amine (Example 12), and the pure title product as a white solid. MS (ESI, pos. ion) m/z: 401 (M+1). MP: 233° C.

Example 12

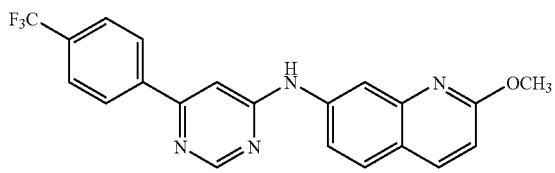

(2-Methoxyquinolin-7-yl)-[6-(4-trifluoromethylphenyl)pyrimidin-4-yl]amine.

A mixture of (2-chloroquinolin-7-yl)-[6-(4-trifluoromethylphenyl)pyrimidin-4-yl]amine and (2-methoxyquinolin-7-yl)-[6-(4-trifluoromethylphenyl)pyrimidin-4-yl]amine, Example 11, (210 mg) was dissolved in a solution of HCl in MeOH, prepared by the addition of acetyl chloride (5 mL) to MeOH (50 mL). The reaction mixture was stirred at 25° C. for 15 h, and heated at reflux for 2 h. The solution was concentrated in vacuo and the residue partitioned between EtOAc (50 mL) and 1 N NaOH (50 mL). The organic phase was washed with water (20 mL), satd NaCl (20 mL), dried over $Na_2SO_4$, filtered and concentrated in vacuo. Purification by silica gel chromatography (25% EtOAc in hexane) followed by recrystallization from EtOAc and hexane, provided the title product as white crystals. MS (ESI, pos. ion) m/z: 397 (M+1). MP: 199° C.

Example 13

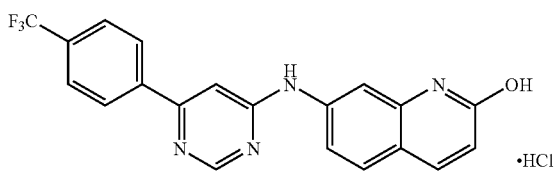

(a) 7-[6-(4-Trifluoromethylphenyl)pyrimidin-4-ylamino]quinolin-2-ol Hydrochloride. 7-[6-(4-(Trifluoromethylphenyl)pyrimidin-4-ylamino]-3,4-dihydro-1H-quinolin-2-one hydrochloride, Example 9(c), (1.0 g, 2.4 mmol) was suspended in anhydrous 1,4-dioxane (15 mL), under $N_2$, in a flame-dried, round-bottomed flask equipped with a reflux condenser. The suspension was magnetically stirred at 25° C. and treated with 2,3-dichloro-5,6-dicyano-1,4-benzoquinone (710 mg, 3.1 mmol, Aldrich) followed by bis(trimethylsilyl)trifluoroacetamide (2.8 mL, 10.5 mmol, Aldrich). The reaction mixture was stirred in a 105° C. oil bath for 75 min, then allowed to cool to 25° C. and concentrated to a volume of ~5 mL. The mixture was treated with 1 N HCl (100 mL) and EtOAc (100 mL) and shaken vigorously. The resulting fine precipitate was collected by filtration and air-dried to afford the title product as a green-tan solid. MS (ESI, pos. ion) m/z: 383 (M+1).

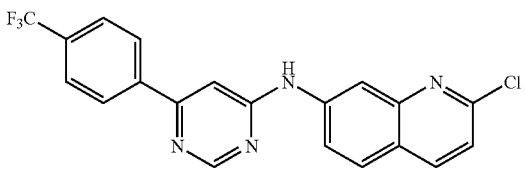

(b) (2-Chloroquinolin-7-yl)-[6-(4-trifluoromethylphenyl)pyrimidin-4-yl]amine. A mixture of 7-[6-(4-trifluoromethylphenyl)pyrimidin-4-ylamino]quinolin-2-ol hydrochloride (810 mg, 1.9 mmol) and phosphorous oxychloride (5 mL) was magnetically stirred in a 100° C. oil bath for 1 h. The reaction mixture was allowed to cool to 25° C., then added slowly to 30% NH₄OH (100 mL) diluted up to 150 mL with crushed ice. The mixture was concentrated in vacuo to ~100 mL and the resulting dark brown precipitate was collected by filtration. The aqueous phase was extracted with n-butanol (100 mL), and the extract and the precipitate were combined and concentrated in vacuo. Purification by silica gel chromatography with gradient from 10% to 30% solution of EtOAc in dichloromethane provided the title product. MS (ESI, pos. ion) m/z: 401 (M+1).

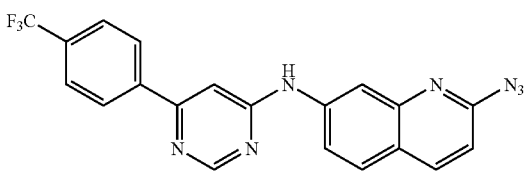

(c) (2-Azidoquinolin-7-yl)-[6-(4-trifluoromethylphenyl)pyrimidin-4-yl]amine.

A solution of (2-chloroquinolin-7-yl)-[6-(4-trifluoromethylphenyl)pyrimidin-4-yl]amine (500 mg, 1.2 mmol) in dimethyl sulfoxide (8 mL) was treated with sodium azide (810 mg, 12 mmol) and magnetically stirred in a 110° C. oil bath for 18 h. The reaction mixture was allowed to cool to 25° C. and treated with water (100 mL) and EtOAc (100 mL). The mixture was vigorously shaken and the resulting precipitate collected by filtration to provide the title product. MS (ESI, pos. ion) m/z: 408 (M+1).

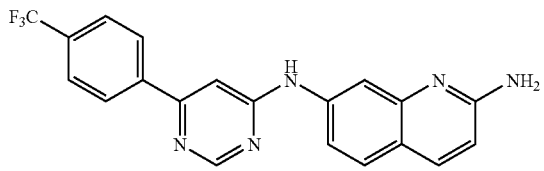

(d) N⁷-[6-(4-Trifluoromethylphenyl)pyrimidin-4-yl]quinoline-2,7-diamine. A mixture of (2-azidoquinolin-7-yl)-[6-(4-trifluoromethylphenyl)pyrimidin-4-yl]amine (425 mg, 1.0 mmol) and triphenylphosphine (330 mg, 1.3 mmol, Aldrich) in 1,4-dioxane (30 mL) was treated with water (15 mL) and concd HCl (0.5 mL). The reaction mixture was stirred at reflux for 3 h then concentrated in vacuo to ~15 mL. The mixture was treated with satd NaHCO₃ (100 mL) and extracted with EtOAc (100 mL). The organic phase was washed with water (50 mL), satd NaCl (50 mL), dried over Na₂SO₄, filtered and concentrated onto silica gel. Purification by silica gel chromatography with 5% solution of MeOH in dichloromethane followed by 5% solution of (1 M NH₃ in MeOH) in dichloromethane provided the title product as a pale-yellow amorphous solid. MS (ESI, pos. ion) m/z: 382 (M+1).

Example 14

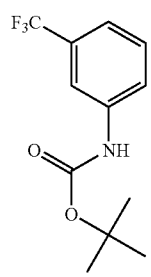

(a) (3-Trifluoromethylphenyl)carbamic acid tert-butyl ester. To a 250-mL, round-bottomed flask was added 3-(trifluoromethyl)aniline (5.0 g, 31 mmol, Aldrich), THF (100 mL), di-tert-butyl dicarbonate (20.0. g, 93 mmol, Aldrich) and 4-(dimethylamino)pyridine (0.38 g, 3.1 mmol, Aldrich). The mixture was heated at reflux for 3 h. K₂CO₃ (13 g, 93 mmol) and MeOH (50 mL) were added, and heating was continued overnight. After cooling to room temperature, the mixture was diluted with CH₂Cl₂, then filtered and washed with CH₂Cl₂ and the filtrate was concentrated to afford a brown oil. The oil was dissolved in EtOAc (200 mL) and washed with H₂O (2×100 mL), brine (1×100 mL), dried over Na₂SO₄ and concentrated in vacuo onto silica gel. Purification by silica gel chromatography with gradient from 0% to 15% solution of EtOAc in hexane afforded the title compound as a colorless oil which solidified upon standing to a while solid. MS (ESI, neg. ion.) m/z: 260 (M−1).

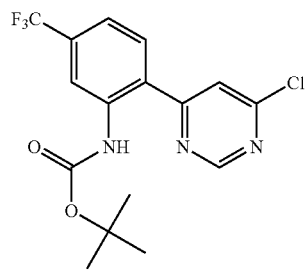

(b) [2-(6-Chloropyrimidin-4-yl)-5-trifluoromethylphenyl]carbamic acid tert-butyl ester. (Analogous to the procedures of Boisnard, S.; Carbonnelle, A. C.; Zhu, *J. Org Let.* 2001, 3, 2061-2064 and Hewawasam, P.; Meanwell, N. A. *Tetrahedron Lett.* 1994, 35, 7303). To a 500-mL, round-bottomed flask containing (3-trifluoromethylphenyl)carbamic acid tert-butyl ester (2.5 g, 9.6 mmol) in THF (100 mL) stirred at −40° C. was added sec-BuLi (17 mL, 1.3 M in cyclohexane, Aldrich) over 10 min. The mixture was stirred for 1 h at −40° C. and then cooled to −78° C. Trimethyl borate (4.4 mL, 38 mmol, Aldrich) was added over 10 min. The reaction mixture was allowed to warm to room temperature and stirred for 10 min at that temperature. The mixture was quenched with aq KH₂PO₄ and concentrated to remove the THF. The aqueous mixture was then extracted with EtOAc (3×100 mL) and the combined extracts were washed with brine, dried over Na₂SO₄, and concentrated to afford a yellow foam. The foam was dissolved in CH₃CN (30 mL) and treated with 4,6-dichloropyrimidine (4.1 g, 28 mmol, Aldrich) followed by a solution of Na₂CO₃ (2.9 g, 28 mmol) in H₂O (30 mL). Tetrakis(triphenylphosphine)palladium(0) (0.53 g, 0.46 mmol, Strem) was then added and the mixture was stirred at 75° C. for 15 h. After allowing to cool to room temperature, the mixture was concentrated in vacuo to remove the CH₃CN and then extracted with EtOAc. The combined extracts were washed with H₂O and brine, dried over Na₂SO₄ and concentrated in vacuo. Purification of the residue by silica gel chromatography with gradient from 0% to 10% solution of EtOAc in hexane afforded the title compound as a colorless oil. MS (ESI, pos. ion.) m/z: 374 (M+1).

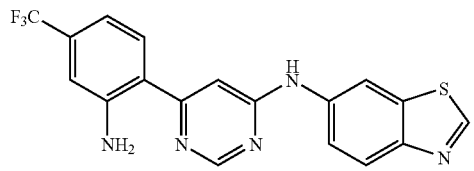

(c) [6-(2-Amino-4-trifluoromethylphenyl)pyrimidin-4-yl]benzothiazol-6-ylamine. Analogous to the procedure used to prepare Example 5(b), [2-(6-chloropyrimidin-4-yl)-5-trifluoromethylphenyl]carbamic acid tert-butyl ester (1.0 g, 2.7 mmol), and 6-aminobenzothiazole (0.80 g, 5.35 mmol, Lancaster) afforded after purification by silica gel chromatography with gradient from 0.5 to 3.0% solution of (2 M NH₃ in MeOH) in CH₂Cl₂ a crude material, which was subjected to a second purification by silica gel chromatography with gradient from 1.3% to 1.4% solution of (2 M NH₃ in MeOH) in CH₂Cl₂ to give the title compound as a yellow solid. MS (ESI, pos. ion) m/z: 388 (M+1). MP: 203.1-203.2° C.

Example 15

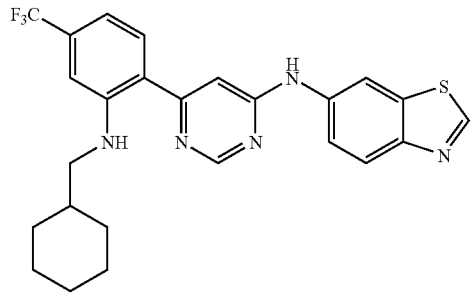

Benzothiazol-6-yl-[6-(2-cyclohexylmethylamino-4-trifluoromethylphenyl)-pyrimidin-4-yl]amine. To a 5-mL, round-bottomed flask was added [6-(2-amino-4-trifluoromethylphenyl)pyrimidin-4-yl]benzothiazol-6-ylamine (0.060 g, 0.15 mmol), 1,2-dichloroethane (1 mL), acetic acid (0.018 mL, 0.31 mmol) and cyclohexanecarboxaldehyde (0.055 mL, 0.45 mmol, Aldrich). Sodium triacetoxy-borohydride (0.083 g, 0.39 mmol, Aldrich) was added to the mixture with stirring at 0° C. and the mixture was stirring for 17 h at room temperature. The reaction mixture was diluted with EtOAc (3 mL) and quenched with H₂O (3 mL) and satd NaHCO₃ (7 mL). The phases were separated and the aqueous phase was extracted with EtOAc (3×3 mL). The combined organic extracts were washed with brine, dried over Na₂SO₄ and concentrated in vacuo onto silica gel. Purification by silica gel chromatography with gradient from 20% to 50% solution of EtOAc in hexane afforded the title compound as a yellow solid. MS (ESI, pos. ion.) m/z: 484 (M+1).

Example 16

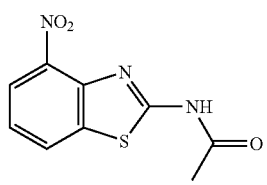

(a) N-(4-Nitrobenzothiazol-2-yl)acetamide. 4-Nitrobenzothiazol-2-ylamine (860 mg, 4.4 mmol, Helv. Chim. Acta 1940 23, 328) and acetic anhydride (10 mL, 105 mmol) were heated to 80° C. for 2 h. The reaction was cooled to room temperature and diluted with Et₂O. The solid was filtered and stirred vigorously with Et₂O. The solid was filtered again, washed with Et₂O and dried in vacuo to give the title product as a light yellow amorphous solid. MS (ESI, pos. ion.) m/z: 238 (M+1).

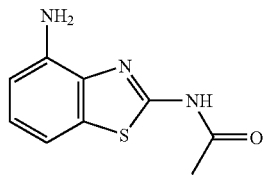

(b) N-(4-Aminobenzothiazol-2-yl)acetamide. A mixture of N-(4-nitrobenzo-thiazol-2-yl)acetamide (840 mg, 3.5 mmol), NH₄Cl (196 mg, 3.7 mmol, Aldrich) and iron dust (996 mg, 18 mmol, Aldrich) in 70% aqueous MeOH (25 mL) was heated to 65° C. After 1 h the reaction mixture was filtered while hot and the filtrate was concentrated in vacuo. The residue was purified by silica gel column chromatography with gradient from 0% to 3.5% solution of (2 M NH₃ in MeOH) in CH₂Cl₂ to give the title product as a white amorphous solid. MS (ESI, pos. ion.) m/z: 208 (M+1).

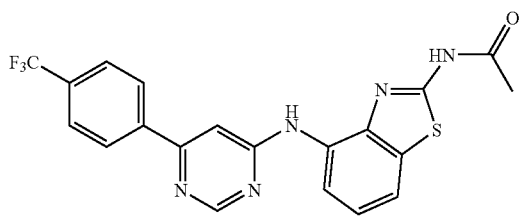

(c) N-{4-[6-(4-Trifluoromethylphenyl)pyrimidin-4-ylamino]benzothiazol-2-yl}acetamide. To a glass tube was added 4-chloro-6-(4-trifluoromethylphenyl)-pyrimidine, Example 5(a), (280 mg, 1.1 mmol), N-(4-aminobenzothiazol-2-yl)acetamide (197 mg, 0.95 mmol), CuI (55 mg, 0.30 mmol, Aldrich) and EtOH (2.5 mL). The reaction mixture was heated in a microwave at 160° C. for 15 min. The solution was decanted and purified twice by silica gel column chromatography with gradient from 0% to 4% solution of (2 M NH₃ in MeOH) in CH₂Cl₂ to give the title product as a yellow amorphous solid. MS (ESI, pos. ion.) m/z: 430 (M+1). MP: >250° C.

Example 17

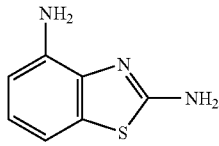

(a) Benzothiazole-2,4-diamine. This compound was prepared according to Example 16(b) using 4-nitrobenzothiazol-2-ylamine (640 mg, 3.3 mmol, *Helv. Chim. Acta* 1940 23, 328), NH₄Cl (180 mg, 3.3 mmol) and iron dust (785 mg, 14 mmol) in 75% aq MeOH (25 mL). The reaction was purified by flash column chromatography on silica gel with gradient from 0% to 5% solution of (2 M NH₃ in MeOH) in CH₂Cl₂ to give the title product as a light yellow amorphous solid. MS (ESI, pos. ion.) m/z: 166 (M+1).

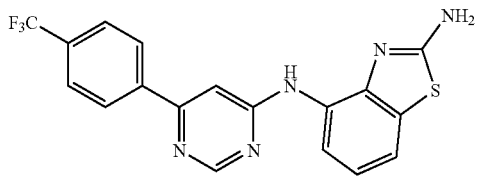

(b) N⁴-[6-(4-Trifluoromethylphenyl)pyrimidin-4-yl]benzothiazole-2,4-diamine. This compound was prepared according to Example 16(c) using 4-chloro-6-(4-trifluoromethylphenyl)pyrimidine, Example 5(a), (495 mg, 1.9 mmol), benzothiazole-2,4-diamine (320 mg, 1.9 mmol) and CuI (102 mg, 0.5 mmol) in isopropanol (4 mL) at 150° C. The reaction was purified by flash column chromatography on silica gel with gradient from 0% to 4% solution of (2 M NH₃ in MeOH) in CH₂Cl₂ to give the title product as a yellow amorphous solid. MS (ESI, pos ion.) m/z: 388 (M+1). MP: 225-227° C.

Example 18

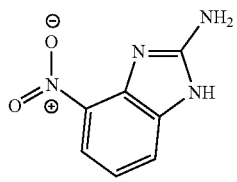

(a) 4-Nitro-1H-benzoimidazol-2-ylamine. A solution of 3-nitro-1,2-phenylenediamine (0.50 g, 3.26 mmol, Aldrich) and cyanogen bromide (0.38 g, 3.58 mmol, Aldrich) in EtOH (25 mL) was stirred for 24 h. The resulting solid was filtered and air-dried to give the title product as a reddish-brown solid. MS (ESI, pos. ion) m/z: 179 (M+1).

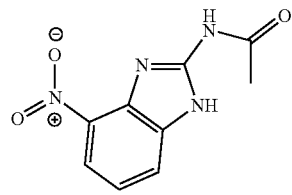

(b) N-(4-Nitro-1H-benzoimidazol-2-yl)acetamide. A mixture of 4-nitro-1H-benzoimidazol-2-ylamine (0.13 g, 0.73 mmol) in acetic anhydride (10 mL) was heated at 80° C. for 3 h. The mixture was allowed to cool to room temperature and the precipitate was filtered, washed with water and air dried to give the title product as a white solid. MS (ESI, pos. ion) m/z: 221 (M+1).

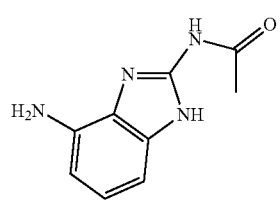

(c) N-(4-Amino-1H-benzoimidazol-2-yl)acetamide. A mixture of 10% Pd/C (0.040 g, Aldrich), N-(4-nitro-1H-benzoimidazol-2-yl)acetamide (0.090 g, 0.41 mmol) and ETOH (6 mL) was purged with nitrogen and stirred under 1 atmosphere H₂ for 18 h. The mixture was filtered through Celite® and evaporated to yield the title product as a light yellow solid. MS (ESI, pos. ion) m/z: 191 (M+1).

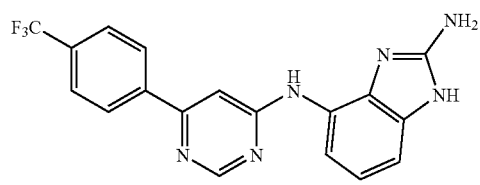

(d) N⁴-[6-(4-Trifluoromethylphenyl)pyrimidin-4-yl]-1H-benzoimidazole-2,4-diamine. A solution of N-(4-amino-1H-benzoimidazol-2-yl)acetamide (0.067 g, 0.35 mmol) and 4-chloro-6-(4-trifluoromethylphenyl)pyrimidine, Example 5(a), (0.103 g, 0.41 mmol) in ETOH (2 mL) was heated in a microwave at 175° C. with stirring for 15 min. The resulting yellow precipitate was filtered and purified by preparative HPLC (C18 column, with a mobile phase of 0.1% TFA in CH₃CN/H₂O, gradient from 10% CH₃CN to 90% over 20 min) to give the title compound as a white solid, MS (ESI, pos. ion) m/z: 371 (M+1).

Example 19

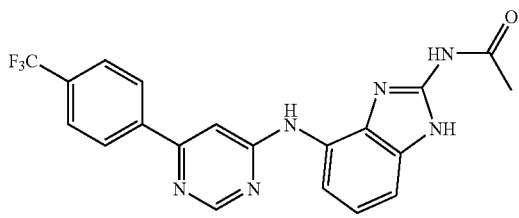

N-{4-[6-(4-Trifluoromethylphenyl)pyrimidin-4-ylamino]-1H-benzoimidazol-2-yl}acetamide. The title compound was isolated from one of the fractions of the preparative HPLC purification of Example 18(d) and was re-purified by preparative HPLC (C8 column, with a mobile phase of 0.1% TFA in CH₃CN/H₂O, gradient from 20% CH₃CN to 80% over 20 min) to yield a white solid. MS (ESI, pos. ion) m/z: 413 (M+1).

Example 20

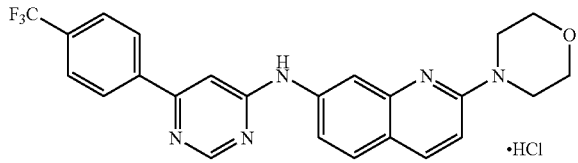

[(2-Morpholin-4-yl)quinolin-7-yl]-[6-(4-trifluoromethylphenyl)pyrimidin-4-yl]amine hydrochloride. A solution of (2-chloroquinolin-7-yl)-[6-(4-trifluoromethylphenyl)pyrimidin-4-yl]amine, Example 13(b), (150 mg, 0.37 mmol) in morpholine (0.65 mL, 7.4 mmol, Aldrich) was stirred and heated in a microwave at 200° C. for 10 min. The resulting bright yellow solid was precipitated from EtOAc and CH₂Cl₂, then dissolved in EtOAc (100 mL) and treated with 1 N HCl (50 mL). The resulting bright yellow precipitate was collected by filtration, washed with water (20 mL), EtOAc (20 mL) and air-dried to provide the title product as a yellow amorphous solid. MS (ESI, pos. ion) m/z: 452 (M+1).

Example 21

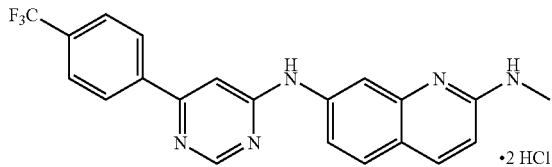

(2-Methylaminoquinolin-7-yl)-[6-(4-trifluoro methylphenyl) pyrimidin-4-yl]amine dihydrochloride. (2-Chloroquinolin-7-yl)-[6-(4-trifluoromethyl-phenyl)pyrimidin-4-yl]amine, Example 13(b), (100 mg, 0.25 mmol) was dissolved in satd methylamine in EtOH [2 mL, prepared by bubbling methylaamine (Aldrich) into EtOH at 0° C.]. The solution was heated in a microwave at 160° C. for 20 min. Additional satd methylamine in EtOH (2 mL) was added and the reaction mixture was heated again in a microwave at 160° C. for 20 min. The mixture was concentrated in vacuo, redissolved in satd methylamine in EtOH (2 mL), and heated for an additional 20 min at 160° C. The mixture was concentrated in vacuo and the residue suspended in 1 N HCl (20 mL) and EtOAc (50 mL). The suspension was shaken vigorously and the solid collected by filtration, washed with water (20 mL), EtOAc (20 mL), hexane (20 mL) and air-dried. The solid was dissolved in MeOH, and concentrated in vacuo to provide the title product as a yellow amorphous solid. MS (ESI, pos. ion) m/z: 396 (M+1).

Example 22

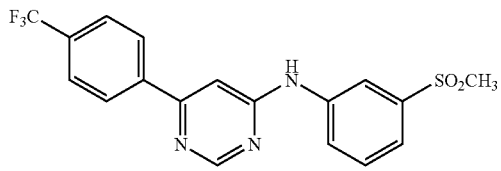

(3-Methanesulfonylphenyl)-[6-(4-trifluoromethylphenyl)pyrimidin-4-yl]amine.

Analogous to the procedure used to prepare Example 5(b), 4-chloro-6-(4-trifluoromethylphenyl)pyrimidine, Example 5(a), (200 mg, 0.77 mmol) and 3-methylsulphonylaniline hydrochloride (80 mg, 0.39 mmol, Acros) afforded a crude reaction product mixture, which was partitioned between EtOAc (100 mL) and 1 N NaOH (50 mL). The organic layer was washed with 1 N NaOH (50 mL), water (50 mL), satd NaCl (20 mL), dried over Na₂SO₄, filtered and concentrated in vacuo. Purification by silica gel chromatography (9:1 CH₂Cl₂/EtOAc) provided the title product as a white solid. MS (ESI, pos. ion) m/z: 394 (M+1). MP: 204-205° C.

Example 23

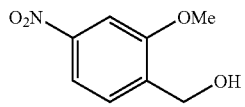

(a) (2-Methoxy-4-nitrophenyl)methan-1-ol. To a solution of 2-methoxy-4-nitrobenzoic acid (2.0 g, 10 mmol, Aldrich) in THF (30 mL), magnetically stirred at 0° C. under N₂ in a round-bottomed flask equipped with a reflux condenser, was added borane-THF complex (30 mL, 30 mmol, 1.0 M in THF, Aldrich). The reaction mixture was stirred at reflux overnight. The reaction was quenched by the careful addition of MeOH (5 mL), followed by 1 N NaOH (30 mL). The mixture was extracted with EtOAc (2×50 mL), the combined organic extracts were washed with satd NaCl, dried over Na₂SO₄, filtered and concentrated in vacuo to give the title product. MS (ESI, neg. ion) m/z: 182 (M−1).

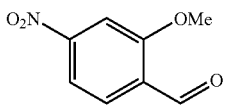

(b) 2-Methoxy-4-nitrobenzaldehyde. A mixture of (2-methoxy-4-nitrophenyl)-methan-1-ol (1.6 g, 8.9 mmol) and $MnO_2$ (15 g, 180 mmol, Aldrich) in 1:1 hexane/$CH_2Cl_2$ (60 mL) was magnetically stirred at 40° C. for 3 h. The solid was removed by filtration and washed with $CH_2Cl_2$. The filtrate was concentrated in vacuo and the residue was recrystallized from EtOAc and hexane to give the title product. MS (ESI, neg. ion) z/z: 180 (M−1).

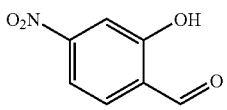

(c) 2-Hydroxy-4-nitrobenzaldehyde. To a solution of 2-methoxy-4-nitrobenzaldehyde, (190 mg, 1.0 mmol) in $CH_2Cl_2$ (5 mL), magnetically stirred at −78° C. in a round-bottomed flask, was added $BBr_3$ (0.19 mL, 2.0 mmol, Aldrich). The reaction mixture was allowed to warm to 25° C. and stirred at that temperature for 2 h. The reaction mixture was then cooled to −78° C., and treated with MeOH (5 mL). The mixture was allowed to warm to 25° C., stirred at that temperature for 30 min, then concentrated in vacuo. Purification by silica gel chromatography (3:2 hexane/EtOAc) provided the title product. MS (ESI, neg. ion) m/z: 166 (M−1).

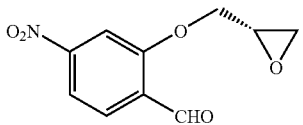

(d) (2S)-4-Nitro-2-oxiranylmethoxybenzaldehyde. A mixture of (2S)-(+)-glycidyl tosylate (1.1 g, 5.0 mmol, Aldrich), 2-hydroxy-4-nitrobenzaldehyde (840 mg, 5.0 mmol) and $K_2CO_3$ (1.4 g, 10 mmol) in DMF (5 mL) in a 100-mL, round-bottomed flask was stirred at 100° C. for 30 min. The mixture was allowed to cool to room temperature, water (20 mL) was added, and the mixture was extracted with EtOAc (3×30 mL). The combined extracts were washed with water (2×20 mL), satd NaCl (10 mL), dried over $Na_2SO_4$, and concentrated in vacuo. The crude material was purified by silica gel chromatography (80% EtOAc in hexane) to give the title product. MS (ESI, pos. ion) m/z: 224 (M+1).

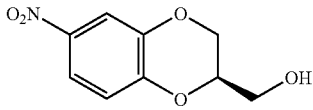

(e) (2R)-(2,3-Dihydro-6-nitrobenzo[1,4]dioxin-2-yl)methanol. (Analogous to the procedure of Andrew, M.; Birch, A. M.; Bradley, P. A. *Synthesis* 1999, 7, 1181-1187). To a solution of (2S)-4-nitro-2-oxiranylmethoxybenzaldehyde (730 mg, 3.3 mmol) in $CH_2Cl_2$ (10 mL) in a 100-mL, round-bottomed flask was added 86% m-chloroperbenzoic acid (1.1 g, 6.4 mmol, Aldrich) at 0° C. The mixture was allowed to warm to room temperature and stirred at that temperature for 18 h. The mixture was diluted with $CH_2Cl_2$ (20 mL), washed with 10% $Na_2S_2O_3$ (6 mL), aq $NaHCO_3$ (3×5 mL), satd NaCl (3 mL), dried over $Na_2SO_4$, and concentrated in vacuo. The crude material was stirred in MeOH (20 mL) and 1 N NaOH (6.5 mL) for 16 h. Water (10 mL) was added, and the mixture was extracted with EtOAc (3×10 mL). The combined organic phases were washed with satd NaCl, dried over $Na_2SO_4$, concentrated in vacuo, and the crude material was purified by silica gel chromatography (40% EtOAc in hexane) to give of the title product. MS (ESI, pos. ion) m/z: 212 (M+1).

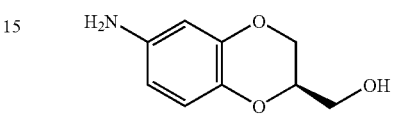

(f) (2R)-(6-Amino-2,3-dihydrobenzo[1,4]dioxin-2-yl)methanol. A mixture of (2R)-(2,3-dihydro-6-nitrobenzo[1,4]dioxin-2-yl)methanol (120 mg, 0.56 mmol) and 10% Pd/C (20 mg, Aldrich) in MeOH (5 mL) in a 100-mL, round-bottomed flask was stirred under 1 atmosphere of $H_2$ for 2 h. The catalyst was filtered off and washed with MeOH. The solvent was removed in vacuo to give the title product. MS (ESI, pos. ion) m/z: 182 (M+1).

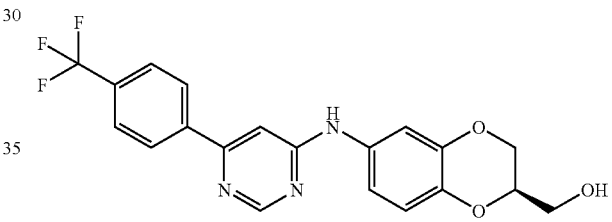

(g) (2R)-{6-[6-(4-Trifluoromethylphenyl)pyrimidin-4-ylamino]-2H,3H-benzo[1,4]dioxin-2-yl}methanol. Analogous to the procedure described for the preparation of Example 5(b), (2R)-(6-amino-2,3-dihydrobenzo[1,4]dioxin-2yl)methanol (100 mg, 0.55 mmol) and 4-chloro-6-(4-trifluoromethylphenyl)-pyrimidine, Example 5(a), (285 mg, 1.1 mmol) provided, after purification by silica gel chromatography (60% EtOAc/hexane), the title product as an amorphous yellow solid. MS (ESI, pos. ion) m/z: 404 (M+1).

Example 24

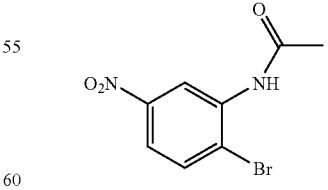

(a) N-(2-Bromo-5-nitrophenyl)acetamide. A solution of 2-bromo-5-nitroaniline (43 g, 0.20 mol, Aldrich) in glacial acetic acid (1.3 L), magnetically stirred at 25° C., was treated with acetic anhydride (20 mL, 0.21 mol). The reaction mixture was allowed to stir at 25° C. overnight, then quenched by pouring into water (6 L). The precipitate was collected by filtration, washed with water, and dried in vacuo to provide the title product as an off-white solid. MS (ESI, pos. ion) m/z: 259, 262 (M+1, M+3).

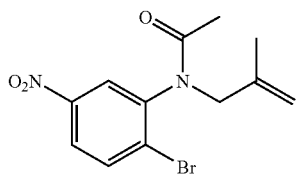

(b) N-(2-Bromo-5-nitrophenyl)-N-(2-methyl-2-propenyl)acetamide. To a flame-dried round-bottomed flask, equipped with magnetic stirring and an addition funnel, was added N-(2-bromo-5-nitrophenyl)acetamide (48 g, 0.19 mol), potassium carbonate (103 g, 744 mmol) and anhydrous DMF (830 mL). The resulting solution was stirred at 25° C. and treated dropwise, through the addition funnel, with a solution of 3-bromo-2-methylpropene (38 mL, 380 mmol, Aldrich) in anhydrous DMF (100 mL) over 45 min. The reaction mixture was stirred at 25° C. overnight, then filtered and treated with satd NaHCO₃. The organic layer was removed and the aqueous layer was extracted with EtOAc (3×150 mL). The combined organic extracts were washed with water (4×70 mL), satd NaCl (70 mL), dried over MgSO₄, filtered and concentrated in vacuo to provide the title product as a yellow solid. MS (ESI, pos. ion) m/z: 313, 315 (M+1, M+3).

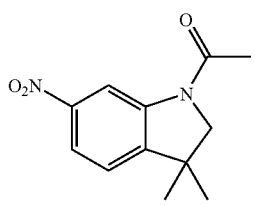

(c) 1-(3,3-Dimethyl-6-nitro-2,3-dihydroindol-yl)ethanone. To a flame-dried, round-bottomed flask, equipped with magnetic stirring, was added N-(2-bromo-5-nitrophenyl)-N-(2-methyl-2-propenyl)acetamide (55 g, 0.18 mol), tetraethylammonium chloride hydrate (30.8 g, 186 mmol, Aldrich), sodium formate (14.4 g, 212 mmol, Aldrich), sodium acetate (36.3 g, 443 mmol) and anhydrous DMF (443 mL). The resulting solution was purged with N₂ and treated with palladium (II) acetate (3.97 g, 17.7 mmol, Aldrich). The reaction mixture was stirred at 80° C. for 15 h, and then allowed to cool to 25° C. and filtered through a pad of Celite®. The Celite® was washed with EtOAc and the combined filtrate was washed with satd NaHCO₃ (500 mL). The aqueous layer was extracted with EtOAc (3×100 mL) and the combined organic extract was washed with water (4×100 mL), satd NaCl (2×100 mL), dried over MgSO₄, filtered and concentrated in vacuo to provide the title product as a brown solid. MS (ESI, pos. ion) m/z: 235 (M+1).

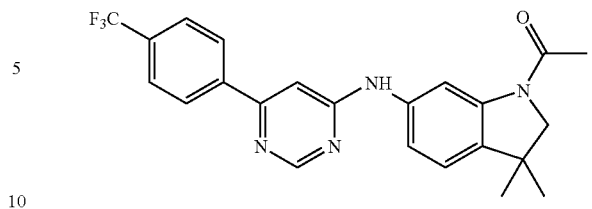

(d) 1-{3,3-Dimethyl-6-[6-(4-trifluoromethylphenyl)pyrimidin-4-ylamino]-2,3-dihydroindol-1-yl}ethanone. To a solution of 1-(3,3-dimethyl-6-nitro-2,3-dihydroindol-yl)ethanone (110 mg, 0.47 mmol) in ethyl ether (3 mL), magnetically stirred in a round-bottomed flask at 0° C., was added tin (II) chloride dihydrate (0.67 g, 2.96 mmol, Aldrich) and concd HCl (0.3 mL). The reaction mixture was stirred at 0° C. for 10 min, allowed to warm to 25° C. then stirred at that temperature overnight. The reaction mixture was washed with 10 N NaOH (10 mL), extracted with EtOAc and concentrated in vacuo. Analogous to the procedure used to prepare Example 5(b), the crude product and 4-chloro-6-(4-trifluoromethylphenyl)pyrimidine, Example 5(a), (0.19 g, 0.75 mmol) provided, after purification by silica gel chromatography (3:2 hexanes/EtOAc), the title product. MS (ESI, pos. ion) m/z: 427 (M+1). MP: 227-230° C.

Example 25

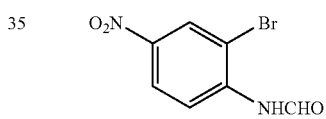

(a) N-(2-Bromo-5-nitrophenyl)formamide. A mixture of 2-bromo-5-nitroaniline (2 g, 9.2 mmol, Aldrich) and 85% formic acid (20 mL, Aldrich) in a 50-mL, round-bottomed flask was heated at reflux for 3 h. The reaction mixture was poured into cold water (75 mL) and the yellow precipitate was filtered, washed with water and dried in a vacuum oven at 60° C. overnight to provide the title compound as a yellow solid. MS (ESI, pos. ion) m/z: 246 (M+1).

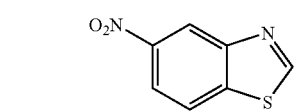

(b) 5-Nitrobenzothiazole. To a solution of N-(2-bromo-5-nitrophenyl)formamide (2.1 g, 8.6 mmol) in hot ethanol (40 mL) was added sodium sulfide (1.1 g, 13 mmol, Aldrich) and the mixture was heated at reflux for 4 h. The solvent was evaporated in vacuo and the residue was diluted with water and filtered. The pH of the filtrate was adjusted to 7 by the addition of 1 N HCl, the precipitate which separated was filtered, washed with water and dried in a vacuum oven at 60° C. overnight to provide the title compound as a yellow solid. MS (ESI, pos. ion) m/z: 181 (M+1).

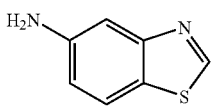

(c) 5-Aminobenzothiazole. To a solution of 5-nitrobenzothiazole (0.55 g, 3.1 mmol) in ethanol (30 mL) was added 10% palladium on carbon (0.18 g, Aldrich). The reaction was stirred under 1 atmosphere of hydrogen for 5 h. The reaction mixture was filtered through a pad of Celite®. The filtrate was concentrated to provide the title compound as an orange solid. MS (ESI, pos. ion) m/z: 151 (M+1).

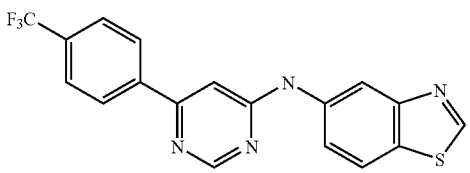

(d) Benzothiazol-5-yl-[6-(4-trifluoromethylphenyl)pyrimidin-4-yl]amine.

Analogous to the procedure used to prepare Example 5(b), 5-aminobenzothiazole (0.16 g, 1.1 mmol) and 4-chloro-6-(4-trifluoromethylphenyl)pyrimidine, Example 5(a), (0.42 g, 1.6 mmol) provided, after purification by silica gel chromatography (2:1 hexanes/EtOAc), the title product as a light-yellow solid. MS (ESI, pos. ion) m/z: 373 (M+1). MP: 192.1-192.2° C.

Example 26

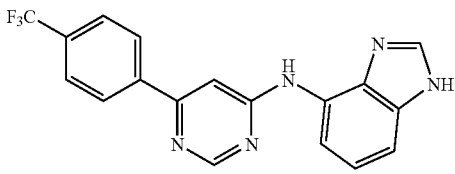

(1H-Benzoimidazol-4-yl)-[6-(4-trifluoromethylphenyl)pyrimidin-4-yl]amine.

Analogous to the procedure used to prepare Example 5(b), 4-chloro-6-(4-trifluoromethylphenyl)pyrimidine, Example 5(a), (690 mg, 2.67 mmol) and 4-aminobenzimidazole (296 mg, 2.22 mmol, Astatech) afforded after purification by silica gel chromatography with gradient from 1% to 10% solution of (2 M $NH_3$ in MeOH) in $CH_2Cl_2$, the title compound as a yellow solid. MS (ESI, pos. ion.) m/z: 356 (M+1).

Example 27

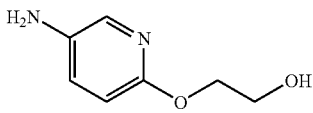

(a) 2-(5-Aminopyridin-2-yloxy)ethanol. To a solution of 2-(5-nitro-2-pyridyloxy)ethanol (1 g, 5.43 mmol, Lancaster) in EtOH (50 mL) was added 10% palladium on carbon (0.2 g, Aldrich) and the mixture was flushed with argon and then stirred under 1 atmosphere of $H_2$ for 15 h. The reaction mixture was filtered through a pad of Celite®, the filtrate was concentrated under vacuo and the residue purified by silica gel column chromatography (EtOAc) to provide the title compound as an off-white solid. MS (ESI, pos. ion.) m/z: 155 (M+1).

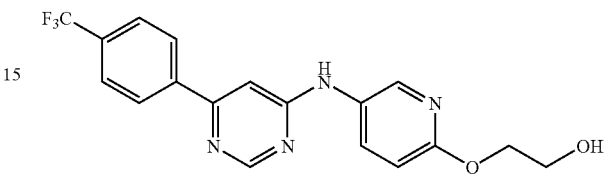

(b) 2-{5-[6-(4-Trifluoromethylphenyl]pyrimidin-4-ylaminolpyridin-2-yloxy}ethanol. 4-Chloro-6-(4-trifluoromethylphenyl)pyrimidine, Example 5(a), (216 mg, 0.83 mmol) was reacted with 2-(5-aminopyridin-2-yloxy)ethanol (130 mg, 0.83 mmol) in EtOH (3 mL) in a fashion similar to that described in Example 5(b), to provide the title compound as a white powder. MS (ESI, pos. ion.) m/z: 377 (M+1). MP: 189.5-190.5° C.

Example 28

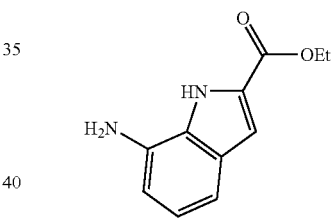

(a) 7-Amino-1H-indole-2-carboxylic acid ethyl ester. To a solution of 7-nitro-1H-indole-2-carboxylic acid ethyl ester (5.0 g, 21.36 mmol, Acros) in MeOH (100 mL) was added 10% palladium on carbon (2.0 g, Aldrich) and the mixture was flushed with argon and then stirred under 1 atmosphere of $H_2$ for 5 h. The reaction mixture was filtered through a pad of Celite® and the filtrate was concentrated to provide the title compound as an off-white solid, which was used in the next step without further purification. MS (ESI, pos. ion.) m/z: 205 (M+1).

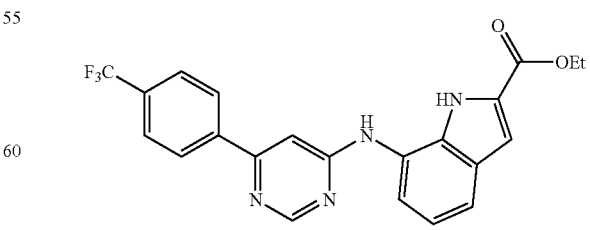

(b) 7-[6-(4-Trifluoromethylphenyl)pyrimidin-4-ylamino]-1H-indole-2-carboxylic acid ethyl ester. 7-Amino-1H-indole-2-carboxylic acid ethyl ester (142 mg, 0.69 mmol) was reacted with 4-chloro-6-(4-trifluoromethylphenyl)-pyrimidine, Example 5(a), (183 mg, 0.71 mmol) in EtOH (3 mL) in a fashion similar to that described in Example 5(b), to provide the title compound as a brown solid. MS (ESI, pos. ion.) m/z: 427 (M+1).

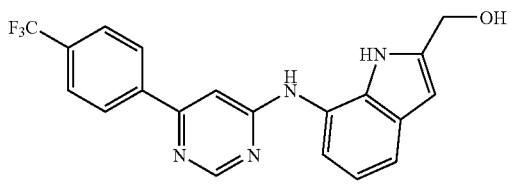

(c) {7-[6-(4-Trifluoromethylphenyl)pyrimidin-4-ylamino]-1H-indol-2-yl}methanol.

To a solution of 7-[6-(4-trifluoromethylphenyl)pyrimidin-4-ylamino]-1H-indole-2-carboxylic acid ethyl ester (285 mg, 0.67 mmol) in THF (2 mL) at 0° C. was added 1 M solution of LiAlH$_4$ in THF (1.0 mL, Aldrich). The mixture was stirred at room temperature and the progress of the reaction was monitored by thin-layer chromatography. After completion of the reaction, to the mixture was added Na$_2$SO$_4$.1H$_2$O (2 g), followed by the addition of MeOH (1 mL) and EtOAc (20 mL) with stirring at 0° C. The stirring was continued for 5 min and the mixture was filtered through a pad of Celite®. The filtrate was concentrated under vacuo and the residue was purified by silica gel column chromatography with gradient from 2% to 10% solution of (2 M NH$_3$ in MeOH) in CH$_2$Cl$_2$ to afford the title compound as a yellow solid. MS (ESI, pos. ion.) m/z: 385 (M+1). MP: 221-223° C.

Example 29

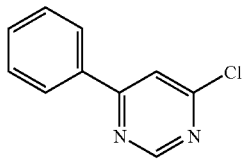

(a) 4-Chloro-6-phenylpyrimidine. To a 500-mL, round-bottomed flask was added 4,6-dichloropyrimidine (6.1 g, 41 mmol, Aldrich), phenylboronic acid (2.0 g, 16 mmol, Aldrich), acetonitrile (150 mL) and 0.40 M aq sodium carbonate (100 mL). The mixture was deoxygenated by sparging with N$_2$ for 15 min. The catalyst, Pd(PPh$_3$)$_4$ (1.9 g, 0.70 mmol, Strem), was added and the yellow mixture was heated at 90° C. for 15 h. The reaction mixture was cooled to room temperature and concentrated in vacuo to remove the acetonitrile. The residue was diluted with water (100 mL) and extracted with ethyl acetate (3×50 mL). The combined organic extracts were dried over Na$_2$SO$_4$, filtered and concentrated in vacuo. Purification by silica gel chromatography (2:1 CH$_2$Cl$_2$/hexane) afforded the title compound as a white solid. MS (ESI, pos. ion) m/z: 191 (M+1).

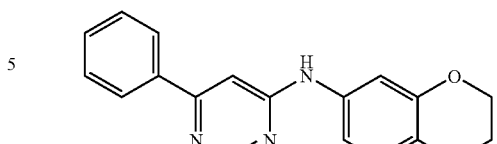

(b) (2,3-Dihydrobenzol[1,4]dioxin-6-yl)-(6-phenylpyrimidin-4-yl)amine.

Analogous to the procedure used to prepare Example 5(b), 4-chloro-6-phenyl)pyrimidine, (0.20 g, 1.0 mmol) and 2,3-dihydrobenzo[1,4]dioxin-6-ylamine (0.20 g, 1.0 mmol, Lancaster) afforded after purification by silica gel chromatography (1:1 ethyl acetate/hexane) afforded the title compound as a purple solid. MS (ESI, pos. ion) m/z: 306 (M+1).

Example 30

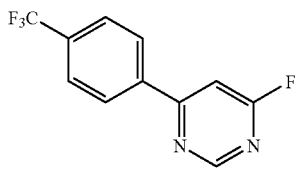

(a) 4-Fluoro-6-[4-(trifluoromethyl)phenyl]pyrimidine

To a 500-mL, round-bottomed flask was added 4-chloro-6-[4-trifluoromethyl)phenyl]pyrimidine, Example 5(a), (3.0 g, 11 mmol), potassium fluoride (5.4 g, 93 mmol, Aldrich) and anhydrous DMSO (25 mL). The reaction mixture was stirred at 100° C. for 4 h under a N$_2$ atmosphere. The mixture was diluted with water (200 mL) and extracted with EtOAc (3×50 mL). The combined extracts were dried over Na$_2$SO$_4$, filtered and concentrated in vacuo. Purification by silica gel chromatography with gradient from 5% to 10% ethyl acetate in hexane afforded the title compound as a white crystalline solid. MS (ESI, pos. ion) m/z: 243 (M+1).

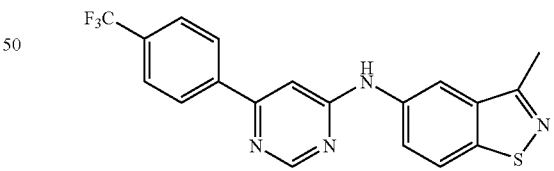

(b) (3-Methylbenzo[d]isothiazol-5-yl)-[6-(4-trifluoromethylphenyl)pyrimidin-4-yl]amine. To a glass vial containing a magnetic stir bar was added 4-fluoro-6-[4-(trifluoromethyl)phenyl]pyrimidine (0.10 g, 0.39 mmol), 5-aminobenzotriazole (0.10 g, 0.42 mmol, Lancaster) and DMSO (1 mL). The reaction mixture was stirred and heated in a microwave at 180° C. for 20 min. The mixture was diluted with water (100 mL) and extracted with EtOAc (2×10 mL). The combined extracts were dried over Na$_2$SO$_4$, filtered and concentrated in vacuo. Purification by silica gel chromatography (1:1 ethyl acetate/hexane) afforded the title compound as a yellow solid. MS (ESI, pos. ion) m/z: 387 (M+1).

Example 31

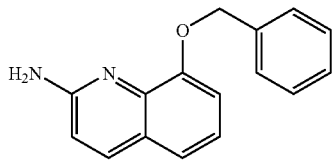

(a) 8-Benzyloxyquinolin-2-ylamine. To a 25-mL, round-bottomed flask under a N₂ atmosphere was added 2-aminoquinolin-8-ol (0.20 g, 1.3 mmol, Sigma) and DMF (8 mL). The mixture was cooled to 0° C. and NaH (0.06 g, 1.5 mmol, Aldrich, 60% dispersion in oil) was added. After stirring for 10 min at 0° C., benzyl bromide (0.16 mL, 1.4 mmol, Aldrich) was added and the mixture was allowed to warm to room temperature. After stirring for 23 h, the reaction was quenched with H₂O and extracted with EtOAc. The combined extracts were washed with 1 N NaOH (2×), H₂O and brine, dried over Na₂SO₄ and concentrated in vacuo to afford the title compound as an off-white solid. MS (ESI, pos. ion) m/z: 251 (M+1).

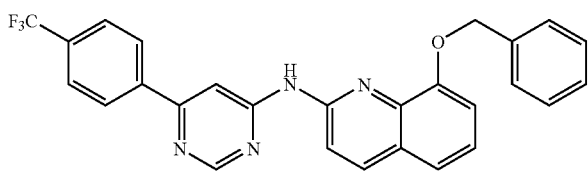

(b) (8-Benzyloxyquinolin-2-yl)-[6-(4-trifluoromethylphenyl)pyrimidin-4-yl]amine.

To an oven dried, 15-mL round-bottomed flask was added Pd(OAc)₂ (4 mg, 0.02 mmol, Aldrich) and rac-2,2'-bis(diphenylphosphino)-1,1'-binaphthyl (12 mg, 0.020 mmol, Aldrich). The flask was carefully evacuated and then backfilled with N₂, twice. Toluene (4 mL) was added and the mixture was stirred for 5 min at room temperature. To the mixture were then added 4-chloro-6-(4-trifluoro-methylphenyl)pyrimidine, Example 5(a), (100 mg, 0.40 mmol), 8-benzyloxyquinolin-2-ylamine (100 mg, 0.40 mmol) and K₂CO₃ (1.1 g, 8.0 mmol). The reaction vessel was again carefully evacuated and backfilled with N₂, twice. The reaction was stirred for 16 h at 90° C. After cooling to room temperature, the reaction mixture was diluted with CH₂Cl₂/MeOH (3:1) and filtered. The filtrate was concentrated in vacuo onto silica gel and purified by silica gel chromatography with gradient from 0.3% to 1.5% solution of (2 M NH₃ in MeOH) in CH₂Cl₂. The title compound was isolated as an off-white solid. MS (ESI, pos. ion) m/z: 473 (M+1).

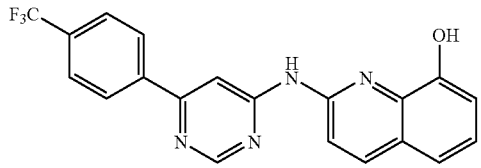

(c) 2-[6-(4-Trifluoromethylphenyl)pyrimidin-4-ylamino]quinolin-8-ol. To a round-bottomed flask containing (8-benzyloxyquinolin-2-yl)-[6-(4-trifluoro-methylphenyl)pyrimidin-4-yl]amine (0.050 g, 0.11 mmol) in MeOH (5 mL) and AcOH (0.5 mL) was added palladium [10 wt. % (dry basis) on activated carbon, wet, Degussa type E101 NE/W, 0.022 g, Aldrich). The flask was carefully evacuated and backfilled with H₂, twice. The reaction mixture was stirred under 1 atmosphere H₂ for 24 h. The flask was then evacuated and backfilled with N₂, twice. The suspension was diluted with MeOH and filtered. The filtercake was washed with MeOH and MeOH/CH₂Cl₂ and the combined filtrates were concentrated in vacuo. The crude product was purified by preparative HPLC. The fractions containing product were combined, concentrated in vacuo to remove the CH₃CN, neutralized with pH 7 buffer (Gibco BRL 20×SSC, 3.0 M NaCl and 0.3 M sodium citrate). The resulting precipitate was collected by filtration and dried in vacuo to afford the title compound as a yellow solid. MS (ESI, pos. ion) m/z: 383 (M+1).

Example 32

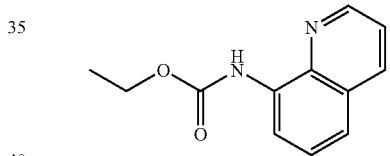

(a) Quinolin-8-ylcarbamic acid ethyl ester. To a solution of 8-aminoquinoline (2.5 g, 17 mmol, Aldrich) in pyridine (50 mL) was added ethyl chloroformate (2.0 mL, 20 mmol, Aldrich). The mixture was cooled to 0° C. and stirred for 30 min, then allowed to warm to room temperature and stirred at that temperature for 3 days. The mixture was concentrated in vacuo and diluted with satd NaHCO₃ and H₂O (1:1). The mixture was extracted with EtOAc (3×100 mL) and the combined extracts were washed with H₂O (100 mL), brine (100 mL), dried over Na₂SO₄ and concentrated in vacuo to provide the title compound as a brown solid. MS (ESI, pos. ion) m/z: 217 (M+1).

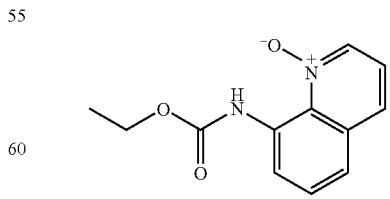

(b) (1-Oxyquinolin-8-yl)carbamic acid ethyl ester. To a 100-mL, round-bottomed flask was added quinolin-8-ylcarbamic acid ethyl ester (3.6 g, 17 mmol), AcOH (14 mL) and 30% aq H₂O₂ (4.0 mL, Aldrich). The reaction mixture was stirred at 65° C. for 3 h. Additional H₂O₂ (2.0 mL) was added and stirring was continued at 65° C. for 17 h. The reaction mixture was cooled to room temperature and diluted with H₂O (150 mL) and satd NaHCO₃ (150 mL). Once the gas evolution had nearly subsided, the mixture was extracted with EtOAc (3×100 mL). The combined extracts were washed with aq NaHCO₃, brine, dried over Na₂SO₄, filtered and the filtrate concentrated in vacuo. The crude product was eluted with EtOAc through a plug of silica gel and concentrated in vacuo to afford the title compound as an orange solid. MS (ESI, pos. ion) m/z: 233 (M+1).

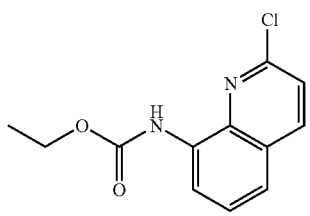

(c) (2-Chloroquinolin-8-yl)carbamic acid ethyl ester. To a round-bottomed flask containing (1-oxy-quinolin-8-yl)carbamic acid ethyl ester (2.7 g, 12 mmol) in toluene (50 mL) was added SOCl₂ (1 mL, 14 mmol, Aldrich). The reaction mixture was stirred at 75° C. for 5 h, then allowed to cool to room temperature and concentrated in vacuo. The residue was diluted with satd NaHCO₃ (50 mL) and H₂O (50 mL) and extracted with EtOAc (2×100 mL). The combined extracts were washed with H₂O (100 mL), brine (100 mL), dried over Na₂SO₄ and concentrated in vacuo onto silica gel. Purification by silica gel chromatography with gradient from 0% to 10% EtOAc in hexane, followed by recrystallization from hexane afforded the title compound as a white solid. MS (ESI, pos. ion) m/z: 251 (M+1).

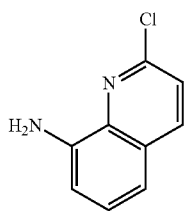

(d) 2-Chloroquinolin-8-ylamine. To a round-bottomed flask containing (2-chloroquinolin-8-yl)carbamic acid ethyl ester (0.28 g, 1.1 mmol) in 2-methyl-2-propanol (25 mL) was added 10 N NaOH (15 mL). The mixture was stirred at 70° C. for 2 days. The mixture was cooled to room temperature and then diluted with satd NaHCO₃ and extracted with EtOAc. The aqueous phase was neutralized with conc. HCl and extracted with EtOAc. The combined extracts were washed with H₂O (2×), brine, dried over Na₂SO₄ and concentrated in vacuo onto silica gel. Purification by silica gel chromatography with gradient from 0% to 10% EtOAc in hexane afforded the title compound as a pale yellow solid. MS (ESI, pos. ion) m/z: 179 (M+1).

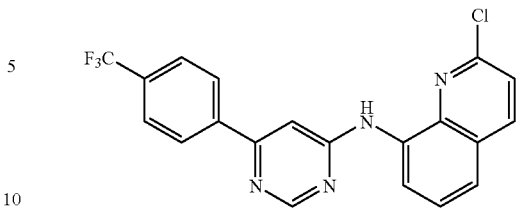

(e) (2-Chloroquinolin-8-yl)-[6-(4-trifluoromethylphenyl)pyrimidin-4-yl]amine. To a glass vial containing a magnetic stir bar was added 4-fluoro-6-(4-trifluoromethylphenyl)pyrimidine, Example 29(a), (0.39 g, 1.6 mmol), 2-chloro-quinolin-8-ylamine (0.14 g, 0.79 mmol) and anhydrous DMSO (1 mL). The reaction mixture was stirred and heated in a microwave at 170° C. for 20 min. The mixture was diluted with satd NaHCO₃ and extracted with EtOAc. The combined extracts were washed with H₂O, brine, dried over Na₂SO₄, filtered and concentrated in vacuo onto silica gel. Purification by silica gel chromatography with gradient from 3% to 18% EtOAc in hexane afforded the title compound as a white solid. MS (ESI, pos. ion) m/z: 401 (M+1). MP: 240° C.

Example 33

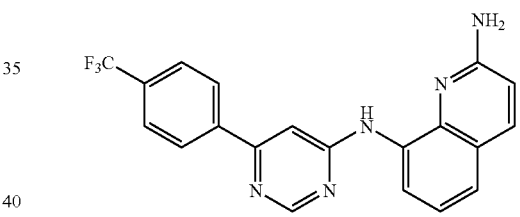

N⁸-[6-(4-Trifluoromethylphenyl)pyrimidin-4-yl]quinoline-2,8-diamine. To a round-bottomed flask containing (2-chloroquinolin-8-yl)-[6-(4-trifluoromethyl-phenyl)pyrimidin-4-yl]amine, Example 32(e), (0.090 g, 0.22 mmol) in DMSO (10 mL) was added NaN₃ (0.53 g, 8.1 mmol, Aldrich). The reaction mixture was stirred at 105° C. for 4 days and then at 115° C. for 1 day. The reaction mixture was cooled to room temperature and then diluted with H₂O and extracted with EtOAc. The combined extracts were washed with H₂O (3×), brine, dried over Na₂SO₄, and concentrated in vacuo to afford a tan solid. The tan solid was dissolved in toluene (5 mL), triphenylphosphine (0.12 g, 0.44 mmol, Aldrich) was added with stirring at room temperature and the mixture was stirred at reflux for 8 h. After cooling to room temperature, the mixture was concentrated in vacuo to remove the toluene. To the residue was added AcOH/H₂O (2:1, 7 mL) and the mixture was stirred at 55° C. for 1 day. The reaction mixture was cooled to room temperature and then diluted with satd NaHCO₃ (75 mL) and extracted with EtOAc (2×75 mL). The combined extracts were washed with brine, dried over K₂CO₃ and concentrated in vacuo. The residue was dissolved in EtOAc and concentrated in vacuo onto silica gel. Purification by silica gel chromatography with gradient from 20% to 60%

Example 34

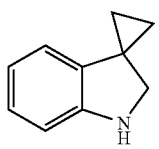

(a) Spiro[cyclopropane-1,3'-indoline]. To a solution of 3-(2-bromoethyl)indole (5 g, 22.31 mmol, Aldrich) in anhydrous $CH_3CN$ (100 mL) was added oven dried $K_2CO_3$ (20 g, 144.7 mmol)) and the mixture was heated under reflux with stirring for 10 h. The mixture was cooled to room temperature, filtered and the filter cake was washed with EtOH (50 mL). The combined filtrate was then treated with NaBH4 (300 mg, 7.93 mmol)) and stirred for 3 h at room temperature. The solvents were removed in vacuo and the residue was partitioned between water (160 mL) and EtOAc (60 mL). The organic layer was extracted with 0.5N aq HCl (30 mL×2). The acid layer was then basified with 28% aq $NH_4OH$ and then extracted with EtOAc. The combined organic extracts were washed with brine, dried over $Na_2SO_4$ and concentrated to give the title compound as a colorless oil. MS (ESI, pos. ion) m/z: 146 (M+1).

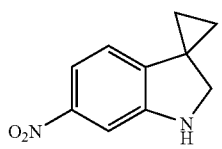

(b) 6'-Nitrospiro[cyclopropane-1,3'-indoline]. Spiro[cyclopropane-1,3'-indoline] (1.8 g, 12.4 mmol) was added dropwise over 20 min into a solution of $NaNO_3$ (1.3 g, 15.3 mmol) in concd $H_2SO_4$ (30 mL) with stirring and cooling (−5 to −10° C.). The reaction mixture was stirred with cooling for another 40 min and poured onto crushed ice (200 g). The resulting mixture was basified with 28% aq $NH_4OH$ with cooling and extracted with EtOAc. The combined organic extracts were washed with brine, dried over $Na_2SO_4$ and concentrated in vacuo to give the desired product as a dark gray solid. MS (ESI, pos. ion) m/z: 191 (M+1).

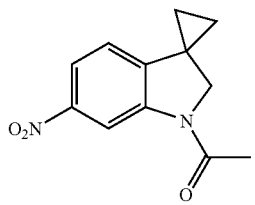

(c) 1'-Acetyl-6'-nitrospirolcyclopropane-1,3'-indoline]. Acetyl chloride (1.1 g, 14 mmol) was added dropwise to a suspension of $NaHCO_3$ (5 g, 59.5 mmol) in a solution of 6'-nitrospiro[cyclopropane-1,3'-indoline] (2.6 g, 13.7 mmol) in dichloromethane (200 mL) with vigorous stirring at room temperature. The reaction mixture was stirred for 2 h at room temperature and filtered. The filtrate was concentrated in vacuo and the residue purified by flash chromatography on silica gel with gradient from 75% to 80% solution of EtOAc in hexane to give the title compound. MS (ESI, pos. ion) m/z: 233 (M+1).

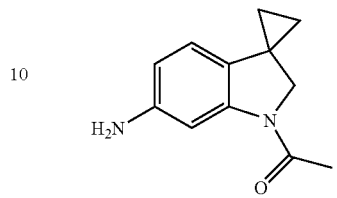

(d) {1'-Acetylspiro[cyclopropane-1,3'-indolin-6'-yl]}amine. To a solution of 1'-acetyl-6'-nitrospiro[cyclopropane-1,3'-indoline] (2 g, 8.61 mmol) in EtOH (200 mL) was added 10% palladium on carbon (0.1 g, Aldrich) and the mixture was flushed with argon and then stirred under 1 atmosphere of $H_2$ for 1.5 h. The reaction mixture was filtered through a pad of Celite® and the filtrate was concentrated to provide the title compound as white solid. MS (ESI, pos. ion) m/z: 203 (M+1).

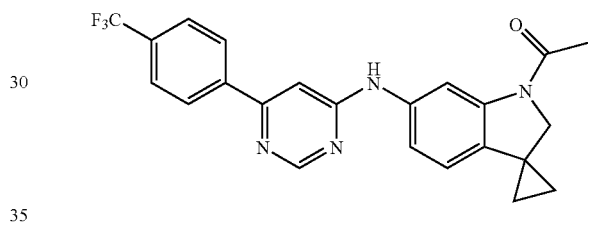

(e) {1'-Acetylspiro[cyclopropane-1,3'-indolin-6'-yl]}-[6-(4-trifluoromethyl-phenyl)pyrimidin-4-yl]amine. A mixture of 4-chloro-6-(4-trifluoromethyl-phenyl)pyrimidine, Example 5(a), (0.138 g, 0.53 mmol) and {1'-acetylspiro-[cyclopropane-1,3'-indolin-6'-yl]}amine (0.119 g, 0.58 mmol) in DMSO (1 mL) was stirred and heated in a microwave at 180° C. for 10 min. The mixture was diluted with water and extracted with $CH_2Cl_2$. The combined extracts were dried over $Na_2SO_4$, filtered and concentrated in vacuo. Purification of the residue by silica gel chromatography with gradient from 0% to 40% solution of MeOH in $CH_2Cl_2$ afforded the title compound as a yellow amorphous solid. MS (ESI, pos. ion) m/z: 425 (M+1).

Example 35

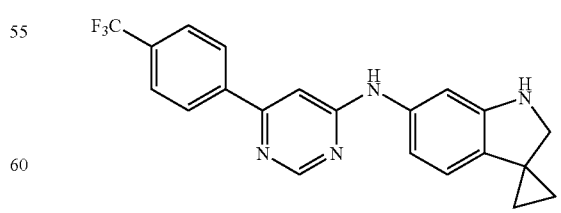

{Spiro[cyclopropane-1,3'-indolin-6'-yl]}-[6-(4-trifluoromethylphenyl)-pyrimidin-4-yl] amine. A mixture of {1'-acetylspiro[cyclopropane-1,3'-indolin-6'-yl]}-[6-(4-trifluoromethylphenyl)pyrimidin-4-yl]amine, Example 34(e), (0.043 g, 0.10 mmol), 5 N of HCl (aq) (3.0 mL) and THF (1.0 mL) was stirred and heated at reflux for 3 h. The mixture was cooled to room temperature, basified with 10 N aq NaOH to pH~10 and extracted with $CH_2Cl_2$. The combined extracts were washed with water, dried over $Na_2SO_4$, filtered and concentrated in vacuo to give the title compound as a yellow amorphous solid. MS (ESI, pos. ion) m/z: 383 (M+1).

Example 36

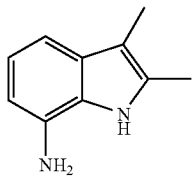

(a) 2,3-Dimethyl-1H-indol-7-ylamine. A solution of 2,3-dimethyl-7-nitroindole (500 mg, 2.6 mmol, Acros) in MeOH (25 mL) was placed under $N_2$ and treated with 10% palladium on carbon (281 mg, Aldrich). The suspension was purged with $N_2$ and magnetically stirred under 1 atmosphere $H_2$ for 16 h. The reaction mixture was filtered through a pad of Celite® and the filtrate was concentrated to provide the title compound as a brown amorphous solid. MS (ESI, pos. ion) m/z: 161 (M+1).

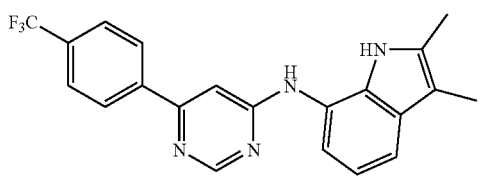

(b) (2,3-Dimethyl-1H-indol-7-yl)-[6-(4-(trifluoromethylphenyl)pyrimidin-4-yl]amine.

Analogous to the procedure used to prepare Example 5(b), 4-chloro-6-(4-trifluoromethylphenyl)pyrimidine, Example 5(a), (240 mg, 93 mmol) and 2,3-dimethyl-1H-indol-7-ylamine (150 mg, 0.93 mmol) provided after purification by preparative HPLC, the title compound as a brown amorphous solid. MS (ESI, pos. ion) m/z: 383 (M+1).

Example 37

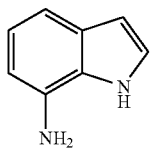

(a) 1H-Indol-7-ylamine. The title compound was prepared by the method described in Example 36(a) from 7-nitroindole (500 mg, 2.6 mmol, Lancaster) to give a green amorphous solid. MS (ESI, pos. ion) m/z: 133 (M+1).

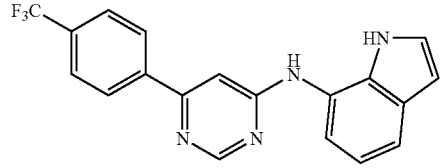

(b) (1H-Indol-7-yl)-[6-(4-trifluoromethylphenyl)pyrimidin-4-yl)amine.

Analogous to the procedure used to prepare Example 5(b), 4-chloro-6-(4-trifluoromethylphenyl)pyrimidine, Example 5(a), (0.588 g, 2.28 mmol) and 1H-indol-7-ylamine (150 mg, 1.13 mmol) provided the title compound as a brown amorphous solid. MS (ESI, pos. ion) m/z: 355 (M+1).

Example 38

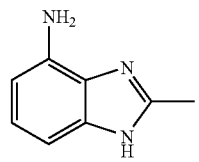

(a) 2-Methyl-1H-benzoimidazol-4-ylamine. The title compound was prepared by the method described in Example 36(a) from 7-nitro-2-methylbenzimidazole (0.3 g, 1.6 mmol, Tyger Sci.) to give a brown amorphous solid. MS (ESI, pos. ion) m/z: 148 (M+1).

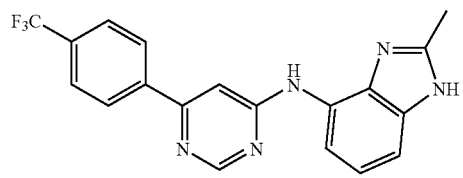

(b) (2-Methyl-1H-benzoimidazol-4-yl)-[6-(4-trifluoromethyl)phenyl)pyrimidin-4-yl]amine. Analogous to the procedure used to prepare Example 5(b), 4-chloro-6-(4-trifluoromethylphenyl)pyrimidine, Example 5(a), (227 mg, 0.88 mmol) and 7-amino-2-methylbenzimidazole (150 mg, 0.88 mmol) provided the title compound as a light-yellow crystalline solid. MS (ESI, pos. ion) m/z: 370 (M+1).

Example 39

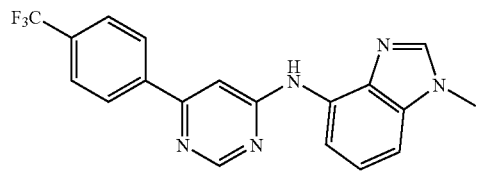

(1-Methyl-1H-benzoimidazol-4-yl)-[6-(4-trifluoromethyl)phenyl)pyrimidin-4-yl]amine. Analogous to the procedure used to prepare Example 5(b), 4-chloro-6-(4-trifluoromethylphenyl)pyrimidine, Example 5(a), (227 mg 0.88 mmol) and 7-amino-1-methyl-N-benzimidazole (350 mg, 0.88 mmol, Aldrich) provided, after purification by silica gel column chromatography with eluent 10% solution of (2M NH$_3$ in MeOH) in CH$_2$Cl$_2$, the title compound as a light-yellow amorphous solid. MS (ESI, pos. ion) m/z: 371.2 (M+1).

Example 40

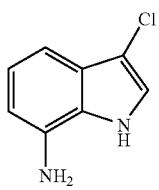

(a) 3-Chloro-1H-indol-7-ylamine. Analogous to the procedure used to prepare Example 16(b), 3-chloro-7-nitroindole (0.15 g, 0.76 mmol, UbiChem Res.) was reduced with iron dust (0.635 g, 11.3 mmol, Aldrich) to give the title compound as a yellow amorphous solid. MS (ESI, pos. ion) m/z: 167 (M+1).

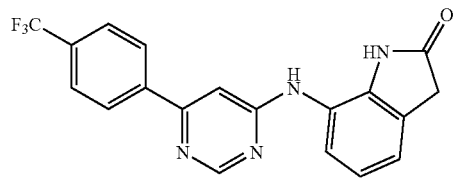

(b) 7-[6-(4-Trifluoromethylphenyl]pyrimidin-4-ylamino]-1,3-dihydroindol-2-one. Analogous to the procedure used to prepare Example 5(b), 4-chloro-6-(4-trifluoromethylphenyl) pyrimidine, Example 5(a), (172 mg, 0.66 mmol) and 3-chloro-1H-indol-7-ylamine (110 mg, 0.66 mmol) afforded the title compound as a brown amorphous solid. MS (ESI, pos. ion) m/z: 371 (M+1).

ADDITIONAL EXAMPLES

Following the procedures described above in Scheme 1, or with slight modifications thereof, and following procedures familiar to one of ordinary skill in the art, the following examples were prepared from commercially available reagents:

| Example | Structure | MS (ESI, pos. ion) m/z | Melting Point ° C. |
|---|---|---|---|
| 41 | 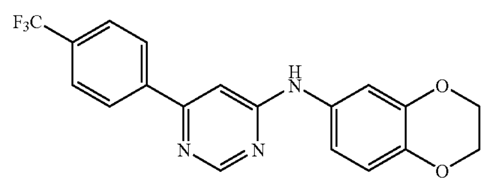 | 374 (M + 1) | 167-168 |
| 42 | 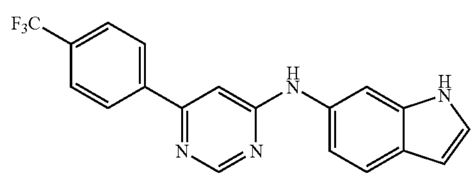 | 355 (M + 1) | 231-232 |
| 43 | 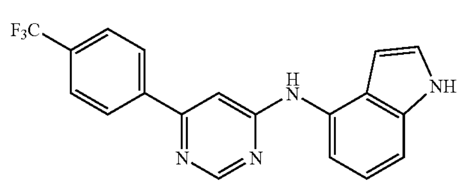 | 355 (M + 1) | 222-224 |
| 44 | 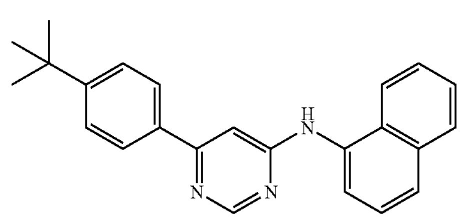 | 355 (M + 1) | 183-185 |

-continued
| Example | Structure | MS (ESI, pos. ion) m/z | Melting Point ° C. |
|---|---|---|---|
| 45 | 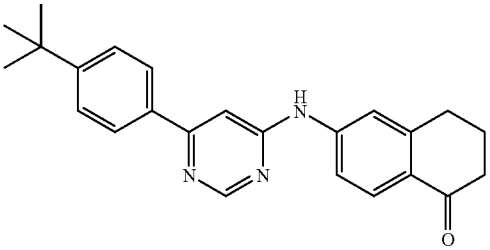 | 372 (M + 1) | 230-232 |
| 46 | 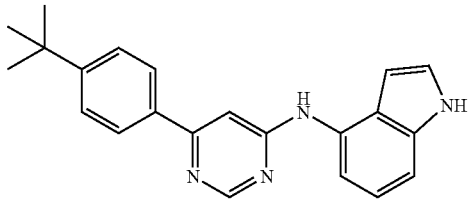 | 343 (M + 1) | 241-242 |
| 47 | 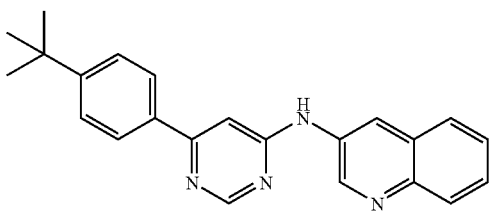 | 355 (M + 1) | 227-229 |
| 48 | 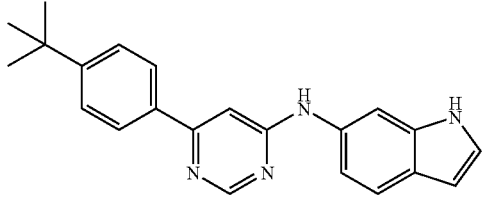 | 343 (M + 1) | 194-196 |
| 49 | 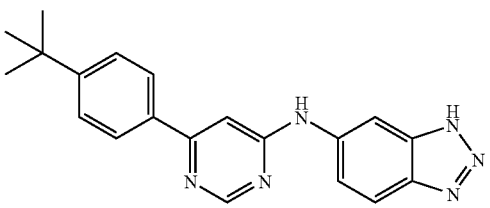 | 345 (M + 1) | 250-252 |
| 50 | 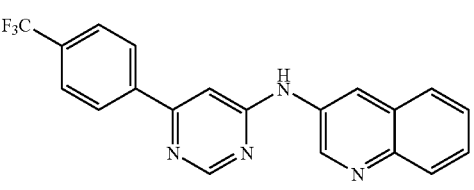 | 367 (M + 1) | 262-263 |
| 51 | 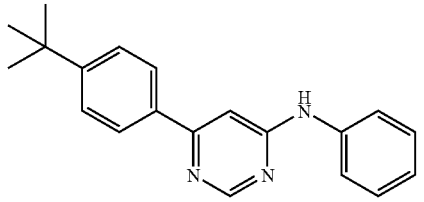 | 304 (M + 1) | 166 |

-continued

| Example | Structure | MS (ESI, pos. ion) m/z | Melting Point ° C. |
|---------|-----------|------------------------|--------------------|
| 52 | 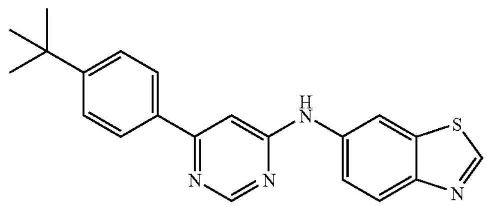 | 361 (M + 1) | 237 |
| 53 | 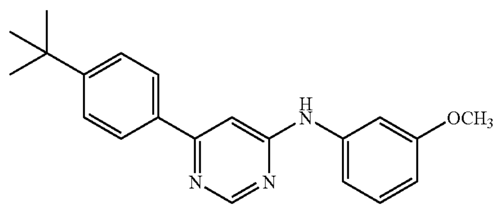 | 334 (M + 1) | 184-187 |
| 54 | 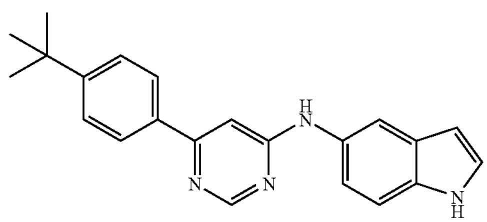 | 343 (M + 1) | 238-240 |
| 55 | 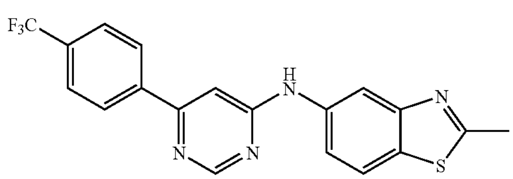 | 387 (M + 1) | 219.5-220.5 |
| 56 | 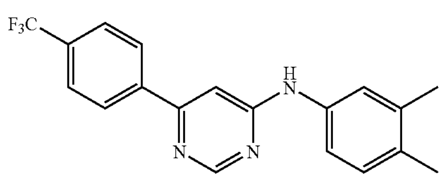 | 344 (M + 1) | 154-156 |
| 57 | 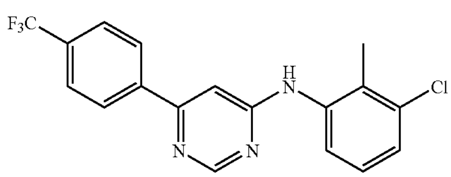 | 364 (M + 1) | 148-150 |
| 58 | 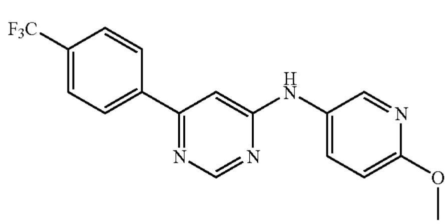 | 347 (M + 1) | 123-127 |

-continued

| Example | Structure | MS (ESI, pos. ion) m/z | Melting Point ° C. |
|---------|-----------|------------------------|--------------------|
| 59 | F₃C-phenyl-pyrimidine-NH-phenyl-SMe (3-position) | 362 (M + 1) | 130-132 |
| 60 | F₃C-phenyl-pyrimidine-NH-(4-methylphenyl) | 330 (M + 1) | 159-160 |
| 61 | F₃C-phenyl-pyrimidine-NH-(4-Cl-3-CF₃-phenyl) | 418 (M + 1) | 172-175 |
| 62 | F₃C-phenyl-pyrimidine-NH-(4-Cl-phenyl) | 350 (M + 1) | 193-196 |
| 63 | F₃C-phenyl-pyrimidine-NH-(3,4-diCl-phenyl) | 384 (M + 1) | 178-180 |
| 64 | F₃C-phenyl-pyrimidine-NH-(2-methylphenyl) | 330 (M + 1) | 117-119 |
| 65 | F₃C-phenyl-pyrimidine-NH-(2-methyl-5-Cl-phenyl) | 364 (M + 1) | 144-146 |

-continued

| Example | Structure | MS (ESI, pos. ion) m/z | Melting Point ° C. |
|---|---|---|---|
| 66 | 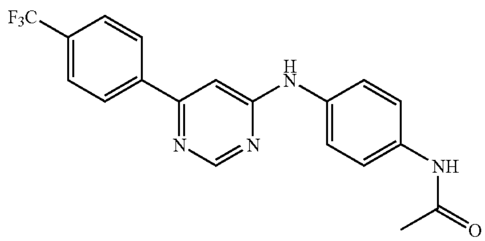 | 373 (M + 1) | 236-238 |
| 67 | 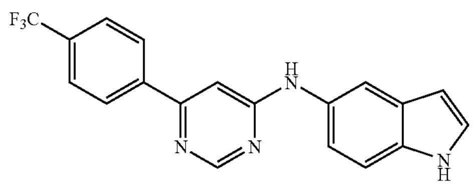 | 355 (M + 1) | amorphous |
| 68 | 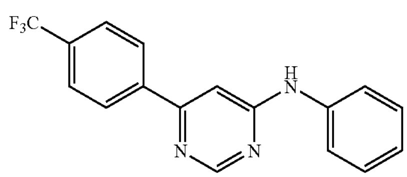 | 316 (M + 1) | 184-186 |
| 69 | 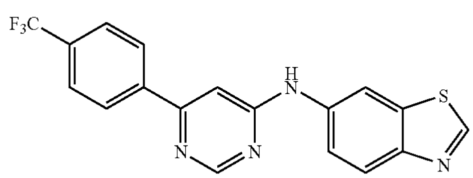 | 373 (M + 1) | amorphous |
| 70 | 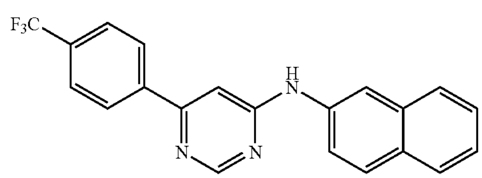 | 366 | 212-213 |
| 71 | 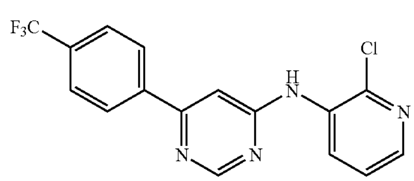 | 351 | 134-135 |
| 72 | 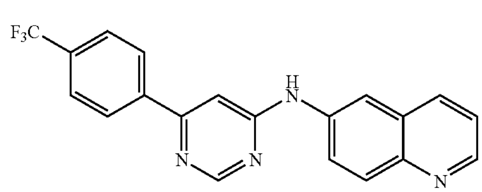 | 367 | 268-269 |
| 73 | 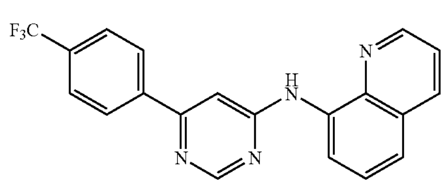 | 367 | 162-163 |

-continued
| Example | Structure | MS (ESI, pos. ion) m/z | Melting Point ° C. |
|---|---|---|---|
| 74 | 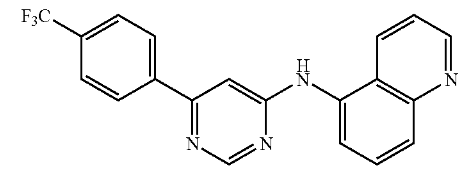 | 367 | 238-239 |
| 75 | 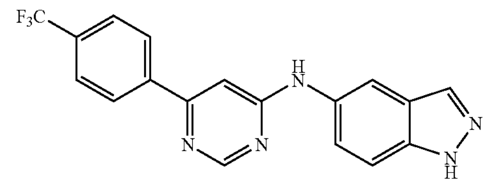 | 356 | 224-226 |
| 76 | 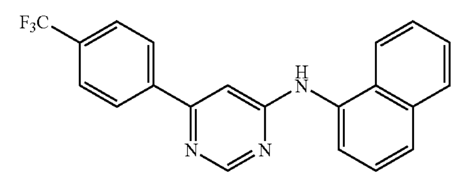 | 366 | 232-233 |
| 77 | 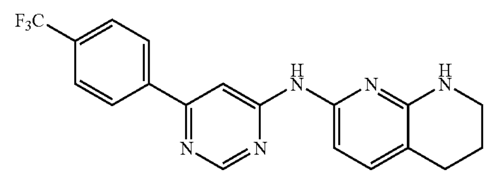 | 372 | 168 |
Scheme II: Generic Schemes for the preparation of pyridazine core:
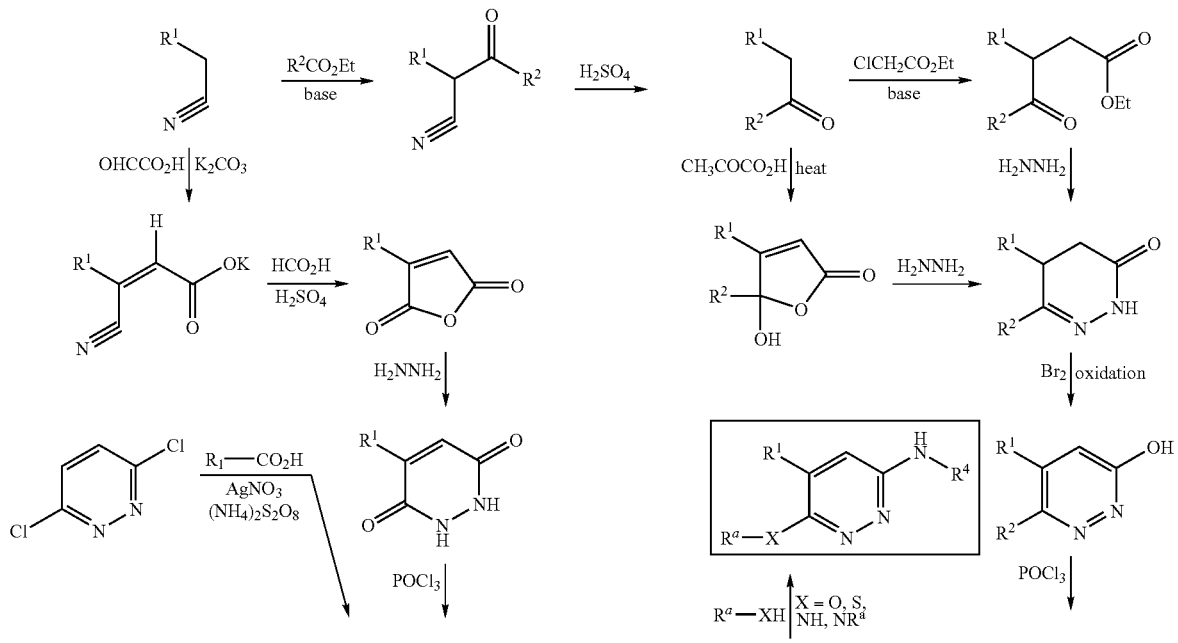

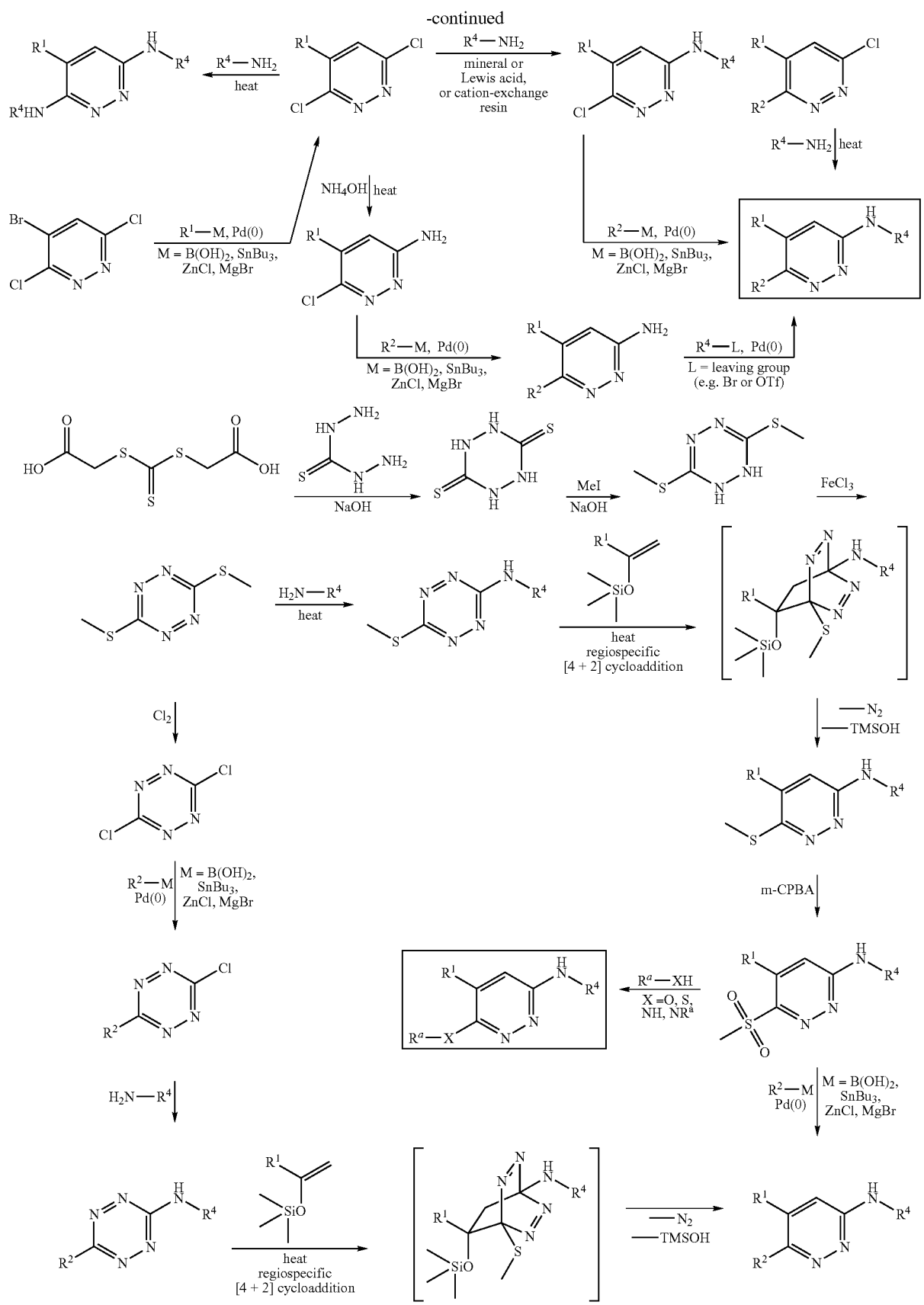

Example 78

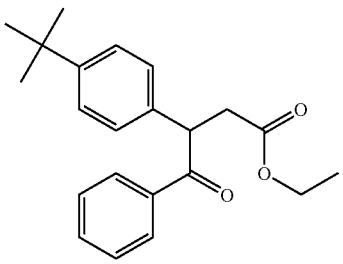

(a) 3-(4-tert-Butylphenyl)-4-oxo-4-phenylbutyric acid ethyl ester. (Analogous to the procedure of EP 0 469 992 B 1). In a round-bottomed flask was placed 60% dispersion of NaH in mineral oil (264 mg, 6.6 mmol, Aldrich) and the oil was washed with hexane (2×). To this flask was added a solution of 2-(4-tert-butylphenyl)-1-phenylethanone (1.5 g, 5.9 mmol, J. Am. Chem. Soc. 1997, 119, 12382) in DMSO (30 mL) with stirring at 0° C. The mixture was stirred at room temperature for 1 h, ethyl chloroacetate (0.6 mL, 0.7 g, 6.0 mmol, Aldrich) was then added and the stirring was continued for 18 h. The reaction mixture was quenched with 1M aq $H_3PO_4$, diluted with EtOAc (50 mL), washed with satd aq $NaHCO_3$ and brine, dried over $Na_2SO_4$, filtered and concentrated to give the title compound. MS (ESI, pos. ion) m/z: 339 (M+1).

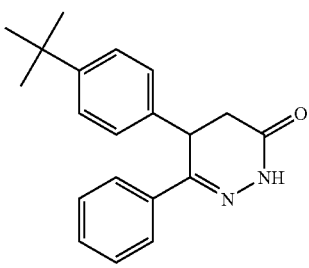

(b) 5-(4-tert-Butylphenyl)-6-phenyl-4,5-dihydro-2H-pyridazin-3-one. To a solution of 3-(4-tert-butylphenyl)-4-oxo-4-phenylbutyric acid ethyl ester (1.81 g, 5.4 mmol) in dioxane (5 mL) was added hydrazine hydrate (0.346 g, 10.8 mmol, Aldrich) and the mixture was heated under reflux with stirring overnight. The reaction mixture was cooled to room temperature, diluted with EtOAc (50 mL) and washed with 0.5% aq $H_3PO_4$, satd $NaHCO_3$ and brine, dried over $Na_2SO_4$, filtered and concentrated to give the title compound as a yellow solid. MS (ESI, pos. ion) m/z: 307 (M+1).

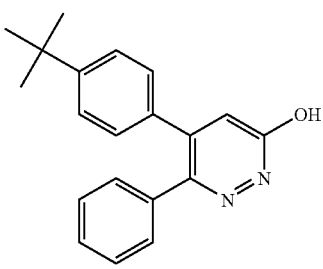

(c) 5-(4-tert-Butylphenyl)-6-phenylpyridazin-3-ol. 5-(4-tert-Butylphenyl)-6-phenyl-4,5-dihydro-2H-pyridazin-3-one (1.15 g, 3.8 mmol) was dissolved in glacial AcOH (5 mL) and heated to 60° C. Bromine (722 mg, 4.5 mmol) was added dropwise and the mixture was heated at 60° C. with stirring for 10 min. The reaction mixture was cooled to room temperature, diluted with EtOAc (50 mL) and washed with satd aq $NaHCO_3$ (3×). The organic layer was dried over $Na_2SO_4$, filtered and concentrated to give the title compound, which was used in the next step without additional purification. MS (ESI, pos. ion) m/z: 305 (M+1).

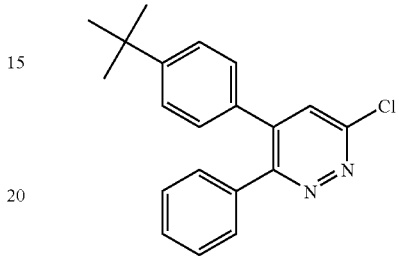

(d) 4-(4-tert-Butylphenyl)-6-chloro-3-phenylpyridazine. 5-(4-tert-Butylphenyl)-6-phenylpyridazin-3-ol (549 mg, 1.8 mmol) was dissolved in $POCl_3$ (3 mL) and heated at 100° C. with stirring overnight. The $POCl_3$ was removed in vacuo and the residue was dissolved in EtOAc and washed with satd aq $NaHCO_3$ (2×). The organic layers were combined, dried over $Na_2SO_4$, filtered and the solvent was evaporated in vacuo to give the title compound. MS (ESI, pos. ion) m/z: 323 (M+1).

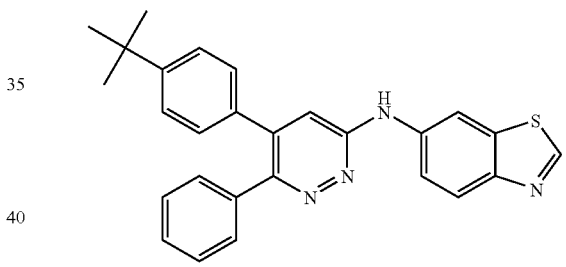

(e) Benzothiazol-6-yl-[5-(4-tert-butylphenyl)-6-phenylpyridazin-3-yl]amine.

Analogous to the procedure used to prepare Example 5(b), 4-(4-tert-butylphenyl)-6-chloro-3-phenylpyridazine (95 mg, 0.3 mmol) and 6-aminobenzothiazole (44 mg, 0.3 mmol, Lancaster) afforded the title compound as a white crystalline solid. MS (ESI, pos. ion) m/z: 437 (M+1). MP: 293-295° C.

Example 79

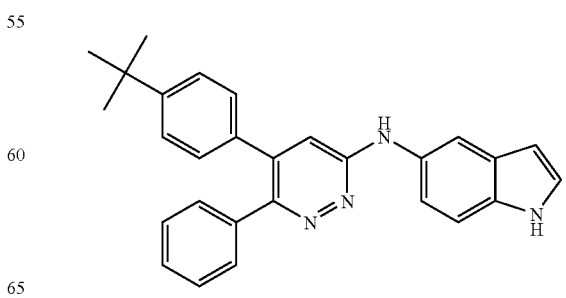

[5-(4-tert-Butylphenyl)-6-phenyl-pyridazin-3-yl]-(1H-indol-5-yl)-amine.

Analogous to the procedure used to prepare Example 5(b), 4-(4-tert-butylphenyl)-6-chloro-3-phenylpyridazine, Example 78(d), (95 mg, 0.3 mmol) and 5-aminoindole (39 mg, 0.3 mmol, Aldrich) afforded the title compound as a light-yellow crystalline solid. MS (ESI, pos. ion) m/z: 419 (M+1). MP: 138-140° C.

Example 80

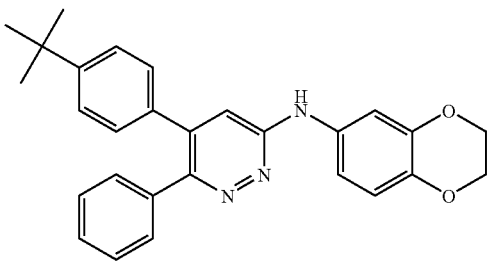

[5-(4-tert-Butylphenyl)-6-phenylpyridazin-3-yl]-(2,3-dihydrobenzo[1,4]-dioxin-6-yl)amine. Analogous to the procedure used to prepare Example 5(b), 4-(4-tert-butyl-phenyl)-6-chloro-3-phenylpyridazine, Example 78(d), (155 mg, 0.5 mmol) and 1,4-benzodioxan-6-amine (80 mg, 0.5 mmol, Aldrich) to give the product as a light yellow crystalline solid. MS (ESI, pos. ion) m/z: 438 (M+1).

Example 81

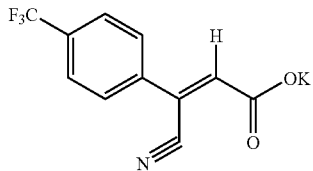

(a) Potassium (Z)-3-(4-trifluoromethylphenyl)-3-cyanopropenoate.

(Analogous to the procedure of Dan, W. D. and Blum, D. M. *J. Org. Chem.* 1993, 58, 7916-7917). Glyoxylic acid monohydrate (111.86 g, 1.22 mol, Aldrich) was added portion-wise to a suspension of potassium carbonate (284.4 g, 2.06 mol) in methanol (1.6 L) with stirring and cooling with a water bath. To the light-brown suspension was then added 4-trifluoromethylphenylacetonitrile (150 g, 0.81 mol, Aldrich) in small portions, the mixture was stirred for 5 h at room temperature, and the resulting thick solid precipitate was filtered and washed with dichloromethane. Concentration of the filtrate to a 600 mL volume led to the precipitation of additional amount of solid, which was filtered and washed with dichloromethane. The solids were combined and then suspended in cold water (4 L) to remove the excess of potassium carbonate. The precipitate was filtered, washed with water and air-dried to provide the title compound as a white solid, which was used in the next step without additional purification. MS (ESI, pos. ion) m/z: 279 (M).

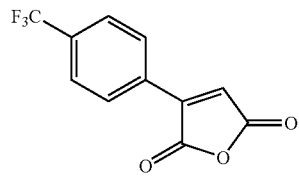

(b) 4-Trifluoromethylphenylmaleic anhydride. (Analogous to the procedure of Dan, W. D. and Blum, D. M. *J. Org. Chem.* 1993, 58, 7916-7917). Potassium (Z)-3-(4-trifluoromethylphenyl)-3-cyanopropenoate (100 g, 358 mmol) was dissolved in 88% formic acid (600 mL, Aldrich) containing concentrated sulfuric acid (45 mL) and the mixture heated at reflux for 3 h. The reaction mixture was then cooled and poured into ice water (1 L). The resulting solid was filtered, washed with water and air dried to give the title compound as a pale-yellow solid, which was used in the next step without additional purification. MS (ESI, pos. ion) m/z: 243 (M+1).

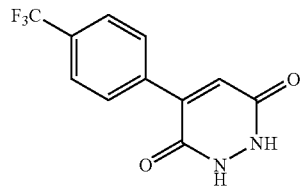

(c) 4-(4-Trifluoromethylphenyl)-1,2-dihydropyridazine-3,6-dione. (Analogous to the procedure of Augustin, M. and Reinemann, P. *Z. Chem.* 1973, 13, 12-13). 4-Trifluoromethylphenylmaleic anhydride (57.2 g, 235.8 mmol) was added to a mixture of water (325 mL) and acetic acid (88 mL), followed by the drop-wise addition of hydrazine hydrate (11.44 mL, 235.8 mmol, Aldrich) with stirring at room temperature. To the resulting pale-yellow suspension was then added drop-wise concentrated sulphuric acid (177 mL) with stirring and cooling in an ice bath, which led to the formation of a thick paste. The reaction mixture was heated at 100-115° C. for 3 h with stirring, and then cooled in an ice bath. The precipitate was washed with water until the filtrate showed neutral pH, and then was washed with diethyl ether (2×100 mL) and air-dried to give the title compound as a white solid, which was used in the next step without additional purification. MS (ESI, pos. ion) m/z: 257 (M+1).

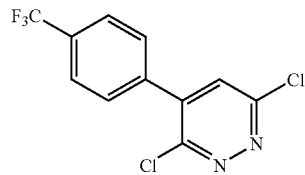

(d) 3,6-Dichloro-4-(4-trifluoromethylphenyl)pyridazine. (Analogous to the procedure of Augustin, M. and Reinemann, P. Z. *Chem.* 1973, 13, 12-13). A mixture of 4-(4-trifluoromethylphenyl)-1,2-dihydropyridazine-3,6-dione (25.6 g, 100 mmol) and phosphorus oxychloride (192 mL) was heated under reflux for 2 h with stirring under nitrogen atmosphere. The reaction mixture was cooled to room temperature and poured in small portions with energetically stirring into a mixture of water and crushed ice (2.6 L). The product separated as a white precipitate, which was filtered, washed with water (3×50 mL), dried under vacuo and recrystallized from dioxane/methanol to give the title compound as a white solid. MS (ESI, pos. ion) m/z: 293 (M+1).

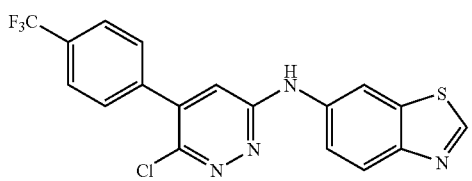

(e) Benzothiazol-6-yl-[6-chloro-5-(4-trifluoromethylphenyl)pyridazin-3-yl]amine. (Analogous to the procedure of JP02169579). To a solution of 3,6-dichloro-4-(4-trifluoromethylphenyl)pyridazine (1.465 g, 5 mmol) and 6-aminobenzothiazole (0.751 g, 5 mmol, Lancaster) in 1-butanol (6 mL) was added 37% hydrochloric acid (0.49 mL, 5 mmol) and the mixture heated at 75° C. for 18 h with stirring under nitrogen atmosphere. The reaction mixture was cooled to room temperature, diluted with ethyl acetate (200 mL) and water (300 mL), and stirred for 15 min at 60° C. The mixture was cooled to room temperature, the organic layer was separated and then washed with 1N hydrochloric acid (2×50 mL) and water (50 mL), dried over Na$_2$SO$_4$ and concentrated in vacuo. The residue was purified by silica gel chromatography with ethyl acetate/hexane (2:3) to give the title compound as an yellow solid. MS (ESI, pos. ion) m/z: 407 (M+1). MP: 206.3° C. (with decomposition).

Example 82

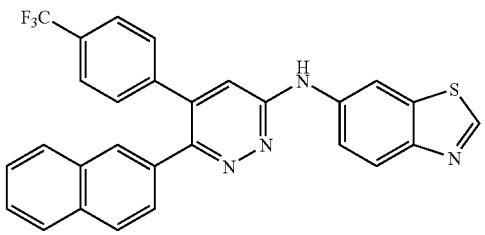

Benzothiazol-6-yl-[6-(2-naphthyl)-5-(4-trifluoromethylphenyl)pyridazin-3-yl] amine. (Ph$_3$P)$_2$PdCl$_2$ (0.026 g, 0.038 mmol, Strem) was added to a mixture of benzothiazol-6-yl-[6-chloro-5-(4-trifluoromethylphenyl)pyridazin-3-yl] amine (0.203 g, 0.5 mmol, Example 81(e), 2-naphthaleneboronic acid (0.129 g, 0.75 mmol, Aldrich), Na$_2$CO$_3$ (0.053 g, 0.5 mmol), dimethoxyethane (1.4 mL), EtOH (0.4 mL) and water (0.6 mL). The reaction mixture was heated in a microwave at 120° C. for 15 min with stirring under nitrogen. The reaction mixture was cooled to room temperature, diluted with ethyl acetate (50 mL), washed with 1N NaOH (20 mL) and water (2×20 mL), dried over Na$_2$SO$_4$ and concentrated in vacuo. The residue was purified by silica gel chromatography with ethyl acetate/hexane (1:1) to give the title compound as an yellow amorphous solid. MS (ESI, pos. ion) m/z: 499 (M+1).

ADDITIONAL EXAMPLES

Following the procedures described above in Scheme 2, or with slight modifications thereof, and following procedures familiar to one of ordinary skill in the art, the following examples were prepared from commercially available 6-aminobenzothiazole:

| Example | Structure | MS (ESI, pos. ion) m/z | Melting Point ° C. |
|---|---|---|---|
| 83 | 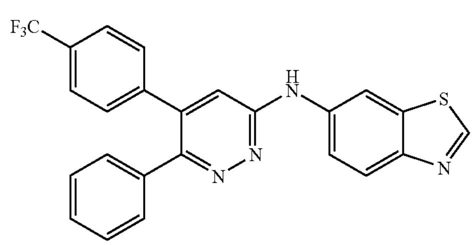 | 449 (M + 1) | 272 |

-continued

| Example | Structure | MS (ESI, pos. ion) m/z | Melting Point ° C. |
|---------|-----------|------------------------|--------------------|
| 84 | 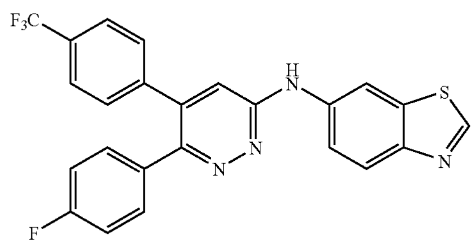 | 467 (M + 1) | 269 |
| 85 | 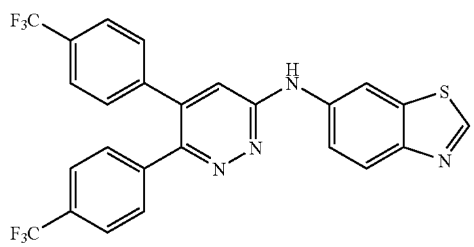 | 517 (M + 1) | 243 |
| 86 | 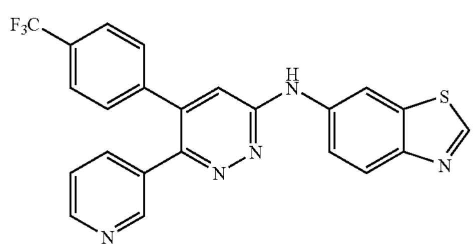 | 450 (M + 1) | amorphous |
| 87 | 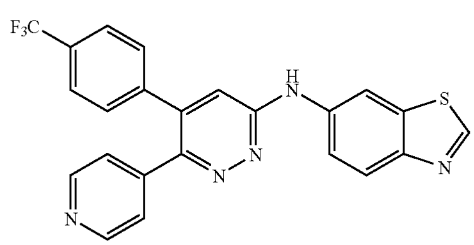 | 450 (M + 1) | amorphous |

Example 88

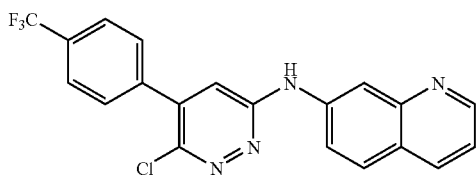

[6-Chloro-5-(4-trifluoromethylphenyl)pyridazin-3-yl]-[quinolin-7-yl]amine.

(Analogous to the procedure of WO 178270). A mixture of 3,6-dichloro-4-(4-trifluoromethylphenyl)pyridazine, Example 81(d), (2.0 g, 6.8 mmol), 7-amino-quinoline (984 mg, 6.8 mmol) and $ZnCl_2$ (980 mg, 3.4 mmol) was heated in a microwave with stirring at 220° C. for 20 min. The reaction mixture was cooled to room temperature, a second portion of 3,6-dichloro-4-(4-trifluoromethylphenyl)pyridazine (2.0 g, 6.8 mmol), was added and the mixture was heated again in microwave at 220° C. for 40 min. The reaction mixture was cooled to room temperature, diluted with EtOAc (50 mL) and washed with $H_2O$ (3×). The organic layer was dried over $Na_2SO_4$, filtered and the solvent evaporated in vacuo. The residue was purified by preparative thin layer chromatography, eluting with $MeOH:CH_2Cl_2$ (1:39), to give the title compound as a light-yellow powder. MS (ESI, pos. ion) m/z: 401 (M+1).

Example 89

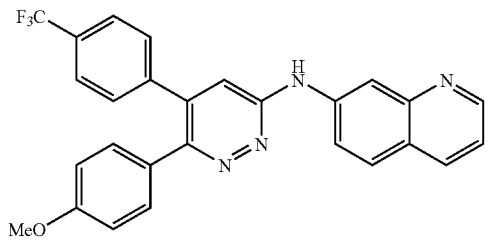

[6-(4-Methoxyphenyl)-5-(4-trifluoromethylphenyl)pyridazin-3-yl]-[quinolin-7-yl]amine. To a solution of [6-chloro-5-(4-trifluoromethylphenyl)pyridazin-3-yl]-[quinolin-7-yl]amine, Example 88, (100 mg, 0.3 mmol) in dioxane (2 mL) was added 4-methoxyphenylboronic acid (46 mg, 0.3 mmol, Aldrich), followed by the addition of 2M aq $Na_2CO_3$ (0.2 mL, 0.4 mmol) and $Pd[PPh_3]_4$ (35 mg, 0.03 mmol, Aldrich). The mixture was flushed with $N_2$ and heated under at 100° C. under $N_2$ atmosphere for 24 h. The reaction mixture was cooled to room temperature, additional amounts of 2M aq $Na_2CO_3$ (0.2 mL, 0.4 mmol), 4-methoxyphenylboronic acid (46 mg, 0.3 mmol) and $Pd[PPh_3]_4$ (35 mg, 0.03 mmol) were added and the mixture was heated at 100° C. with stirring under $N_2$ atmosphere for 4 h. The reaction mixture was cooled to room temperature, diluted with EtOAc (50 mL) and washed with 5% $Na_2CO_3$. The organic layer was dried over $Na_2SO_4$, filtered and the solvent evaporated in vacuo. The residue was purified by column chromatography, eluting with $MeOH:CH_2Cl_2$ (1:19), to give the title compound as a tan crystalline solid. MS (ESI, pos. ion) m/z: 473 (M+1). MP: 215-217° C.

Example 90

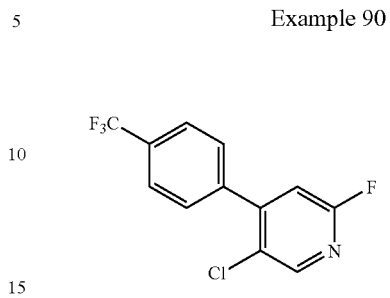

5-Chloro-2-fluoro-4-(4-trifluoromethyl-phenyl)-pyridine.

This compound was prepared analogous to Example 5(a) using 5-chlroro-2-fluoro-4-iodopyridine (0.64 g, 2.5 mmol, Asymchem), 4-(trifluoromethyl)-benzeneboronic acid (0.52 g, 2.8 mmol, Avocado), tetrakis(triphenylphosphine)-palladium(0) (0.29 g, 0.25 mmol, Aldrich) and aqueous sodium carbonate (0.29 g in 10 mL of water) in toluene (10 mL). After ISCO purification (EtOAc/hexanes=1:99 to 1:9 in 30 min), the title compound was isolated as a white solid. MS m/z: 276 (M+1).

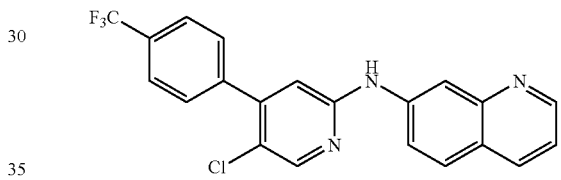

[5-Chloro-4-(4-trifluoromethyl-phenyl)-pyridin-2-yl]-quinolin-7-yl-amine.

This compound could be prepared by the method described in Example 6(d) from 5-chloro-2-fluoro-4-(4-trifluoromethyl-phenyl)-pyridine and 7-aminoquinoline by microwave in a Smith Synthesizer (Personal Chemistry) at 180° C. for 20 min. The product will be isolated using flash chromatography.

Example 91

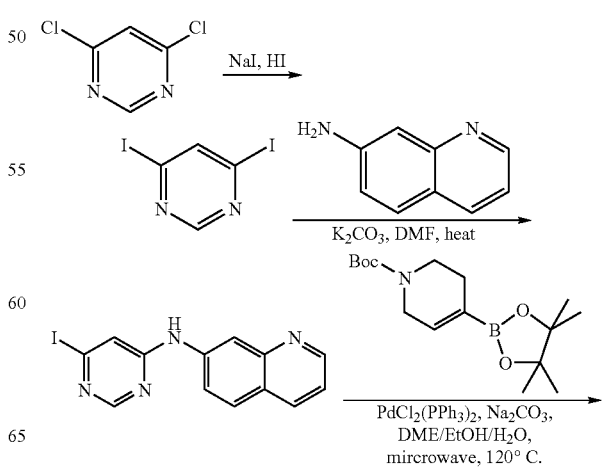

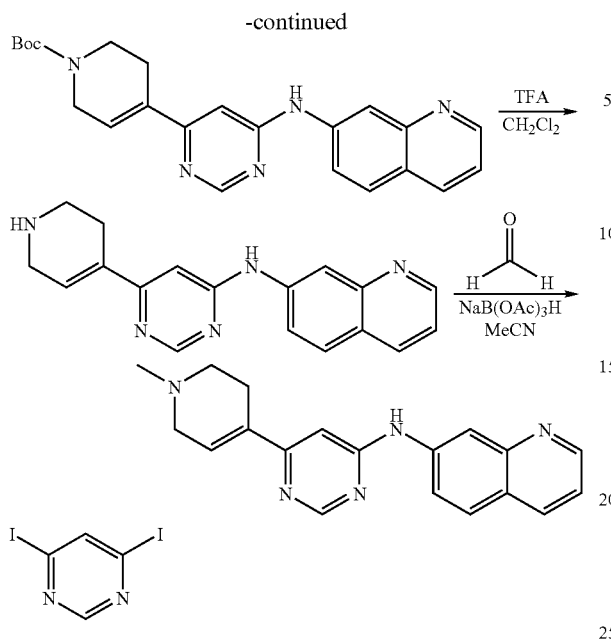

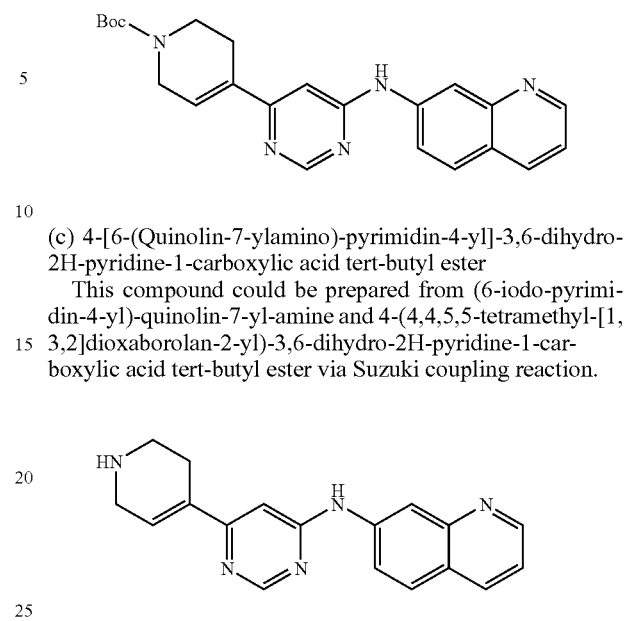

(c) 4-[6-(Quinolin-7-ylamino)-pyrimidin-4-yl]-3,6-dihydro-2H-pyridine-1-carboxylic acid tert-butyl ester This compound could be prepared from (6-iodo-pyrimidin-4-yl)-quinolin-7-yl-amine and 4-(4,4,5,5-tetramethyl-[1,3,2]dioxaborolan-2-yl)-3,6-dihydro-2H-pyridine-1-carboxylic acid tert-butyl ester via Suzuki coupling reaction.

(a) 4,6-Diiodo-pyrimidine

A mixture of 4,6-dichloro-pyrimidine (1.0 g, 6.70 mmol.), NaI (1.36 g, 9.00 mmol), and hydriodic acid (20 mL, 151.4 mmol.) was heated at 40° C. for 1 h and stirred at room temperature for additional 20 h. The reaction mixture was basified with 10 N NaOH aqueous (18 mL). The resulting precipitate was filtered, washed with water, and dried under high vacuo to give a light-yellow solid. MS (ESI, pos. ion) m/z: 332 (M+1).

(d) Quinolin-7-yl-[6-(1,2,3,6-tetrahydro-pyridin-4-yl]-pyrimidin-4-yl)-amine

This compound could be prepared from 4-[6-(quinolin-7-ylamino)-pyrimidin-4-yl]-3,6-dihydro-2H-pyridine-1-carboxylic acid tert-butyl ester in the presence of TFA and CH$_2$Cl$_2$.

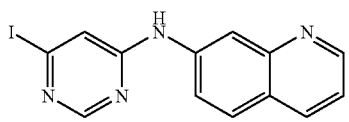

(b) (6-Iodo-pyrimidin-4-yl)-quinolin-7-yl-amine

This compound could be prepared from 4,6-diiodo-pyrimidine and 7-aminoquinoline in the presence of K$_2$CO$_3$ and DMF.

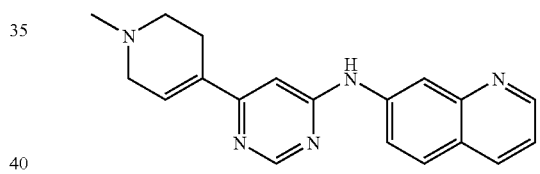

(e) [6-(1-Methyl-1,2,3,6-tetrahydro-pyridin-4-yl)-pyrimidin-4-yl]-quinolin-7-yl-amine This compound could be prepared from quinolin-7-yl-[6-(1,2,3,6-tetrahydro-pyridin-4-yl)-pyrimidin-4-yl]-amine and formaldehyde in the presence of sodium triacetoxyborohydride and MeCN.

Example 92

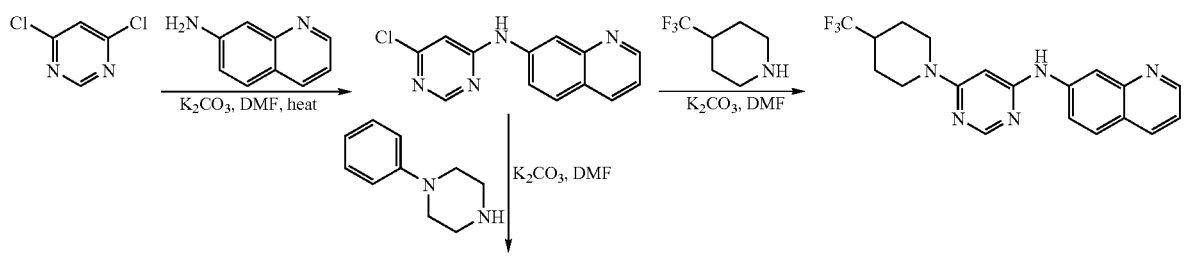

-continued

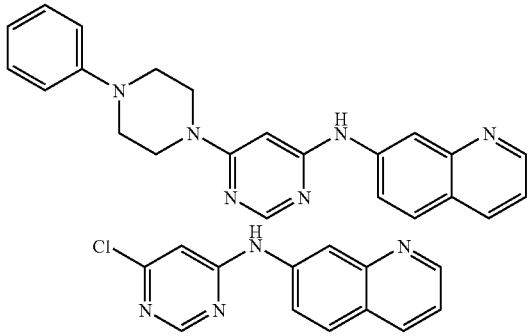

(a) (6-Chloro-pyrimidin-4-yl)-quinolin-7-yl-amine

This compound could be prepared from 4,6-dichloro-pyrimidine and 7-aminoquinoline in the presence of $K_2CO_3$ and DMF.

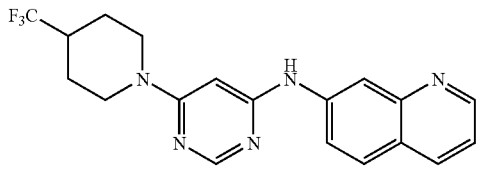

(b) Quinolin-7-yl-[6-(4-trifluoromethyl-piperidin-1-yl)-pyrimidin-4-yl]-amine

This compound could be prepared from (6-chloro-pyrimidin-4-yl)-quinolin-7-yl-amine and 4-trifluoromethyl-piperidine in the presence of $K_2CO_3$ and DMF.

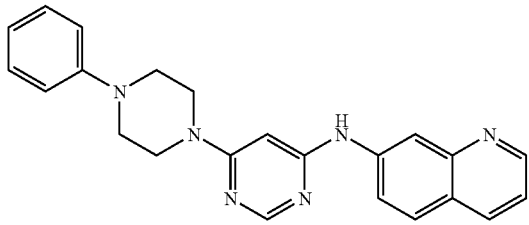

(c) [6-(4-Phenyl-piperazin-1-yl)-pyrimidin-4-yl]-quinolin-7-yl-amine

This compound could be prepared from (6-chloro-pyrimidin-4-yl)-quinolin-7-yl-amine and 1-phenyl-piperazine in the presence of $K_2CO_3$ and DMF.

Capsaicin-Induced $Ca^{2+}$ Influx in Primary Dorsal Root Ganglion Neurons

Embryonic 19 day old (E19) dorsal root ganglia (DRG) were dissected from timed-pregnant, terminally anesthetized Sprague-Dawley rats (Charles River, Wilmington, Mass.) and collected in ice-cold L-15 media (Life Technologies, Grand Island, N.Y.) containing 5% heat inactivated horse serum (Life Technologies). The DRG were then dissociated into single cell suspension using a papain dissociation system (Worthington Biochemical Corp., Freehold, N.J.). The dissociated cells were pelleted at 200×g for 5 min and re-suspended in EBSS containing 1 mg/mL ovomucoid inhibitor, 1 mg/mL ovalbumin and 0.005% DNase. Cell suspension was centrifuged through a gradient solution containing 10 mg/mL ovomucoid inhibitor, 10 mg/mL ovalbumin at 200×g for 6 min to remove cell debris; and filtered through a 88-μm nylon mesh (Fisher Scientific, Pittsburgh, Pa.) to remove any clumps. Cell number was determined with a hemocytometer and cells were seeded into poly-ornithine 100 μg/mL (Sigma) and mouse laminin 1 μg/mL (Life Technologies)-coated 96-well plates at $10 \times 10^3$ cells/well in complete medium. The complete medium consists of minimal essential medium (MEM) and Ham's F 12, 1:1, penicillin (100 U/mL), and streptomycin (100 μg/mL), and nerve growth factor (10 ng/mL), 10% heat inactivated horse serum (Life Technologies). The cultures were kept at 37° C., 5% $CO_2$ and 100% humidity. For controlling the growth of non-neuronal cells, 5-fluoro-2'-deoxyuridine (75 μM) and uridine (180 μM) were included in the medium. Activation of VR1 was achieved in these cellular assays using either a capsaicin stimulus (ranging from 0.01-110 μM) or by an acid stimulus (addition of 30 mM Hepes/Mes buffered at pH 4.1). Compounds were also tested in an assay format to evaluate their agonist properties at VR1. The activation of VR1 is followed as a function of cellular uptake of radioactive calcium ($^{45}Ca^{2+}$:Amersham CES3—2 mCi).

Capsaicin Antagonist Assay: E-19 DRG cells at 3 days in culture are incubated with serial concentrations of VR1 antagonists, in HBSS (Hanks buffered saline solution supplemented with BSA 0.1 mg/mL and 1 mM Hepes at pH 7.4) for 15 min, room temperature. Cells are then challenged with a VR1 agonist, capsaicin (500 nM), in activation buffer containing 0.1 mg/mL BSA, 15 mM Hepes, pH 7.4, and 10 μCi/mL $^{45}Ca^{2+}$ (Amersham CES3-2 mCi) in Ham's F12 for 2 min at room temperature.

The following compounds exhibit IC50 values of less than 10 mM in the Acid Antagonist Assay:

(1H-benzoimidazol-4-yl)-[6-(4-trifluoromethylphenyl)pyrimidin-4-yl]amine;
(1H-benzotriazol-5-yl)-[6-(4-trifluoromethylphenyl)pyrimidin-4-yl]amine;
(1H-indazol-5-yl)-[6-(4-trifluoromethylphenyl)pyrimidin-4-yl]amine;
(1H-indol-4-yl)-[6-(4-trifluoromethylphenyl)pyrimidin-4-yl]amine;
(1H-indol-5-yl)-[6-(4-trifluoromethylphenyl)pyrimidin-4-yl]amine;
(1H-indol-6-yl)-[6-(4-trifluoromethylphenyl)pyrimidin-4-yl]amine;
(1H-indol-7-yl)-[6-(4-trifluoromethyl]phenyl]pyrimidin-4-yl]amine;
(1-methyl-1H-benzoimidazol-4-yl)-[6-(4-trifluoromethyl)phenyl)pyrimidin-4-yl]amine;

(2,3-dihydrobenzo[1,4]dioxin-6-yl)-(6-phenylpyrimidin-4-yl)amine;
(2,3-dihydrobenzo[1,4]dioxin-6-yl)-[6-(4-trifluoromethylphenyl)pyrimidin-4-yl]amine;
(2,3-dimethyl-1H-indol-7-yl)-[6-(4-(trifluoromethylphenyl)pyrimidin-4-yl]amine;
(2-chloropyridin-3-yl)-[6-(4-trifluoromethylphenyl)pyrimidin-4-yl]amine;
(2-chloroquinolin-7-yl)-[6-(4-trifluoromethylphenyl)pyrimidin-4-yl]amine;
(2-chloroquinolin-8-yl)-[6-(4-trifluoromethylphenyl)pyrimidin-4-yl]amine;
(2-methoxyquinolin-7-yl)-[6-(4-trifluoromethylphenyl)pyrimidin-4-yl]amine;
(2-methyl-1H-benzoimidazol-4-yl)-[6-(4-trifluoromethylphenyl)pyrimidin-4-yl]-amine;
(2-methylaminoquinolin-7-yl)-[6-(4-trifluoromethylphenyl)pyrimidin-4-yl]amine dihydrochloride;
(2-methylbenzothiazol-5-yl)-[6-(4-trifluoromethylphenyl)pyrimidin-4-yl]amine;
(2R)-{6-[6-(4-trifluoromethylphenyl)pyrimidin-4-ylamino]-2H$^{13}$H-benzo[1,4]dioxin-2-yl}methanol;
(3,4-dichlorophenyl)-[6-(4-trifluoromethylphenyl)pyrimidin-4-yl]amine;
(3,4-dimethylphenyl)-[6-(4-trifluoromethylphenyl)pyrimidin-4-yl]amine;
(3-chloro-2-methylphenyl)-[6-(4-trifluoromethylphenyl)pyrimidin-4-yl]amine;
(3H-benzotriazol-5-yl)-[6-(4-tert-butylphenyl)pyrimidin-4-yl]amine;
(3-methanesulfonylphenyl)-[6-(4-trifluoromethylphenyl)pyrimidin-4-yl] amine;
(3-methylbenzo[d]isothiazol-5-yl)-[6-(4-trifluoromethylphenyl)pyrimidin-4-yl]amine;
(3-methylsulfanylphenyl)-[6-(4-trifluoromethylphenyl)pyrimidin-4-yl]amine;
(4-chloro-3-trifluoromethylphenyl)-[6-(4-trifluoromethylphenyl)pyrimidin-4-yl]amine;
(4-chlorophenyl)-[6-(4-trifluoromethylphenyl)pyrimidin-4-yl]amine;
(5,6,7,8-tetrahydro[1,8]naphthyridin-2-yl)-[6-(4-trifluoromethylphenyl)pyrimidin-4-yl]amine;
(5-chloro-2-methylphenyl)-[6-(4-trifluoromethylphenyl)pyrimidin-4-yl]amine;
(6-methoxypyridin-3-yl)-[6-(4-trifluoromethylphenyl)pyrimidin-4-yl]amine;
[(2-morpholin-4-yl)quinolin-7-yl]-[6-(4-trifluoromethylphenyl)pyrimidin-4-yl]amine hydrochloride;
[2-amino-6-(4-tert-butylphenyl)pyrimidin-4-yl]-(2,3-dihydrobenzo[1,4]dioxin-6-yl)amine hydrochloride;
[5-(4-tert-butylphenyl)-6-phenyl-pyridazin-3-yl]-(1H-indol-5-yl)-amine;
[5-(4-tert-butylphenyl)-6-phenylpyridazin-3-yl]-(2,3-dihydrobenzo[1,4]dioxin-6-yl)amine;
[6-(2-amino-4-trifluoromethylphenyl)pyrimidin-4-yl]benzothiazol-6-ylamine;
[6-(4-tert-butylphenyl)-2-chloropyrimidin-4-yl]-(2,3-dihydrobenzo[1,4]dioxin-6-yl)amine;
[6-(4-tert-butylphenyl)-2-methylpyrimidin-4-yl]-(2,3-dihydrobenzo[1,4]dioxin-6-yl)amine;
[6-(4-tert-butylphenyl)pyrimidin-4-yl]-(1H-indol-4-yl)amine;
[6-(4-tert-butylphenyl)pyrimidin-4-yl]-(1H-indol-5-yl)amine;
[6-(4-tert-butylphenyl)pyrimidin-4-yl]-(1H-indol-6-yl)amine;
[6-(4-tert-butylphenyl)pyrimidin-4-yl]-(2,3-dihydrobenzo[1,4]dioxin-6-yl)amine;
[6-(4-tert-butylphenyl)pyrimidin-4-yl]-(3-methoxyphenyl)amine;
[6-(4-tert-butylphenyl)pyrimidin-4-yl]naphthalen-1-ylamine;
[6-(4-tert-butylphenyl)pyrimidin-4-yl]phenylamine;
[6-(4-tert-butylphenylpyrimidin-4-yl]quinolin-3-ylamine;
{1'-acetylspiro [cyclopropane-1,3'-indolin-6'-yl]}-[6-(4-trifluoromethylphenyl)-pyrimidin-4-yl]amine;
{7-[6-(4-trifluoromethylphenyl)pyrimidin-4-ylamino]-1H-indol-2-yl} methanol;
{spiro[cyclopropane-1,3'-indolin-6'-yl]}-[6-(4-trifluoromethylphenyl)pyrimidin-4-yl]amine;
1-{3,3-dimethyl-6-[6-(4-trifluoromethylphenyl)pyrimidin-4-ylamino]-2,3-dihydroindol-1-yl}ethanone;
2-[6-(4-trifluoromethylphenyl)pyrimidin-4-ylamino]quinolin-8-ol;
2-{5-[6-(4-trifluoromethylphenyl)pyrimidin-4-ylamino]pyridin-2-yloxy} ethanol;
3,4-dihydro-7-[6-(4-trifluoromethylphenyl)pyrimidin-4-ylamino]-1H-quinolin-2-one;
4-methyl-7-{[6-(4-trifluoromethylphenyl)pyrimidin-4-yl]amino} quinolin-2-ol, hydrochloride;
6-[6-(4-tert-butylphenyl)pyrimidin-4-ylamino]-3,4-dihydro-2H-naphthalen-1-one;
7-[6-(4-trifluoromethylphenyl)pyrimidin-4-ylamino]quinolin-2-ol;
7-[6-(4-trifluoromethylphenyl)pyrimidin-4-ylamino]-1,3-dihydroindol-2-one;
benzothiazol-5-yl-[6-(4-trifluoromethylphenyl)pyrimidin-4-yl] amine;
benzothiazol-6-yl-[5-(4-tert-butylphenyl)-6-phenylpyridazin-3-yl] amine;
benzothiazol-6-yl-[5,6-bis-(4-trifluoromethylphenyl)pyridazin-3-yl]amine;
benzothiazol-6-yl-[6-(2-cyclohexylmethylamino-4-trifluoromethylphenyl)-pyrimidin-4-yl] amine;
benzothiazol-6-yl-[6-(2-naphthyl)-5-(4-trifluoromethylphenyl)pyridazin-3-yl]amine;
benzothiazol-6-yl-[6-(4-fluorophenyl)-5-(4-trifluoromethylphenyl)pyridazin-3-yl]amine;
benzothiazol-6-yl-[6-(4-tert-butylphenyl)pyrimidin-4-yl] amine;
benzothiazol-6-yl-[6-(4-trifluoromethylphenyl)pyrimidin-4-yl]amine;
benzothiazol-6-yl-[6-chloro-5-(4-trifluoromethylphenyl)pyridazin-3-yl]amine;
benzothiazol-6-yl-[6-phenyl-5-(4-trifluoromethylphenyl)pyridazin-3-yl]amine;
benzothiazol-6-yl-[6-pyridin-3-yl-5-(4-trifluoromethylphenyl)pyridazin-3-yl]amine;
benzothiazol-6-yl-[6-pyridin-4-yl-5-(4-trifluoromethylphenyl)pyridazin-3-yl]amine;
N-{4-[6-(4-trifluoromethylphenyl)pyrimidin-4-ylamino]-1H-benzoimidazol-2-yl}acetamide;
N-{4-[6-(4-trifluoromethylphenyl)pyrimidin-4-ylamino]benzothiazol-2-yl}acetamide;
N-{4-[6-(4-trifluoromethylphenyl)pyrimidin-4-ylamino]phenyl} acetamide;
$N^4$-[6-(4-trifluoromethylphenyl)pyrimidin-4-yl]-1H-benzoimidazole-2,4-diamine;
$N^4$-[6-(4-trifluoromethylphenyl)pyrimidin-4-yl]benzothiazole-2,4-diamine;
$N^4$-benzothiazol-6-yl-6-(4-tert-butylphenyl)pyrimidine-2,4-diamine hydrochloride;

N⁷-[6-(4-trifluoromethylphenyl)pyrimidin-4-yl]quinoline-2,7-diamine;
N⁸-[6-(4-trifluoromethylphenyl)pyrimidin-4-yl]quinoline-2,8-diamine;
naphthalen-1-yl-[6-(4-trifluoromethylphenyl)pyrimidin-4-yl]amine;
naphthalen-2-yl-[6-(4-trifluoromethylphenyl)pyrimidin-4-yl] amine;
o-tolyl-[6-(4-trifluoromethylphenyl)pyrimidin-4-yl]amine;
phenyl-[6-(4-trifluoromethylphenyl)pyrimidin-4-yl] amine;
p-tolyl-[6-(4-trifluoromethylphenyl)pyrimidin-4-yl] amine;
quinolin-3-yl-[6-(4-trifluoromethylphenyl)pyrimidin-4-yl] amine;
5 quinolin-5-yl-[6-(4-trifluoromethylphenyl)pyrimidin-4-yl] amine;
quinolin-6-yl-[6-(4-trifluoromethylphenyl)pyrimidin-4-yl] amine;
quinolin-8-yl-[6-(4-trifluoromethylphenyl)pyrimidin-4-yl] amine; and
quinolyl-7-yl-[6-(4-trifluoromethylphenyl)pyrimidin-4-yl] amine.

Acid Antagonist Assay: Compounds are pre-incubated with E-19 DRG cells at room temperature for 2 minutes prior to addition of $^{45}Ca^{2+}$ in 30 mM Hepes/Mes buffer (Final Assay pH 5) and then left for an additional 2 minutes prior to compound washout. Final concentration of $^{45}Ca^{2+}$ (Amersham CES3-2 mCi) is 10 µCi/mL.

Agonist Assay: Compounds are incubated with E-19 DRG cells at room temperature for 2 minutes in the presence of $^{45}Ca^{2+}$ prior to compound washout. Final $^{45}Ca^{2+}$ (Amersham CES3—2 mCi) at 10 µCi/mL.

Compound Washout and Analysis: Assay plates are washed using an ELX405 plate washer (Bio-Tek Instruments Inc.) immediately after functional assay. Wash 3× with PBS, 0.1 mg/nL BSA. Aspirate between washes. Read plates using a MicroBeta Jet (Wallac Inc.). Compound activity is then calculated using appropriate computational algorithms.

$^{45}$Calcium$^{2+}$ Assay Protocol

Compounds may be assayed using Chinese Hamster Ovary cell lines stably expressing either human VR1 or rat VR1 under a CMV promoter. Cells could be cultured in a Growth Medium, routinely passaged at 70% confluency using trypsin and plated in an assay plate 24 hours prior to compound evaluation.

Possible Growth Medium:
 DMEM, high glucose (Gibco 11965-084).
 10% Dialyzed serum (Hyclone SH30079.03).
 1× Non-Essential Amino Acids (Gibco 11140-050).
 1× Glutamine-Pen-Strep (Gibco 10378-016).
 Geneticin, 450 µg/mL (Gibco 10131-035).

Compounds could be diluted in 100% DMSO and tested for activity over several log units of concentration [40 µM-2 pM]. Compounds may be further diluted in HBSS buffer (pH 7.4) 0.1 mg/mL BSA, prior to evaluation. Final DMSO concentration in assay would be 0.5-1%. Each assay plate could be controlled with a buffer only and a known antagonist compound (either capsazepine or one of the described VR1 antagonists).

Activation of VR1 could be achieved in these cellular assays using either a capsaicin stimulus (ranging from 0.1-1 µM) or by an acid stimulus (addition of 30 mM Hepes/Mes buffered at pH 4.1). Compounds could also be tested in an assay format to evaluate their agonist properties at VR1.

Capsaicin Antagonist Assay: Compounds may be pre-incubated with cells (expressing either human or rat VR1) at room temperature for 2 minutes prior to addition of $^{45}Ca^{2+}$ and Capsaicin and then left for an additional 2 minutes prior to compound washout. Capsaicin (200 nM) can be added in HAM's F12, 0.1 mg/mL BSA, 15 mM Hepes at pH 7.4. Final $^{45}Ca^{2+}$ (Amersham CES3—2 mCi) added could be 10 µCi/mL.

Acid Antagonist Assay: Compounds can be pre-incubated with cells (expressing either human or rat VR1) for 2 minutes prior to addition of $^{45}Ca^{2+}$ in 30 mM Hepes/Mes buffer (Final Assay pH 5) and then left for an additional 2 minutes prior to compound washout. Final $^{45}Ca^{2+}$ (Amersham CES3—2 mCi) added could be 10 µCi/mL.

Agonist Assay: Compounds can be incubated with cells (expressing either human or rat VR1) for 2 minutes in the presence of $^{45}Ca^{2+}$ prior to compound washout. Final $^{45}Ca^{2+}$ (Amersham CES3—2 mCi) added could be 10 µCi/mL.

Compound Washout and Analysis: Assay plates would be washed using an ELX405 plate washer (Bio-Tek Instruments Inc.) immediately after the functional assay. One could wash 3× with PBS, 0.1 mg/mL BSA, aspirating between washes. Plates could then be read using a MicroBeta Jet (Wallac Inc.) and compound activity calculated using appropriate computational algorithms.

Useful nucleic acid sequences and proteins may be found in U.S. Pat. Nos. 6,335,180, 6, 406,908 and 6,239,267, herein incorporated by reference in their entirety.

For the treatment of vanilloid-receptor-diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrastemal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating vanilloid-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g, from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$) alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:
1. A compound having the structure:

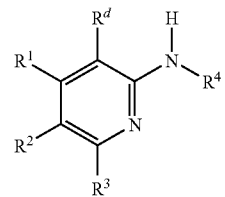

or any pharmaceutically-acceptable salt thereof, wherein:
n is independently, at each instance, 0, 1 or 2;
$R^1$ is

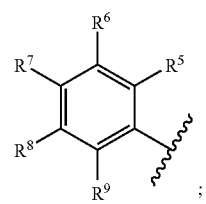

;

or $R^1$ is a naphthyl substituted by 0, 1, 2 or 3 substituents independently selected from $R^5$; or $R^1$ is $R^b$ substituted by 1, 2 or 3 substituents independently selected from $R^5$;

$R^2$ is, independently, in each instance, $R^{10}$, $C_{1-8}$alkyl substituted by 0, 1 or 2 substituents selected from $R^{10}$, —(CH$_2$)$_n$phenyl substituted by 0, 1, 2 or 3 substituents independently selected from R$^{10}$, or a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the heterocycle or fused phenyl ring is substituted by 0, 1, 2 or 3 substituents independently selected from R$^{10}$;

R$^3$ is, independently, in each instance, H, halo, —NHC$_{1-3}$alkyl, —N(C$_{1-3}$alkyl)C$_{1-3}$alkyl, or C$_{1-3}$alkyl; wherein, at least one of R$^2$ and R$^3$ is other than H;

R$^4$ is

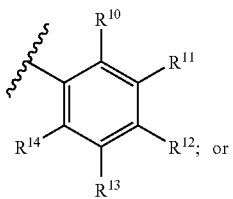

R$^4$ is a saturated or unsaturated 5- or 6-membered ring heterocycle containing 1, 2 or 3 atoms selected from O, N and S that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from R$^e$, C$_{1-4}$haloalkyl, halo, nitro, cyano, oxo, —OR$^f$, —S(═O)$_n$R$^e$, —OC$_{1-4}$haloalkyl, —OC$_{2-6}$alkylNR$^a$R$^f$, —OC$_{2-6}$alkylOR$^f$, —OC$_{1-6}$alkylC(═O)OR$^e$, —NR$^a$R$^f$, —NR$^a$C$_{1-4}$haloalkyl, —NR$^a$C$_{2-6}$alkylNR$^a$R$^f$, —NR$^a$C$_{2-6}$alkylOR$^f$, —C(═O)R$^e$, —C(═O)OR$^e$, —OC(═O)R$^e$, —C(═O)NR$^a$R$^f$ and —NR$^a$C(═O)R$^e$; and unsaturated carbon atoms may be additionally substituted by ═O; and any available nitrogen atoms in the heterocycle and bridge are substituted by H, —C$_{1-6}$alkylOR$^f$, R$^e$, —C$_{1-6}$alkylNR$^a$R$^f$, —C$_{1-3}$alkylC(═O)OR$^e$, —C$_{1-3}$alkylC(═O)NR$^a$R$^f$, —C$_{1-3}$alkylOC(═O)R$^e$, —C$_{1-3}$alkylNR$^a$C(═O)R$^e$, —C(═O)R$^c$ or —C$_{1-3}$alkylR$^e$; or R$^4$ is naphthyl substituted by 1, 2 or 3 substituents independently selected from C$_{1-4}$haloalkyl, halo, nitro, cyano, —S(═O)$_n$R$^e$, —OC$_{1-4}$haloalkyl, —OC$_{2-6}$alkylNR$^a$R$^f$, —OC$_{2-6}$alkylOR$^f$, —OC$_{1-6}$alkylC(═O)OR$^e$, —NR$^a$C$_{1-4}$haloalkyl, —NR$^a$C$_{2-6}$alkylNR$^a$R$^f$, —NR$^a$C$_{2-6}$alkylOR$^f$, —C(═O)R$^e$, —C(═O)OR$^e$, —OC(═O)R$^e$ and —C(═O)NR$^a$R$^f$; but in no instance is R$^4$ 3,5-ditrifluoromethylphenyl, 3-trifluoromethyl-4-fluorophenyl, -phenyl-(C$_{1-8}$alkyl), -phenyl-O—(C$_{1-6}$alkyl), -phenyl-NR$^a$R$^a$ or -phenyl-N(R$^a$)C(═O)(C$_{1-8}$alkyl);

R$^5$ is independently, at each instance, R$^f$, R$^g$, halo, nitro, cyano, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(═O)R$^e$, —C(═O)NR$^a$R$^f$, —C(═O)NR$^a$R$^g$, —NR$^f$C(═O)R$^e$, —NR$^f$C(═O)R$^g$, —NR$^f$C(═O)NR$^a$R$^f$, —NR$^f$CO$_2$R$^e$, —C$_{1-8}$alkylOR$^f$, —C$_{1-6}$alkylNR$^a$R$^f$, —S(═O)$_n$R$^e$, —S(═O)$_2$NR$^a$R$^f$, —NR$^a$S(═O)$_2$R$^e$, —C(═O)NR$^a$R$^f$, a phenyl ring substituted with 0, 1, 2, or 3 substituents independently selected from R$^{10}$; or R$^5$ is a saturated or unsaturated 5- or 6-membered ring heterocycle containing 1, 2 or 3 atoms selected from O, N and S, substituted with 0, 1, 2, or 3 substituents independently selected from R$^{10}$;

R$^6$ is independently, at each instance, H, C$_{1-5}$alkyl, C$_{1-4}$haloalkyl, halo, —OC$_{1-6}$alkyl, —OC$_{1-4}$haloalkyl, —OC$_{2-6}$ alkylNR$^a$R$^a$, —OC$_{2-6}$alkylOR$^a$, —NR$^a$R$^a$, —NR$^a$C$_{1-4}$ haloalkyl, —NR$^a$C$_{2-6}$alkylNR$^a$R$^a$ or —NR$^a$C$_{2-6}$ alkylOR$^a$, —C$_{1-8}$alkylOR$^a$, —C$_{1-6}$alkylNR$^a$R$^a$, —S(C$_{1-6}$alkyl), a phenyl ring substituted with 1, 2, or 3 substituents independently selected from R$^{10}$; or R$^6$ is a saturated or unsaturated 5- or 6-membered ring heterocycle containing 1, 2 or 3 atoms selected from O, N and S substituted with 0, 1, 2, or 3 substituents independently selected from R$^{10}$;

R$^7$ is independently, at each instance, H, acyclicC$_{1-8}$alkyl, C$_{1-4}$haloalkyl, halo, —OC$_{1-6}$alkyl, —OC$_{1-4}$haloalkyl, —OC$_{2-6}$alkylNR$^a$R$^a$, —OC$_{2-6}$alkylOR$^a$, —NR$^a$R$^a$, —NR$^a$C$_{1-4}$haloalkyl, —NR$^a$C$_{2-6}$alkylNR$^a$R$^a$, —NR$^a$C$_{2-6}$alkylOR$^a$, —C$_{1-8}$alkylOR$^a$, —C$_{1-6}$alkylNR$^a$R$^a$ or —S(C$_{1-6}$alkyl); or R$^7$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl;

R$^8$ is independently, at each instance, H, C$_{1-5}$alkyl, C$_{1-4}$haloalkyl, halo, —OC$_{1-6}$alkyl, —OC$_{1-4}$haloalkyl, —OC$_{2-6}$ alkylNR$^a$R$^a$, —OC$_{2-6}$alkylOR$^a$, —NR$^a$R$^a$, —NR$^a$C$_{1-4}$ haloalkyl, —NR$^a$C$_{2-6}$alkylNR$^a$R$^a$, —NR$^a$C$_{2-6}$ alkylOR$^a$, —C$_{1-8}$alkylOR$^a$, —C$_{1-6}$alkylNR$^a$R$^a$, —S(C$_{1-6}$alkyl), a phenyl ring substituted with 1, 2, or 3 substituents independently selected from R$^{10}$, or R$^8$ is a saturated or unsaturated 5- or 6-membered ring heterocycle containing 1, 2 or 3 atoms selected from O, N and S substituted with 0, 1, 2, or 3 substituents independently selected from R$^{10}$;

R$^9$ is independently, at each instance, R$^f$, R$^g$, halo, nitro, cyano, —OR$^e$, —OR$^g$, —OC$_{2-6}$alkylNR$^a$R$^f$, —OC$_{2-6}$ alkylOR$^f$, —NR$^a$R$^f$, —NR$^a$R$^g$, —NR$^f$C$_{2-6}$ alkylNR$^a$R$^f$, —NR$^f$C$_{2-6}$alkylOR$^f$, naphthyl, —CO$_2$R$^e$, —C(═O)R$^e$, —C(═O)NR$^a$R$^f$, —C(═O)NR$^a$R$^g$, —NR$^f$C(═O)R$^e$, —NR$^f$C(═O)R$^g$, —NR$^f$C(═O)NR$^a$R$^f$, —NR$^f$CO$_2$R$^e$, —C$_{1-8}$alkylOR$^f$, —C$_{1-6}$alkylNR$^a$R$^f$, —S(═O)$_n$R$^e$, —S(═O)$_2$NR$^a$R$^f$, —NR$^a$S(═O)$_2$R$^e$, —OC(═O)NR$^a$R$^f$, a phenyl ring substituted with 0, 1, 2, or 3 substituents independently selected from R$^{10}$; or R$^9$ is a saturated or unsaturated 5- or 6-membered ring heterocycle containing 1, 2 or 3 atoms selected from O, N and S substituted with 0, 1, 2, or 3 substituents independently selected from R$^{10}$; or R$^9$ is a saturated or unsaturated 4- or 5-membered ring heterocycle containing a single nitrogen atom, wherein the ring is substituted with 0, 1 or 2 substituents independently selected from halo, C$_{1-2}$haloalkyl and C$_{1-3}$alkyl; wherein at least one of R$^5$, R$^6$, R$^7$, R$^8$ and R$^9$ is C$_{1-5}$alkyl, C$_{1-4}$haloalkyl, halo, —OC$_{1-4}$haloalkyl, —OC$_{2-6}$alkylNR$^a$R$^a$, —OC$_{2-6}$alkylOR$^a$, —NR$^a$C$_{1-4}$haloalkyl, —NR$^a$C$_{2-6}$alkylNR$^a$R$^a$, —NR$^a$C$_{2-6}$alkylOR$^a$, —C$_{1-8}$alkylOR$^a$, —C$_{1-6}$alkylNR$^a$R$^a$ or —S(C$_{1-6}$alkyl); and A) R$^{10}$ is independently, at each instance, selected from H, C$_{1-8}$alkyl, C$_{1-4}$haloalkyl, halo, cyano, nitro, —C(═O)(C$_{1-8}$alkyl), —C(═O)O(C$_{1-8}$alkyl), —C(═O)NR$^a$R$^a$, —C(═NR$^a$)NR$^a$R$^a$, —OR$^a$, —OC(═O)(C$_{1-8}$alkyl), —OC(═O)NR$^a$R$^a$, —OC(═O)N(R$^a$)S(═O)$_2$(C$_{1-8}$alkyl), —OC$_{2-6}$ alkylNR$^a$R$^a$, —OC$_{2-6}$alkylOR$^a$, —SR$^a$, —S(═O)(C$_{1-8}$ alkyl), —S(═O)$_2$(C$_{1-8}$alkyl), —S(═O)$_2$NR$^a$R$^a$, —S(═O)$_2$ N(R$^a$)C(═O)(C$_{1-8}$alkyl), —S(═O)$_2$N(R$^a$)C(═O)O(C$_{1-8}$alkyl), —S(═O)$_2$N(R$^a$)C(═O)NR$^a$R$^a$, —NR$^a$R$^a$, —N(R$^a$)C(═O)(C$_{1-8}$alkyl), —N(R$^a$)C(═O)O(C$_{1-8}$alkyl), —N(R$^a$)C(═O)NR$^a$R$^a$, —N(R$^a$)C(═NR$^a$)NR$^a$R$^a$, —N(R$^a$)S(═O)$_2$(C$_{1-8}$alkyl), —N(R$^a$)S(═O)$_2$ NR$^a$R$^a$, —NR$^a$C$_{2-6}$alkylNR$^a$R$^a$ and —NR$^a$C$_{2-6}$alkylOR$^a$; or R$^{10}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$ alkyl), —S(=O)$_2$N(R$^a$)C(=O)O(C$_{1-8}$alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; and R$^{11}$ and R$^{12}$ together are a saturated or unsaturated 3- or 4-atom bridge containing 1, 2 or 3 atoms selected from O, N and S with the remaining atoms being carbon, so long as the combination of O and S atoms is not graeter than 2, wherein the bridge is substituted by 0,1 or 2 substituted selected from =O, R$^e$, halo, cyano, nitro —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$; wherin when R$^3$ is NH$_2$, then —R$^{11}$—R$^{12}$— is not —C=C—C=N— or any substituted version thereof; or B) R$^{10}$ and R$^{11}$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$; and R$^{12}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkyNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$ NR$^a$R$^a$, —S(=O)$_2$N(R$^a$)C(=O)(C$_{1-8}$alkyl), —S(=O)$_2$N(R$^a$)C(=O)O(C$_{1-8}$alkyl), —S(=O)$_2$ N(R$^a$)C(=O)NR$^a$R$^a$, —N(R$^a$)C(=O)(C$_{1-8}$ alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$ alkyl), —N(R$^a$)S(=O)$_2$NR$^a$R$^a$, —NR$^a$C$_{2-6}$alkyl-NR$^a$R$^a$ and —NR$^a$C$_{2-6}$alkylOR$^a$; or R$^{12}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$ alkyl), —S(=O)$_2$N(R$^a$)C(=O)NR$^a$R$^a$, —NR$^a$R$^a$, —N(R$^a$)C(=O)(C$_{1-8}$alkyl) —N(R$^a$)C(=O)O(C$_{1-8}$ alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$ NR$^a$R$^a$, —NR$^a$C$_{2-6}$alkylNR$^a$R$^a$ and —NR$^a$C$_{2-6}$alkylOR$^a$; or R$^{12}$ is C$_{1-4}$alkyl substituted by 0, 1, 2 or 3 groups selected from C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$ alkyl), —S(=O)$_2$NR$^a$R$^a$, —S(=O)$_2$N(R$^a$)C(=O)(C$_{1-8}$alkyl), —S(=O)$_2$N(R$^a$)C(=O)O(C$_{1-8}$ alkyl), —S(=O)$_2$N(R$^a$)C(=O)NR$^a$R$^a$, —NR$^a$R$^a$, —N(R$^a$)C(=O)(C$_{1-8}$alkyl), —N(R$^a$)C(=O)O(C$_{1-8}$ alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$ NR$^a$R$^a$, —NR$^a$C$_{2-6}$alkylNR$^a$R$^a$ and —NR$^a$C$_{2-6}$alkylOR$^a$;

R$^{13}$ is independently, at each instance, selected from H, C$_{1-8}$alkyl, C$_{1-4}$haloalkyl, halo, cyano, nitro, —C(=O)(C$_{1-8}$alkyl), —C(=O)O(C$_{1-8}$alkyl), —C(=O)NR$^a$R$^a$, —C(=NR$^a$)NR$^a$R$^a$, —OR$^a$, —OC(=O)(C$_{1-8}$alkyl), —OC(=O)NR$^a$R$^a$, —OC(=O)N(R$^a$)S(=O)$_2$(C$_{1-8}$alkyl), —OC$_{2-6}$alkylNR$^a$R$^a$, —OC$_{2-6}$alkylOR$^a$, —SR$^a$, —S(=O)(C$_{1-8}$alkyl), —S(=O)$_2$(C$_{1-8}$alkyl), —S(=O)$_2$ NR$^a$R$^a$, —S(=O)$_2$N(R$^a$)C(=O)(C$_{1-8}$ alkyl), —S(=O)$_2$N(R$^a$)C(=O)O(C$_{1-8}$alkyl), —S(=O)$_2$ N(R$^a$)C(=O)NR$^a$R$^a$, —NR$^a$R$^a$, —N(R$^a$)C(=O)(C$_{1-8}$ alkyl), —N(R$^a$)C(=O)O(C$_{1-8}$alkyl), —N(R$^a$)C(=O)NR$^a$R$^a$, —N(R$^a$)C(=NR$^a$)NR$^a$R$^a$, —N(R$^a$)S(=O)$_2$(C$_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or $R^{13}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$-haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$ alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$ alkylNR$^a$R$^a$ and —NR$^a$C$_{2-6}$alkylOR$^a$; or $R^{13}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$ alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$;

$R^{14}$ is independently, at each instance, selected from H, $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$NR$^a$R$^a$, —S(=O)$_2$N(R$^a$)C(=O)($C_{1-8}$ alkyl), —S(=O)$_2$N(R$^a$)C(=O)O($C_{1-8}$alkyl), —S(=O)$_2$N(R$^a$)C(=O)NR$^a$R$^a$, —NR$^a$R$^a$, —N(R$^a$)C(=O)($C_{1-8}$ alkyl), —N(R$^a$)C(=O)O($C_8$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$ alkylNR$^a$R$^a$ and —NR$^a$C$_{2-6}$alkylOR$^a$; or $R^{14}$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($C_{1-8}$alkyl), —C(=O)O($C_{1-8}$alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$ alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$alkyl), —S(=O)$_2$ NR$^a$R$^a$, —S(=O)$_2$N(R$^a$)C(=O)($C_{1-8}$ alkyl), —S(=O)$_2$N(R$^a$)C(=O)O($C_{1-8}$alkyl), —S(=O)$_2$ N(R$^a$)C(=O)NR$^a$R$^a$, —NR$^a$R$^a$, —N(R$^a$)C(=O)($C_{1-8}$ alkyl), —N(R$^a$)C(=O)O($C_{1-8}$alkyl), —N(R$^a$)C(=O)NR$^a$R$^a$, —N(R$^a$)C(=NR$^a$)NR$^a$R$^a$, —N(R$^a$)S(=O)$_2$($C_{1-8}$alkyl), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or $R^{14}$ is $C_{1-4}$alkyl substituted by 0, 1, 2 or 3 groups selected from $C_{1-4}$haloalkyl, halo, cyano, nitro, —C(=O)($C_{1-8}$alkyl), —C(=O)O(C18alkyl), —C(=O)NR$^a$R$^a$, —C(=NR$^a$)NR$^a$R$^a$, —OR$^a$, —OC(=O)($C_{1-8}$alkyl), —OC(=O)NR$^a$R$^a$, —OC(=O)N(R$^a$)S(=O)$_2$($C_{1-8}$alkyl), —OC$_{2-6}$alkylNR$^a$R$^a$, —OC$_{2-6}$alkylOR$^a$, —SR$^a$, —S(=O)($C_{1-8}$alkyl), —S(=O)$_2$($C_{1-8}$ alkyl), —S(=O)$_2$NR$^a$R$^a$, —S(=O)$_2$N(R$^a$)C(=O)($C_{1-8}$alkyl), —S(=O)$_2$N(R$^a$)C(=O)O($C_{1-8}$ alkyl), —S(=O)$_2$N(R$^a$)C(=O)NR$^a$R$^a$, —NR$^a$R$^a$, —N(R$^a$)C(=O)($C_{1-8}$alkyl), —N(R$^a$)C(=O)O($C_{1-8}$ alkyl), —N(R$^a$)C(=O)NR$^a$R$^a$, —N(R$^a$)C(=NR$^a$) NR$^a$R$^a$, —N(R$^a$)S(=O)$_2$($C_{1-8}$alkyl), —N(R$^a$)S(=O)$_2$ NR$^a$R$^a$, —NR$^a$C$_{2-6}$alkylNR$^a$R$^a$ and —NR$^a$C$_{2-6}$alkylOR$^a$; wherein at least one of $R^{10}$, $R^{11}$, $R^{12}$, $R^{13}$ and $R^{14}$ is other than H;

$R^a$ is independently, at each instance, H, phenyl, benzyl or $C_{1-6}$alkyl;

$R^b$ is a heterocycle selected from the group of thiophene, pyrrole, 1,3-oxazole, 1,3-thiazole, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, imidazol-1-yl, imidazol-4-yl, 1,2,4-triazol-4-yl, 1,2,4-triazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazoline, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazole, 2,3-dihydro-1H-[1,2,4]triazole, 4,5-dihydro-1H-[1,2,4] triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4] thidiazole, 2,5-dihydro-[1,2,4] thiadiazole, 4,5-dihydro-[1,2,4]thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4]thiadiazole, 4,5-dihydro-[1,2,4] thiadiazole, 2,3-dihydro-[1,3,4]oxadiazole, 2,3-dihydro-[1,3,4]thiadiazole, [1,4,2]oxathiazole, [1,3,4] oxathiazole, 1,3,5-triazaperhydroine, 1,2,4- triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2] thiazine, 3,6-dihydro-2H-[1,2] thiazine, 3,4-dihydro-2H-[1,2]thiazine, 5,6-dihydro-2H-[1,3]oxazine, 5,6-dihydro-4H-[1,3]oxazine, 3,6-dihydro-2H-[1,3]oxazine, 3,4-dihydro-2H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 4,5-dihydropyridine, 1,6-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 2,3-dihydropyrimidine, 2,5-dihydropyrimidine, 5,6-dihydropyrimidine, 3,6-dihydropyrimidine, 4,5-dihydropyrazine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3-oxadi-azine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine and 1,4,2-oxathiazine, wherein the heterocycle is optionally vicinally fused with a saturated or unsaturated 5-, 6- or 7-membered ring containing 0, 1 or 2 atoms independently selected from N, O and S;

$R^c$ is independently, in each instance, phenyl substituted by 0, 1 or 2 groups selected from halo, $C_{1-4}$alkyl, $C_{1-3}$haloalkyl, —$OR^a$ and —$NR^aR^a$; or $R^c$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, $C_{1-4}$alkyl, $C_{1-3}$haloalkyl, —$OR^a$ and —$NR^aR^a$;

$R^d$ is hydrogen or —$CH_3$;

$R^e$ is, independently, in each instance, $C_{1-8}$alkyl substituted by 0, 1, 2, 3 or 4 substituents selected from halo, cyano, nitro, —C(=O)$R^b$, —C(=O)O$R^b$, —C(=O)N$R^aR^a$, —C(=N$R^a$)N$R^aR^a$, —$OR^a$, —OC(=O)$R^b$, —OC(=O)N$R^aR^a$, —OC(=O)N($R^a$)S(=O)$_2R^b$, —$OC_{2-6}$alkylN$R^aR^a$, —$OC_{2-6}$alkylO$R^a$, —$SR^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$; and wherein the $C_{1-8}$alkyl is additionally substituted by 0 or 1 groups independently selected from $R^g$;

$R^f$ is, independently, in each instance, $R^e$ or H; and $R^g$ is, independently, in each instance, a saturated or unsaturated 5- or 6-membered monocyclic ring containing 1, 2 or 3 atoms selected from N, O and S, so long as the combination of O and S atoms is not greater than 2, wherein the carbon atoms of the ring are substituted by 0 or 1 oxo groups.

2. A compound according to claim 1, wherein:

$R^1$ is

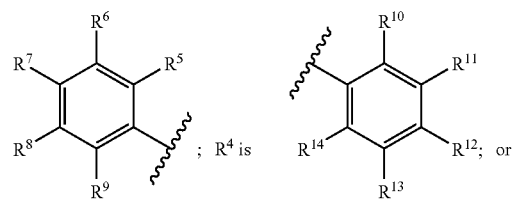

; $R^4$ is $R^4$ is a saturated or unsaturated 5- or 6-membered ring heterocycle containing 1, 2 or 3 atoms selected from O, N and S that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from $R^e$, $C_{1-4}$haloalkyl, halo, nitro, cyano, oxo, —$OR^f$, —S(=O)$_nR^e$, —$OC_{1-4}$haloalkyl, —$OC_{2-6}$alkylN$R^aR^f$, —$OC_{2-6}$alkylOR$^f$, —OC$_{1-6}$alkylC(=O)OR$^e$, —NR$^a$R$^f$, —NR$^a$C$_{1-4}$haloalkyl, —NR$^a$C$_{2-6}$alkylNR$^a$R$^f$, —NR$^a$C$_{2-6}$alkylOR$^f$, —C(=O)R$^e$, —C(=O)OR$^e$, —OC(=O)R$^e$, —C(=O)NR$^a$R$^f$ and —NR$^a$C(=O)R$^e$; and unsaturated carbon atoms may be additionally substituted by =O; and any available nitrogen atoms in the heterocycle and bridge are substituted by H, —C$_{1-6}$alkylOR$^f$, R$^e$, —C$_{1-6}$alkylNR$^a$R$^f$, —C$_{1-3}$alkylC(=O)OR$^e$, —C$_{1-3}$alkylC(=O)NR$^a$R$^f$, —C$_{1-3}$alkylOC(=O)R$^e$, —C$_{1-3}$alkylNR$^a$C(=O)R$^e$, —C(=O)R$^c$ or —C$_{1-3}$alkylR$^c$;

R$^7$ is independently, at each instance, C$_{3-5}$alkyl or C$_{1-2}$haloalkyl; and R$^{10}$ and R$^{11}$ together are a saturated or unsaturated 3-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R, —N(R$^f$)S(=O)$_2$ R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$; or, alternatively, R$^{11}$ and R$^{12}$ together form a —R$^{11}$—R$^{12}$-bridge selected from —O—C=C—O—, —N—C=C—C— and —N=C—C=C—, wherein the bridge is substituted by 0, 1 or 2 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$.

3. A compound according to claim 1, wherein R$^1$ is

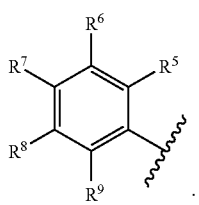

4. A compound according to claim 1, wherein R$^1$ is R$^b$ substituted by 1, 2 or 3 substituents independently selected from R$^5$.

5. A compound according to claim 1, wherein R$^4$ is

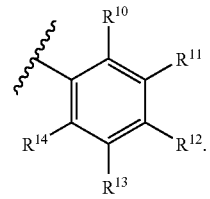

6. A compound according to claim 1, wherein R$^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from R$^e$, C$_{1-4}$haloalkyl, halo, nitro, cyano, oxo, —OR$^f$, —S(=O)$_n$R$^e$, —OC$_{1-4}$haloalkyl, —OC$_{2-6}$alkylNR$^a$R$^f$, —OC$_{2-6}$alkylOR$^f$, —OC$_{1-6}$alkylC(=O)OR$^e$, —NR$^a$R$^f$, —NR$^a$C$_{1-4}$haloalkyl, —NR$^a$C$_{2-6}$alkylNR$^a$R$^f$, —NR$^a$C$_{2-6}$alkylOR$^f$, —C(=O)R$^e$, —C(=O)OR$^e$, —OC(=O)R$^e$, —C(=O)NR$^a$R$^f$ and —NR$^a$C(=O)R$^e$; and unsaturated carbon atoms may be additionally substituted by =O; and any available nitrogen atoms in the heterocycle and bridge are substituted by H, —C$_{1-6}$alkylOR$^f$, R$^e$, —C$_{1-6}$alkylNR$^a$R$^f$, —C$_{1-3}$alkylC(=O)OR$^e$, —C$_{1-3}$alkylC(=O)NR$^a$R$^f$, —C$_{1-3}$alkylOC(=O)R$^e$, —C$_{1-3}$alkylNR$^a$C(=O)R$^e$, —C(=O)R$^c$ or —C$_{1-3}$alkylR$^c$.

7. A compound according to claim 1, wherein R$^5$ is independently, at each instance, R$^f$, R$^g$, halo, nitro, cyano, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(=O)NR$^a$R$^f$, —C(=O)NR$^a$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-8}$alkylOR$^f$, —C$_{1-6}$alkylNR$^a$R$^f$, —S(=O)$_n$R$^e$, —S(=O)$_2$NR$^a$R$^f$, —NR$^a$S(=O)$_2$R$^e$, —OC(=O)NR$^a$R$^f$, a phenyl ring substituted with 0, 1, 2, or 3 substituents independently selected from R$^{10}$; or R$^5$ is a saturated or unsaturated 5- or 6-membered ring heterocycle containing 1, 2 or 3 atoms selected from O, N and S, substituted with 0, 1, 2, or 3 substituents independently selected from R$^{10}$.

8. A compound according to claim 1, wherein R$^7$ is independently, at each instance, C$_{3-5}$alkyl or C$_{1-2}$haloalkyl.

9. A compound according to claim 1, wherein R$^{10}$ and R$^{11}$ together are a saturated or unsaturated 3-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$.

10. A compound according to claim 1, wherein R$^{10}$ and R$^{11}$ together are a saturated or unsaturated 3-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from =O, $R^e$, halo, cyano, nitro, —C(=O)$R^e$, —C(=O)O$R^e$, —C(=O)N$R^a R^f$, —C(=N$R^a$)N$R^a R^f$, —O$R^f$, —OC(=O)$R^e$, —OC(=O)N$R^a R^f$, —OC(=O)N($R^f$)S(=O)$_2 R^e$, —O$C_{2-6}$alkylN$R^a R^f$, —O$C_{2-6}$alkylO$R^f$, —S$R^f$, —S(=O)$R^e$, —S(=O)$_2 R^e$, —S(=O)$_2$N$R^a R^f$, —S(=O)$_2$N($R^f$)C(=O)$R^e$, —S(=O)$_2$N($R^f$)C(=O)O$R^e$, —S(=O)$_2$N($R^f$)C(=O)N$R^a R^f$, —N$R^a R^f$, —N($R^f$)C(=O)$R^e$, —N($R^f$)C(=O)O$R^e$, —N($R^f$)C(=O)N$R^a R^f$, —N($R^f$)C(=N$R^a$)N$R^a R^f$, —N($R^f$)S(=O)$_2 R^e$, —N($R^f$)S(=O)$_2$N$R^a R^f$, —N$R^f C_{2-6}$alkylN$R^a R^f$ and —N$R^f C_{2-6}$alkylO$R^f$.

11. A compound according to claim 1, wherein $R^{10}$ and $R^{11}$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 1 or 2 substituents selected from $R^e$, halo, cyano, nitro, —C(=O)$R^e$, —C(=O)O$R^e$, —C(=O)N$R^a R^f$, —C(=N$R^a$)N$R^a R^f$, —O$R^f$, —OC(=O)$R^e$, —OC(=O)N$R^a R^f$, —OC(=O)N($R^f$)S(=O)$_2 R^e$, —O$C_{2-6}$alkylN$R^a R^f$, —O$C_{2-6}$alkylO$R^f$, —S$R^f$, —S(=O)$R^e$, —S(=O)$_2 R^e$, —S(=O)$_2$N$R^a R^f$, —S(=O)$_2$N($R^f$)C(=O)$R^e$, —S(=O)$_2$N($R^f$)C(=O)O$R^e$, —S(=O)$_2$N($R^f$)C(=O)N$R^a R^f$, —N$R^a R^f$, —N($R^f$)C(=O)$R^e$, —N($R^f$)C(=O)O$R^e$, —N($R^f$)C(=O)N$R^a R^f$, —N($R^f$)C(=N$R^a$)N$R^a R^f$, —N($R^f$)S(=O)$_2 R^e$, —N($R^f$)S(=O)$_2$N$R^a R^f$, —N$R^f C_{2-6}$alkylN$R^a R^f$ and —N$R^f C_{2-6}$alkylO$R^f$.

12. A compound according to claim 1, wherein $R^{11}$ and $R^{12}$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from =O, $R^e$, halo, cyano, nitro, —C(=O)$R^e$, —C(=O)O$R^e$, —C(=O)N$R^a R^f$, —C(=N$R^a$)N$R^a R^f$, —O$R^f$, —OC(=O)$R^e$, —OC(=O)N$R^a R^f$, —OC(=O)N($R^f$)S(=O)$_2 R^e$, —O$C_{2-6}$alkylN$R^a R^f$, —O$C_{2-6}$alkylO$R^f$, —S$R^f$, —S(=O)$R^e$, —S(=O)$_2 R^e$, —S(=O)$_2$N$R^a R^f$, —S(=O)$_2$N($R^f$)C(=O)$R^e$, —S(=O)$_2$N($R^f$)C(=O)O$R^e$, —S(=O)$_2$N($R^f$)C(=O)N$R^a R^f$, —N$R^a R^f$, —N($R^f$)C(=O)$R^e$, —N($R^f$)C(=O)O$R^e$, —N($R^f$)C(=O)N$R^a R^f$, —N($R^f$)C(=N$R^a$)N$R^a R^f$, —N($R^f$)S(=O)$_2 R^e$, —N($R^f$)S(=O)$_2$N$R^a R^f$, —N$R^f C_{2-6}$alkylN$R^a R^f$ and —N$R^f C_{2-6}$alkylO$R^f$.

13. A compound according to claim 1, wherein $R^{11}$ and $R^{12}$ together are a saturated or unsaturated 3-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from =O, $R^e$, halo, cyano, nitro, —C(=O)$R^e$, —C(=O)O$R^e$, —C(=O)N$R^a R^f$, —C(=N$R^a$)N$R^a R^f$, —OR, —OC(=O)$R^e$, —OC(=O)N$R^a R^f$, —OC(=O)N($R^f$)S(=O)$_2 R^e$, —O$C_{2-6}$alkylN$R^a R^f$, —O$C_{2-6}$alkylO$R^f$, —S$R^f$, —S(=O)$R^e$, —S(=O)$_2 R^e$, —S(=O)$_2$N$R^a R^f$, —S(=O)$_2$N($R^f$)C(=O)$R^e$, —S(=O)$_2$N($R^f$)C(=O)O$R^e$, —S(=O)$_2$N($R^f$)C(=O)N$R^a R^f$, —N$R^a R^f$, —N($R^f$)C(=O)$R^e$, —N($R^f$)C(=O)O$R^e$, —N($R^f$)C(=O)N$R^a R^f$, —N($R^f$)C(=N$R^a$)N$R^a R^f$, —N($R^f$)S(=O)$_2 R^e$, —N($R^f$)S(=O)$_2$N$R^a R^f$, —N$R^f C_{2-6}$alkylN$R^a R^f$ and —N$R^f C_{2-6}$alkylO$R^f$.

14. A compound according to claim 1, wherein $R^{11}$ and $R^{12}$ together are a saturated or unsaturated 3-atom bridge containing 1 or 2 atoms selected from O, N and S with the remaining atoms being carbon, wherein the bridge is substituted by $R^e$, C(=O)$R^e$, —C(=O)O$R^e$, —C(=O)N$R^a R^f$, —C(=N$R^a$)N$R^a R^f$, —O$R^f$, —OC(=O)$R^e$, —OC(=O)N$R^a R^f$, —OC(=O)N($R^f$)S(=O)$_2 R^e$, —O$C_{2-6}$alkylN$R^a R^f$, —O$C_{2-6}$alkylO$R^f$, —S$R^f$, —S(=O)$R^e$, —S(=O)$_2 R^e$, —S(=O)$_2$N$R^a R^f$, —S(=O)$_2$N($R^f$)C(=O)$R^e$, —S(=O)$_2$N($R^f$)C(=O)O$R^e$, —S(=O)$_2$N($R^f$)C(=O)N$R^a R^f$, —N$R^a R^f$, —N($R^f$)C(=O)$R^e$, —N($R^f$)C(=O)O$R^e$, —N($R^f$)C(=O)N$R^a R^f$, —N($R^f$)C(=N$R^a$)N$R^a R^f$, —N($R^f$)S(=O)$_2 R^e$, —N($R^f$)S(=O)$_2$N$R^a R^f$, —N$R^f C_{2-6}$alkylN$R^a R^f$ or —N$R^f C_{2-6}$alkylO$R^f$.

15. A compound according to claim 1, wherein $R^{11}$ and $R^{12}$ together are a saturated or unsaturated 3-atom bridge containing 1 or 2 atoms selected from O, N and S with the remaining atoms being carbon, wherein the bridge is substituted by —C(=O)$R^e$, —C(=O)O$R^e$, —C(=O)N$R^a R^f$, —C(=N$R^a$)N$R^a R^f$, —OC(=O)N$R^a R^f$, —OC(=O)N($R^f$)S(=O)$_2 R^e$, —O$C_{2-6}$alkylN$R^a R^f$, —O$C_{2-6}$alkylO$R^f$, —S$R^f$, —S(=O)$R^e$, —S(=O)$_2 R^e$, —S(=O)$_2$N$R^a R^f$, —S(=O)$_2$N($R^f$)C(=O)$R^e$, —S(=O)$_2$N($R^f$)C(=O)O$R^e$, —S(=O)$_2$N($R^f$)C(=O)N$R^a R^f$, —N$R^a R^f$, —N($R^f$)C(=O)$R^e$, —N($R^f$)C(=O)O$R^e$, —N($R^f$)C(=O)N$R^a R^f$, —N($R^f$)C(=N$R^a$)N$R^a R^f$, —N($R^f$)S(=O)$_2 R^e$, —N($R^f$)S(=O)$_2$N$R^a R^f$, —N$R^f C_{2-6}$alkylN$R^a R^f$ or —N$R^f C_{2-6}$alkylO$R^f$.

16. A compound according to claim 1, wherein $R^3$ is H.

17. A compound according to claim 1, wherein $R^2$ is H.

18. A method of making a compound according to claim 1, comprising the step of:
reacting

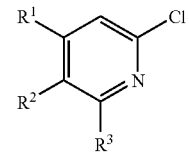

with $R^4 NH_2$ to form

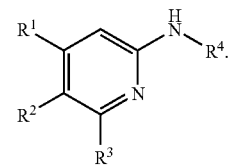

19. A pharmaceutical composition comprising a compound according to claim 1 and a pharmaceutically-acceptable diluent or carrier.

* * * * *